United States Patent
Kumar et al.

(10) Patent No.: US 12,070,308 B2
(45) Date of Patent: Aug. 27, 2024

(54) SYSTEMS, DEVICES, AND METHODS OF ANALYTE MONITORING

(71) Applicant: Abbott Diabetes Care Inc., Alameda, CA (US)

(72) Inventors: Panganamala Ashwin Kumar, Oakland, CA (US); Timothy C. Dunn, San Francisco, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 319 days.

(21) Appl. No.: 17/329,065

(22) Filed: May 24, 2021

(65) Prior Publication Data

US 2021/0361199 A1    Nov. 25, 2021

Related U.S. Application Data

(60) Provisional application No. 63/080,763, filed on Sep. 20, 2020, provisional application No. 63/034,118, (Continued)

(51) Int. Cl.
    *A61B 5/145* (2006.01)
    *A61B 5/00* (2006.01)

(52) U.S. Cl.
    CPC ........ *A61B 5/14532* (2013.01); *A61B 5/0022* (2013.01); *A61B 5/7264* (2013.01); (Continued)

(58) Field of Classification Search
    CPC . A61B 5/14532; A61B 5/0022; A61B 5/7264; A61B 5/7405; A61B 5/746
    See application file for complete search history.

(56) References Cited

U.S. PATENT DOCUMENTS

| | | |
|---|---|---|
| 6,605,200 B1 | 8/2003 | Mao et al. |
| 6,932,894 B2 | 8/2005 | Mao et al. |

(Continued)

FOREIGN PATENT DOCUMENTS

| | | |
|---|---|---|
| WO | WO 2018/136898 A1 | 7/2018 |
| WO | WO 2019/236850 A1 | 12/2019 |

OTHER PUBLICATIONS

Costa et al., "Clinical Performance of Flash Glucose Monitoring System in Patients with Liver Cirrhosis and Diabetes Mellitus," Scientific Reports 10:7460 (2020).

(Continued)

*Primary Examiner* — Charles A Marmor, II
*Assistant Examiner* — Meghan R Kumar
(74) *Attorney, Agent, or Firm* — Baker Botts L.L.P.

(57) ABSTRACT

A glucose monitoring system includes a sensor control device comprising an analyte sensor coupled with sensor electronics, the sensor control device configured to transmit data indicative of an analyte level, and a reader device comprising a wireless communication circuitry configured to receive the data indicative of the analyte level, and one or more processors coupled with a memory. The memory is configured to store instructions that, when executed by the one or more processors, cause the one or more processors to: determine a frequency of interaction over a first time period based on one or more instances of user operation of the reader device, and output a first notification if the determined frequency of interaction is below a predetermined target level of interaction and output a second notification if the determined frequency of interaction is above the predetermined target level of interaction, wherein below the predetermined target level of interaction, an increase in the determined frequency of interaction corresponds to a first improvement in a metabolic parameter, and above the pre- (Continued)

determined target level of interaction, an increase in the determined frequency of interaction corresponds to a second improvement in the metabolic parameter.

47 Claims, 70 Drawing Sheets

Related U.S. Application Data filed on Jun. 3, 2020, provisional application No. 63/029,339, filed on May 22, 2020.

(52) U.S. Cl.
CPC ............ *A61B 5/7405* (2013.01); *A61B 5/742* (2013.01); *A61B 5/746* (2013.01); *A61B 5/6801* (2013.01)

(56) References Cited

U.S. PATENT DOCUMENTS

| | | | |
|---|---|---|---|
| 8,280,474 | B2 | 10/2012 | Liu et al. |
| 9,913,600 | B2 | 3/2018 | Taub et al. |
| 10,856,785 | B2 | 12/2020 | Taub et al. |
| 2008/0071580 | A1 | 3/2008 | Marcus et al. |
| 2008/0154513 | A1 | 6/2008 | Kovatchev et al. |
| 2010/0240079 | A1* | 9/2010 | Jackson ............ A61B 5/150022 435/14 |
| 2011/0319322 | A1 | 12/2011 | Bashan et al. |
| 2012/0232368 | A1 | 9/2012 | Jin et al. |
| 2016/0038077 | A1* | 2/2016 | Otto ..................... A61B 5/4833 600/365 |
| 2016/0042154 | A1 | 2/2016 | Goldberg et al. |
| 2017/0112421 | A1* | 4/2017 | Taub ..................... G16H 40/63 |
| 2017/0347971 | A1* | 12/2017 | Davis ................. A61B 5/14546 |
| 2018/0192927 | A1* | 7/2018 | Taub ..................... G16H 40/67 |
| 2020/0196919 | A1 | 6/2020 | Rao et al. |
| 2022/0023391 | A1* | 1/2022 | Michelich .......... A61B 5/14532 |

OTHER PUBLICATIONS

International Search Report and Written Opinion mailed Sep. 28, 2021 in International Application No. PCT/US21/33947.
International Search Report and Written Opinion mailed Sep. 30, 2021 in International Application No. PCT/US21/33946.
Kompala et al., "A New Era: Increasing Continuous Glucose Monitoring Use in Type 2 Diabetes," Evidence-Based Diabetes Management 25(4):4 pgs. (2019).
Sato et al., "Glucose Variability Based on Continuous Glucose Monitoring Assessment Is Associated with Postoperative Complications after Cardiovascular Surgery," Annals of and Cardiovascular Surgery 23:239-247 (2017).
Shi et al., "Cost Comparison of Flash Continuous Glucose Monitoring with Self-monitoring of Blood Glucose in Adults with Type 1 or Type 2 Diabetes Using Intensive Insulin—From a US Private Payer Perspective," US Endocrinology 16(1):24-30 (2020).
U.S. Appl. No. 17/329,101, filed May 24, 2021.
"The frequency of FreeStyle Libre glucose sensor scans performed by the diabetic patient on a daily basis is associated with better parameters for monitoring his glucose profile: Analysis of 312 million hours of monitoring in real life in France," Medecine des Maladies Metaboliques, vol. 14, Issue 7 in Nov. 2020 and can be accessed at the website https://www.sciencedirect.com/science/article/pii/S1957255720002163 [with English translations of Summary, Method, Results and Conclusion].
Bailey et al., "The Performance and Usability of a Factory-Calibrated Flash Glucose Monitoring System," Diabetes Tech. Ther., 17(11):787-794 (2015).

Bergenstal et al., "Flash CGM Is Associated with Reduced Diabetes Events and Hospital-izations in Insulin-Treated Type 2 Diabetes," Journal of the Endocrine Society, vol. 5, Issue 4, pp. 1-9, 2021 https://academic.oup.com/jes/article/5/4/bvab013/6126709.
Bolinder et al., "Novel glucose-sensing technology and hypoglycaemia in type 1 diabetes: a multicentre, non-masked, randomized controlled trial," Lancet, 388(10057):2254-2263 (2016).
Deshmukh et al., "Effect of Flash Glucose Monitoring On Glycemic Control, Hypoglyce-mia, Diabetes-Related Distress, and Resource Utilization in the Association of British Clinical Diabetologists (ABCD) Nationwide Audit," J Diabetes Care, 43(9):2153-2160 (2020).
Dunn et al., "Real-world flash glucose monitoring patterns and associations between self-monitoring frequency and glycaemic measures: A European analysis of over 60 million glucose tests," Diabetes Res. & Clinical Practice, 137:37-46 (2018).
Evans et al., "The Impact of Flash Glucose Monitoring on Glycaemic Control as Measured by HbA1c: A Meta-analysis of Clinical Trials and Real-World Observational Studies," Diabetes Therapy, 11(1):83-95 (2020).
Fokkert et al., "Improved well-being and decreased disease burden after 1-year use of flash glucose monitoring (FLARE-NL4)," BMJ Open Diabetes Research & Care, 7:e000809 (2019) 10 pgs.
Haak et al., "Use of Flash Glucose-Sensing Technology for 12 months as a Replacement for Blood Glucose Monitoring in Insulin-treated Type 2 Diabetes," Diabetes Therapy 8(3):573-586 (2017).
Heller et al., "Severe Hypoglycaemia in adults with insulin-treated diabetes: impact on healthcare resources," J Diabetic Medicine 33(4):471-477 (2016).
Ida et al., Effects of Flash Glucose Monitoring on Dietary Variety, Physical Activity, and Self-Care Behaviors in Patients with Diabetes, J. Diabetes Res., 2020.
Krakauer et al., "A review of flash glucose monitoring in type 2 diabetes," Diabetology & Metabolic Syndrome, vol. 13:42 (2021) 10 pgs. https://dmsjournal.biomedcentral.com/articles/10.1186/s13098-021-00654-3.
Kroger et al., "Three European Retrospective Real-World Chart Review Studies to Determine the Effectiveness of Flash Glucose Monitoring on HbA1c in Adults with Type 2 Diabetes," Diabetes Therapy 11:279-291 (2020).
Nathan et al., "Translating the A1C Assay into Estimated Average Glucose Values," Diabetes Care 31:1473-1478 (2008).
Ogawa et al., "Effect of the Freestyle Libre Flash Glucose Monitoring System on Glycemic Control in individuals with Type 2 Diabetes Treated with Basal-Bolus Insulin Therapy: An Open Label, Prospective, Multicenter Trial in Japan," J. Diabetes Investigation 12(1):82-90 (2021).
Rose et al., "Improving HbA1c Control in Type 1 or Type 2 Diabetes Using Flash Glucose Monitoring: A Retrospective Observational Analysis in Two German Centres," Diabetes Therapy, vol. 12, pp. 363-372, 2021 https://link.springer.com/article/10.1007/s13300-020-00978-9.
Wada et al., "Flash glucose monitoring Helps achieve better glycemic control than conventional self-monitoring of blood glucose in non-insulin treated type 2 diabetes: a randomized controlled trial," BMJ Open Diabetes Res. Care, 8:e001115 (2020).
Xu et al., "Accurate prediction of HbA 1c by continuous glucose monitoring using a kinetic model with patient-specific parameters for red blood cell lifespan and glucose uptake," Diabetes and Vascular Disease Research, vol. 18, Issue 3, 2021 https://journals.sagepub.com/doi/full/10.1177/14791641211013734.
Yaron et al., "Effect of Flash Glucose Monitoring Technology on Glycemic Control and Treatment Satisfaction in Patients with Type 2 Diabetes," Diabetes Care, 42:1178-1184 (2019).
U.S. Appl. No. 17/329,101, filed Sep. 6, 2023 Non-Final Office Action.

* cited by examiner

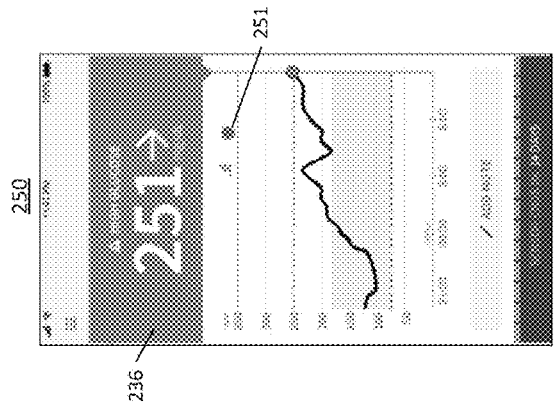
FIG. 2D
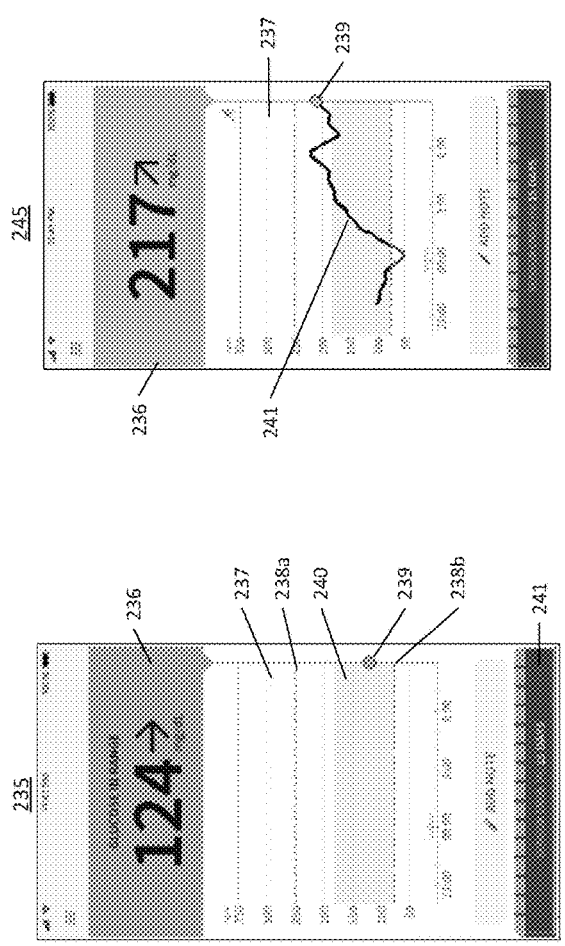
FIG. 2E
FIG. 2F
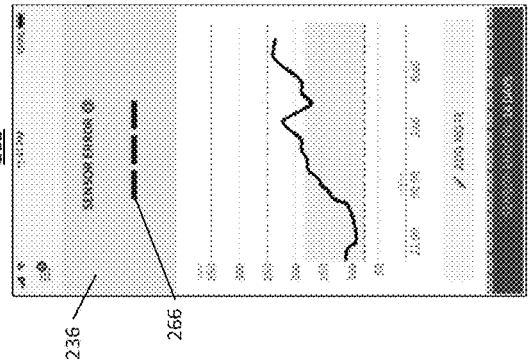
FIG. 2G
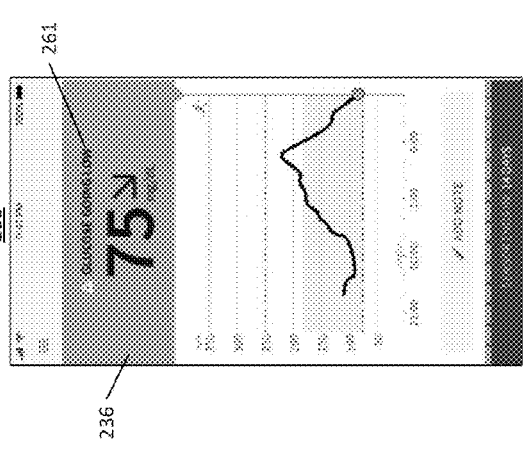
FIG. 2H
FIG. 2I

FIG. 5D

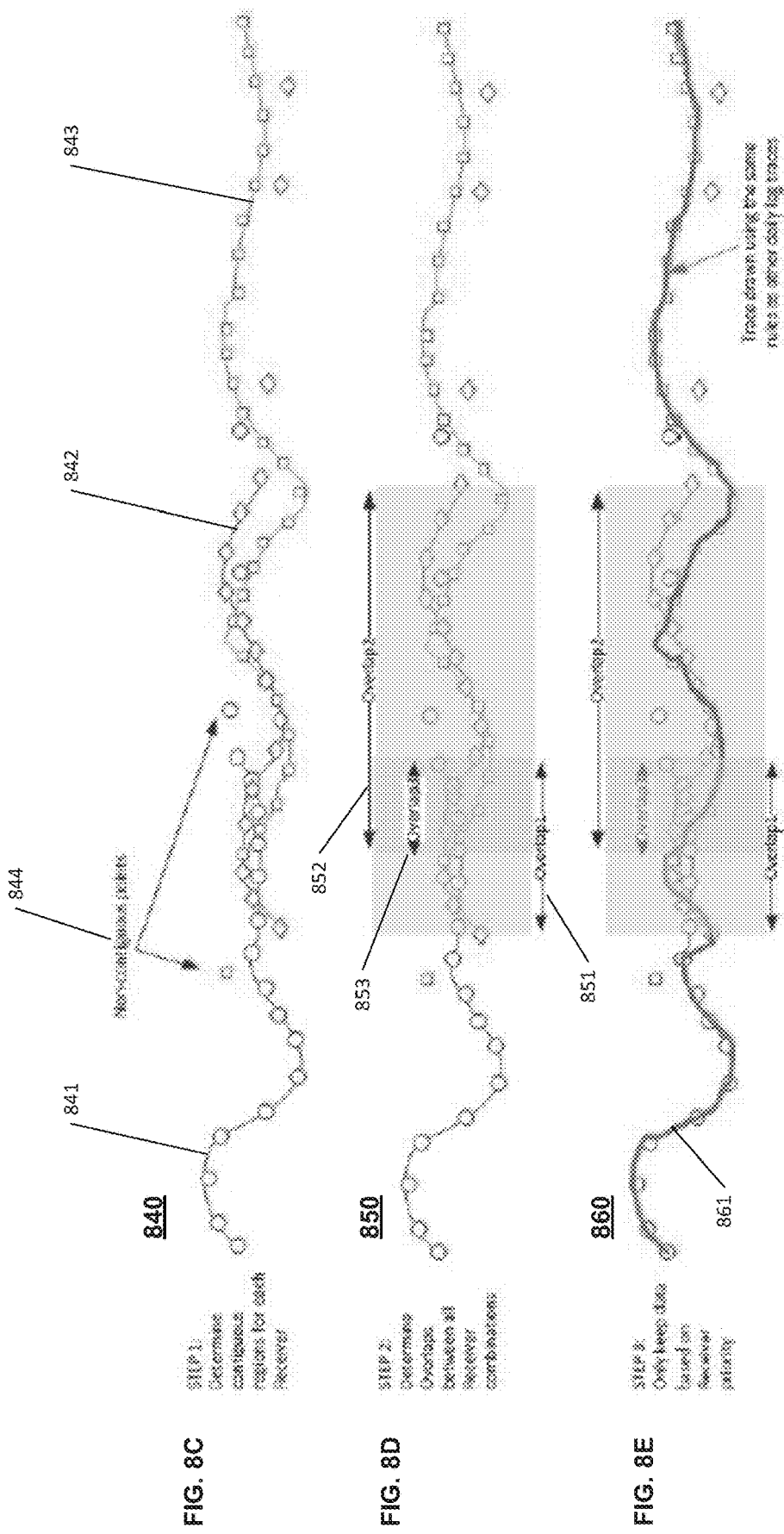

| Study title or author | Year | Study design | Sample size Disease/treatment | Observation period | Outcome measures* | Country/race |
|---|---|---|---|---|---|---|
| IMPACT | 2016 | RCT | Type 1 diabetes Multiple injections and CSII Flash glucose monitoring group: 119 patients SMBG group: 120 patients | 6 months | Time in hypoglycemia TIR, HbA1c SMBG frequency, DTSQ, DQoL, etc. | Sweden, Austria, Germany, Spain, Netherlands/ white, black |
| REPLACE 6 months | 2017 | RCT | Type 2 diabetes Multiple injections and CSII Flash glucose monitoring group: 149 patients SMBG group: 75 patients | 6 months | HbA1c Time in hypoglycemia SMBG frequency, DTSQ, DQoL, etc. | France, Germany, UK/ white, black, Asian, Pacific Islander, other |
| REPLACE 12 months | 2017 | Prospective observational study | Type 2 diabetes Multiple injections and CSII 139 patients | 6 months | Changes in sensor-derived glycemic measures Time in hypoglycemia, SMBG frequency, etc. | France, Germany, UK/ white, black, Asian, Pacific Islander, other |
| Dunn et al. | 2018 | RWD study | 50,831 patients with type 1 and type 2 diabetes | At least 5 days | Scan frequency, eA1c Time in hypoglycemia, etc. | N/A |
| SELFY | 2018 | Prospective (single arm) study | Type 1 diabetes Using insulin (administered by injections or CSII) 76 children and teenagers with T1D SMBG | 18 weeks | T1R Time in hyperglycemia, frequency and duration of hyperglycemia/hypoglycemia, HbA1c etc. | UK, Ireland, Germany/not described |
| Yaron et al. | 2019 | RCT | Type 2 diabetes Multiple injections Flash glucose monitoring group: 53 patients SMBG group: 48 patients | 10 weeks | DTSQ, HbA1c, etc. | Israel/not described |
| FLARE-NL4 | 2019 | Prospective registry study | Using insulin 1,054 patients with type 1 diabetes 223 patients with type 2 diabetes | 12 months | HbA1c SF-12v2, EQ-5D-3L, diabetes-related hospital admission rate, work absenteeism rate, etc. | Netherlands/not described |
| Evans et al. | 2019 | Meta-analysis | 25 studies 1,496 patients with type 1 diabetes 227 patients with type 2 diabetes | 1–12 months | HbA1c | N/A |
| Kröger et al. | 2019 | Chart review | Type 2 diabetes Multiple injections and CSII 363 patients | 3–6 months | HbA1c | France, Austria, Germany/not described |

FIG. 13A

| Study title or author | Year | Study design | Sample size Disease/treatment | Observation period | Outcome measures* | Country/race |
|---|---|---|---|---|---|---|
| Overend et al. (ABCD manuscript) | 2019 | Prospective observational study | Type 1 diabetes 40 patients with T1D | 6 months | DQoL HbA1c, hypoglycaemia | UK/ not described |
| FUTURE (Charleer et al.) | 2019 | Prospective observational study RWD study | Type 1 diabetes 1,913 patients with T1D | 12 months | DQoL, HbA1c, time in hyperglycemia/ hypoglycemia, ketoacidosis, work absenteeism | Belgium/not described |
| Tyndall et al. (Tyndall from 2019) | 2019 | Prospective observational study | Type 1 diabetes 900 patients with T1D | 2 months | HbA1c hypoglycaemia, DQoL, flash monitoring data and hospital admissions | UK/ not described |
| Gomez-Peralta et al. | 2020 | RWD study | 22,949 readers 207,386 sensors | 52 months | Scan frequency, eA1c, TIR, time in hyperglycemia, time in hypoglycemia, etc. | N/A |
| Calliari et al. | 2020 | RWD study | 17,691 readers 147,166 sensors | 52 months | Scan frequency, eA1c, TIR, time in hyperglycemia, time in hypoglycemia. | N/A |
| Wada et al. | 2020 | RCT | Type 2 diabetes Oral agents 100 patients | 24 weeks | HbA1c Changes in BMI, blood pressure, fasting plasma glucose, triglycerides, HDL cholesterol, LDL cholesterol, uric acid, urinary albumin, DTSQ score, antidiabetic drugs, glucose variability measures, etc. | Japan/not described |
| Ida et al. | 2020 | Observational study | Multiple injections 42 patients with type 1 diabetes 48 patients with type 2 diabetes | 12 weeks | HbA1c, SD, MAGE, CV, MODD, AAC, AUC, self-administered questionnaires (DVS, IPAQ, SDSCA, DTSQ), etc. | Japan/not described |
| SHIFT | 2020 | Prospective (single-arm) study | Type 2 diabetes 94 patients using insulin | 11 weeks | Time in hypoglycemia TIR, frequency and duration of hyperglycemia/hypoglycemia, eA1c, AUC, SD, LBGI, HBGI, SD of glucose rate of change, CONGA, etc. | Japan/not described |
| Al Hayek et al. | 2020 | Prospective observational study | Type 1 diabetes Multiple injections 67 patients with T1D | 6 months | HbA1c Standard questionnaire for acceptability measures | Saudi Arabia/not described |
| Tsur et al. | 2020 | RWD study | Type 1 diabetes 3490 patients with T1D | 14 months | HbA1c Internal medicine hospitalizations, Rate of glucose test strip purchases, etc. | Israel/not described |

FIG. 13B

|   | N | Baseline Mean ± SD | Final phase Mean ± SD | Change Mean ± SD | 95% CI for change | p value |
|---|---|---|---|---|---|---|
| Austria |   |   |   |   |   |   |
| HbA1c (%) | 92 | 8.8 ± 0.8 | 7.9 ± 1.0 | −0.9 ± 0.8 | (−1.0, −0.7) | < 0.0001 |
| HbA1c (mmol/mol) | 92 | 72.2 ± 8.9 | 62.6 ± 10.5 | −9.6 ± 8.8 | (−11.4, −7.7) | < 0.0001 |
| France |   |   |   |   |   |   |
| HbA1c (%) | 88 | 9.0 ± 0.9 | 8.2 ± 1.1 | −0.8 ± 1.1 | (−1.1, −0.6) | < 0.0001 |
| HbA1c (mmol/mol) | 88 | 74.7 ± 9.7 | 65.9 ± 12.5 | −8.9 ± 12.5 | (−11.5, −6.3) | < 0.0001 |
| Germany |   |   |   |   |   |   |
| HbA1c (%) | 183 | 8.9 ± 0.9 | 7.9 ± 0.9 | −0.9 ± 1.1 | (−1.1, −0.8) | < 0.0001 |
| HbA1c (mmol/mol) | 183 | 73.1 ± 10.3 | 63.0 ± 9.6 | −10.1 ± 12.2 | (−11.9, −8.3) | < 0.0001 |

| | From Sept 2014 to June 2017 | to Sept 2018 |
|---|---|---|
| Number of readers | 20 960 | 97 788 |
| Number of sensors | 112 065 | 1 068 269 |
| Number of scans | 16.7 million | 141 million |
| Number of hours of recording | 32.9 million | 312 million |
| Number of IM values recorded | 0.132 billion | 1.25 trillion |

FIG. 14H

| Classe | Lecteurs (n) | fréquence scans/Jour | HbA1c estimée (%) | DS HbA1c estimée (%) | 95% IC HbA1c estimée (%) | T<45 minutes/jour | T<55 minutes/jour | T<70 minutes/jour | TIR 70-180 heures/jour | T>180 heures/jour | T>240 heures/jour | Glucose CV (%) |
|---|---|---|---|---|---|---|---|---|---|---|---|---|
| 1 | 4889 | 3,3 | 8,11 | 1,19 | 8,06-8,15 | 19,9 | 36,9 | 80,0 | 11,8 | 10,9 | 5,7 | 40,1% |
| 2 | 4889 | 4,2 | 8,05 | 1,18 | 8,01-8,08 | 22,1 | 40,6 | 86,7 | 11,8 | 10,8 | 5,6 | 41,5% |
| 3 | 4889 | 4,8 | 8,00 | 1,16 | 7,97-8,03 | 21,8 | 41,2 | 89,3 | 11,8 | 10,7 | 5,6 | 41,9% |
| 4 | 4889 | 5,4 | 7,94 | 1,15 | 7,91-7,97 | 22,5 | 42,3 | 92,3 | 11,9 | 10,5 | 5,4 | 42,2% |
| 5 | 4889 | 5,9 | 7,88 | 1,12 | 7,85-7,91 | 22,4 | 42,3 | 93,2 | 12,1 | 10,4 | 5,2 | 42,2% |
| 6 | 4889 | 6,4 | 7,85 | 1,13 | 7,82-7,89 | 21,2 | 40,9 | 92,4 | 12,2 | 10,3 | 5,2 | 42,3% |
| 7 | 4889 | 6,9 | 7,79 | 1,10 | 7,76-7,82 | 22,5 | 43,2 | 96,2 | 12,3 | 10,1 | 5,0 | 42,6% |
| 8 | 4889 | 7,4 | 7,73 | 1,08 | 7,70-7,76 | 22,3 | 42,9 | 97,0 | 12,5 | 9,9 | 4,9 | 42,6% |
| 9 | 4889 | 7,9 | 7,74 | 1,13 | 7,71-7,78 | 21,2 | 41,5 | 95,4 | 12,4 | 10,0 | 4,9 | 42,6% |
| 10 | 4889 | 8,5 | 7,71 | 1,13 | 7,68-7,74 | 21,9 | 42,2 | 96,4 | 12,5 | 9,9 | 4,8 | 42,4% |
| 11 | 4889 | 9,0 | 7,64 | 1,14 | 7,61-7,67 | 20,2 | 40,2 | 95,1 | 12,8 | 9,8 | 4,6 | 42,2% |
| 12 | 4889 | 9,6 | 7,65 | 1,15 | 7,61-7,69 | 19,8 | 39,3 | 93,2 | 12,7 | 9,7 | 4,6 | 42,1% |
| 13 | 4889 | 10,2 | 7,57 | 1,17 | 7,54-7,61 | 19,0 | 38,5 | 93,3 | 13,0 | 9,4 | 4,4 | 41,9% |
| 14 | 4889 | 10,8 | 7,56 | 1,15 | 7,52-7,59 | 19,1 | 38,4 | 93,5 | 13,1 | 9,4 | 4,3 | 41,8% |
| 15 | 4889 | 11,5 | 7,49 | 1,22 | 7,46-7,53 | 18,9 | 38,1 | 93,3 | 13,3 | 9,1 | 4,2 | 41,6% |
| 16 | 4889 | 12,3 | 7,45 | 1,30 | 7,41-7,48 | 18,4 | 37,5 | 93,4 | 13,5 | 9,0 | 4,0 | 41,6% |
| 17 | 4889 | 13,3 | 7,41 | 1,24 | 7,37-7,44 | 18,1 | 36,9 | 93,1 | 13,6 | 8,8 | 3,9 | 41,1% |
| 18 | 4889 | 14,8 | 7,33 | 1,22 | 7,29-7,36 | 17,2 | 35,7 | 92,1 | 14,0 | 8,5 | 3,7 | 40,6% |
| 19 | 4889 | 17,3 | 7,26 | 1,19 | 7,23-7,30 | 17,0 | 35,3 | 92,0 | 14,2 | 8,2 | 3,5 | 40,3% |
| 20 | 4897 | 26,4 | 7,03 | 1,17 | 7,00-7,06 | 14,8 | 31,6 | 89,2 | 15,2 | 7,3 | 3,0 | 38,8% |

FIG. 14I

| Characteristic | | n (%) |
| --- | --- | --- |
| Gender | Female | 26 (48%) |
| | Male | 28 (52%) |
| Age in years | Overall mean 41.6 (range, 29–55) | |
| | 25–34 | 8 (15%) |
| | 35–44 | 30 (55%) |
| | 45–55 | 16 (30%) |
| Body mass index (BMI)kg/m² | Overall mean 31.5 | |
| | BMI <25 | 2 (4%) |
| | 25≤ BMI <30 | 14 (26%) |
| | BMI ≥30 | 38 (70%) |
| Waist-to-height ratio (WtHR)† | WtHR <0.5 | 1 (2%) |
| | 0.5≤ WtHR <0.6 | 22 (41%) |
| | WtHR ≥0.6 | 31 (57%) |
| Duration of diabetes in years | Overall mean 3.4 (range 1-6 years) | |
| | <4 years | 29 (54%) |
| | ≥4 years | 25 (46%) |
| Baseline HbA1c | 8.22% (mean) | |
| Total daily dose of insulin | 1.45 ± 0.35 (units/kg/day) | |
| Frequency of glucose monitoring per day | Overall mean 2.48 | |
| | 2 | 31 (57%) |
| | 3 | 20 (37%) |
| | 4 | 3 (6%) |
| Frequency of hypoglycaemic episodes per month | Overall mean 4.43 ± 1.51 | |
| | 2–4 | 28 (52%) |
| | 5–7 | 25 (46%) |
| | >7 | 1 (2%) |

FIG. 15A

| Measure | Baseline mean ± SD (range) | 12-week mean ± SD (range) | Mean difference | P-value | 95% confidence interval |
|---|---|---|---|---|---|
| HbA1c% (range) | 8.22 ± 0.69 (7.2–11.1) | 7.78 ± 0.71 (6.2–9.9) | -0.44 | <0.001* | 0.40, 0.60 |
| Confirmed hypoglycaemic episodes per month (range) | 4.43 ± 1.51 (2–8) | 1.24 ± 1.15 (0–4) | -3.19 | <0.001* | 2.64, 3.73 |
| Total daily dose of insulin Units/kg/day (range) | 1.45 ± 0.35 (0.9–2.1) | 1.02 ± 0.26 (0.6–1.7) | -0.43 | <0.001* | 0.35, 0.55 |
| Frequency of glucose monitoring per day (range) | 2.48 ± 0.60 (2–4) | 7.61 ± 1.73 (4–12) | 5.13 | <0.001* | 4.50, 5.50 |
| Body mass index (kg/m$^2$) (range) | 31.5 ± 3.04 (24.4–37.9) | 30.7 ± 2.93 (24.1–37.5) | -0.80 | <0.001* | 0.61, 0.99 |
| Waist-to-height ratio (WtHr) (range) | 0.61 ± 0.06 (0.49–0.73) | 0.60 ± 0.05 (0.49–0.73) | -0.01 | <0.001* | 0.01, 0.02 |

FIG. 15B

| Monitoring hours | 48.7 million | 3.02 billion |
|---|---|---|
| Automatically recorded glucose readings | 195 million | 12.1 billion |
| Number of readers | 16,331 | 932,793 |
| Daily scans | 13.4 (8.9) | 13.2 (10.7) |
| eHbA1c (%) | 7.7 (1.4) | 7.5 (1.5) |
| eHbA1c (mmol/mol) | 61 (15.3) | 58 (16.4) |
| Hours per day glucose > 10.0 mmol/L | 9.6 (4.7) | 8.8 (5.1) |
| Hours per day glucose 3.9 to 10.0 mmol/L | 13.1 (4.5) | 13.9 (4.9) |
| Minutes per day glucose < 3.9 mmol/L | 54.6 (80.3) | 51.7 (88.6) |
| Minutes per day glucose < 3.0 mmol/L | 13.1 (30.5) | 12.0 (32.8) |
| Minutes per day glucose < 2.5 mmol/L | 4.7 (14.3) | 4.5 (15.6) |

FIG. 16A

| Scan rate per day | Estimated HbA1c (%) | Estimated HbA1c (mmol/mol) | Glucose < 2.5 mmol/L (min/day) | Glucose < 3.0 mmol/L (min/day) | Glucose < 3.9 mmol/L (min/day) | Glucose 3.9 mmol/L (hours/day) | Glucose 3.9-10.0 mmol/L (hours/day) | Glucose >10.0 mmol/L (hours/day) | Glucose > 13.9 mmol/L (hours/day) |
|---|---|---|---|---|---|---|---|---|---|
| 3.7 | 8.6 | 71 | 4.1 | 12.0 | 45.4 | 10.5 | 12.3 | 6.5 | |
| 4.9 | 8.3 | 67 | 5.2 | 14.3 | 53.0 | 11.4 | 11.3 | 5.6 | |
| 5.7 | 8.2 | 66 | 5.3 | 14.3 | 54.5 | 11.7 | 11.0 | 5.3 | |
| 6.5 | 8.1 | 65 | 5.5 | 15.9 | 55.5 | 11.7 | 11.0 | 5.2 | |
| 7.3 | 8.1 | 65 | 5.1 | 13.8 | 53.8 | 11.9 | 10.9 | 5.0 | |
| 8.0 | 8.0 | 64 | 5.0 | 14.1 | 55.9 | 12.0 | 10.8 | 4.7 | |
| 8.7 | 7.9 | 63 | 5.2 | 13.9 | 59.4 | 12.2 | 10.6 | 4.6 | |
| 9.4 | 7.7 | 61 | 4.9 | 14.2 | 57.1 | 12.9 | 9.8 | 4.0 | |
| 10.2 | 7.8 | 61 | 5.4 | 14.6 | 59.6 | 12.8 | 9.9 | 4.1 | |
| 11.0 | 7.7 | 61 | 5.0 | 13.9 | 57.0 | 12.9 | 9.9 | 3.9 | |
| 11.9 | 7.6 | 59 | 5.6 | 15.8 | 60.0 | 13.3 | 9.4 | 3.6 | |
| 12.7 | 7.6 | 60 | 4.6 | 13.0 | 58.1 | 13.2 | 9.5 | 3.7 | |
| 13.7 | 7.5 | 59 | 4.7 | 13.1 | 55.7 | 13.5 | 9.2 | 3.4 | |
| 14.8 | 7.5 | 58 | 5.3 | 14.1 | 56.5 | 13.9 | 8.8 | 3.2 | |
| 16.0 | 7.4 | 57 | 5.0 | 14.2 | 59.6 | 14.1 | 8.6 | 3.0 | |
| 17.5 | 7.5 | 58 | 4.2 | 12.1 | 53.8 | 13.9 | 8.9 | 3.3 | |
| 19.3 | 7.4 | 57 | 4.1 | 11.2 | 50.1 | 14.3 | 8.5 | 3.0 | |
| 21.8 | 7.2 | 55 | 4.0 | 11.8 | 52.5 | 14.8 | 7.9 | 2.6 | |
| 25.8 | 7.2 | 55 | 3.1 | 9.1 | 43.3 | 15.1 | 7.8 | 2.6 | |
| 40.0 | 6.9 | 52 | 2.9 | 8.7 | 49.5 | 16.1 | 6.6 | 2.0 | |

FIG. 16B

| Randomized controlled trial | Outcome (FGMS vs. SMBG) [N=149 vs. N=75] | | P value |
|---|---|---|---|
| Overall population (6 months) | Mean change from baseline in HbA1c: | −0.29 ± 0.07 vs. −0.31 ± 0.09% | P=0.8222 |
| Subgroup analyses (6 months) | | | |
| Age | | | |
| <65 years | Mean change from baseline in HbA1c: | −0.53 ± 0.09 vs. −0.20 ± 0.12% | P=0.0301 |
| ≥65 years | | −0.05 ± 0.10 vs. −0.49 ± 0.13% | P=0.0081 |
| Time spent in hypoglycemia [hours/day]: mean change from baseline | | | |
| Glucose <70 mg/dL | Between-group difference: | −43% [mean ± SE −0.47 ± 0.13] | P=0.0006 |
| Glucose <55 mg/dL | | −53% [−0.22 ± 0.07] | P=0.0014 |
| Glucose <45 mg/dL | | −64% [−0.14 ± 0.04] | P=0.0013 |
| Frequency of hypoglycemic events [per day]: mean change from baseline | | | |
| Glucose <70 mg/dL | Between-group difference: | −28% [mean ± SE −0.16 ± 0.07] | P=0.0164 |
| Glucose <55 mg/dL | | −44% [−0.12 ± 0.04] | P=0.0017 |
| Glucose <45 mg/dL | | −49% [−0.06 ± 0.02] | P=0.0098 |
| AUC [hours/day × mg/dL] | | | |
| Glucose <70 mg/dL | Between-group difference: | −51% [mean ± SE −7.80 ± 2.20] | P=0.0005 |
| Glucose <55 mg/dL | | −60% [−2.51 ± 0.76] | P=0.0012 |
| Glucose <45 mg/dL | | −67% [−0.70 ± 0.22] | P=0.0015 |
| Extension phase | Outcome (FGMS vs. baseline) [N=139] | | |
| Subgroup analyses (12 months) | | | |
| Time spent in hypoglycemia [hours/day] | | | |
| Glucose <70 mg/dL | Mean change from baseline (start of treatment phase): | −50% [mean ± SD −0.70 ± 1.85] | P=0.0002 |
| Glucose <55 mg/dL | | −62% [−0.40 ± 1.09] | P=0.0002 |
| Glucose <45 mg/dL | | −67% [−0.23 ± 0.73] | P=0.0013 |
| Frequency of hypoglycemic events [per day] | | | |
| Glucose <70 mg/dL | Mean change from baseline (start of treatment phase): | −41% [mean ± SD −0.27 ± 0.67] | P<0.0001 |
| Glucose <55 mg/dL | | −56% [−0.20 ± 0.49] | P<0.0001 |
| Glucose <45 mg/dL | | −62% [−0.13 ± 0.35] | P=0.0002 |
| AUC [hours/day × mg/dL] | | | |
| Glucose <70 mg/dL | Mean change from baseline (start of treatment phase): | −58% (mean ± SD −12.73 ± 34.53] | P=0.0002 |
| Glucose <55 mg/dL | | −65% [−4.28 ± 12.76] | P=0.0007 |
| Glucose <45 mg/dL | | −69% [−1.12 ± 3.67] | P=0.0021 |
| BG levels are presented as mg/dL, which can be converted to mmol/L by multiplying values by 0.05551. | | | |
| AUC, area under the concentration-time curve; FGMS, flash glucose monitoring system; HbA1c, glycosylated hemoglobin; SMBG, self-monitoring of blood glucose. | | | |

FIG. 17A

| Study (population) | Effect of: | HbA1c (%) |
|---|---|---|
| Fokkert et al. 2019 [20]<br>T1D, n=1054; T2D, n=223; Other, n=88 | Before vs. after FGMS use on estimated HbA1c | At baseline: 8.0% (95% CI 7.9–8.1)<br>At 6 months: 7.6% (95% CI 7.5–7.7); $P<0.001$ vs. baseline<br>At 12 months: 7.6% (95% CI 7.6–7.7); $P<0.001$ vs. baseline |
| Eeg-Olofsson et al. 2020 [21]<br>T1D, n=8316; T2D, n=538 | Before vs. after FGMS use on HbA1c (method of measurement not specified) | T1D: 8.1% at baseline. Mean change −0.33% (95% CI −0.36 to −0.31); $P<0.0001$<br>T2D: 8.6% at baseline. Mean change −0.52% (95% CI −0.63 to −0.40); $P<0.0001$ |
| Evans et al. 2020 [22]<br>Meta-analysis of 29 studies; n=1723 with T1D or T2D | FGMS use on laboratory HbA1c | In adults at 2–4 months: mean change −0.56% (95% CI −0.76 to −0.36)<br>In children and adolescents at 2–4 months: mean change −0.54% (95% CI −0.84 to −0.23) |
| Ish-Shalom et al. 2016 [23]<br>T1D, n=6; T2D, n=25 | FGMS use on HbA1c (method of measurement not specified) | In patients with HbA1c ≥ 7.5%<br>At 8 weeks: mean change −1.33 ± 0.29%; $P<0.0001$<br>At 24 weeks: mean change −1.21 ± 0.42%; $P=0.009$ |
| Dunn et al. 2018 [24]<br>n>50,000 | ↑ Scanning frequency on estimated HbA1c | Highest (48.1 scans/day) vs. lowest (4.4 scans/day) scan rate group:<br>6.7% (95% CI 6.7–6.8) vs. 8.0% (95% CI 7.9–8.0; $P<0.001$ |
| Gomez-Peralta et al. 2020 [26]<br>n=22,949 | ↑ Scanning frequency on estimated HbA1c | Highest (39.6 scans/day) vs. lowest (3.9 scans/day) scan rate group:<br>6.9% (95% CI 6.9–7.0) vs. 8.0% (95% CI 8.0–8.1); $P<0.001$ |
| Calliari et al. 2020 [27]<br>Brazil: 17,691 readers and 147,166 sensors<br>Worldwide: 688,640 readers and 7,329,052 sensors | ↑ Scanning frequency on estimated HbA1c | Brazil: Highest (43.1 scans/day) vs. lowest (3.6 scans/day) scan rate group:<br>6.7% (95% CI 6.6–6.8) vs. 7.6% (95% CI 7.4–7.7); $P<0.01$<br>Worldwide: Highest (37.8 scans/day) vs. lowest (3.4 scans/day) scan rate group:<br>6.7% (95% CI 6.7–6.7) vs. 8.1% (95% CI 8.1–8.2); $P<0.01$ |
| BG levels are presented as mg/dL, which can be converted to mmol/L by multiplying values by 0.05551.<br>BG, blood glucose; FGMS, flash glucose monitoring system; HbA1c, glycosylated hemoglobin; T1D, type 1 diabetes; T2D, type 2 diabetes; ↑ indicates increased. | | |

FIG. 17B

| Study | Effect of | Time spent in hypoglycemia | Time spent in hyperglycemia | Time in range |
|---|---|---|---|---|
| Dunn et al. 2018 [24] n>50,000 | ↑ Scanning frequency: 48.1 highest and 4.4 lowest scans/day (mean 16.3 scans/day) | Highest vs. lowest scan rate group: BG <70 mg/dL: ↓ 15%; 79.3 vs. 93.4 min/day; $P<0.001$ BG <56 mg/dL: ↓ 40%; 26.2 vs. 43.4 min/day; $P<0.001$ BG <45 mg/dL: ↓ 49%; 11.9 vs. 23.4 min/day; $P<0.001$ | Highest vs. lowest scan rate group: BG >180 mg/dL: ↓ 44%; 5.9 vs. 10.5 hours/day; $P<0.001$ | Highest vs. lowest scan rate group: BG 70–180 mg/dL: ↑ 40%; 16.8 vs. 12.0 hours/day; $P<0.001$ |
| Jangam et al. 2019 [25] Hypoglycemia n=2,268 or hyperglycemia n=2,268 | Comparison between first and last 14-day periods of sensor wear[a], after stratification of results based on risk of hypoglycemia or hyperglycemia and scanning frequency[b] | High-risk hypoglycemia group (BG ≤ 70 mg/dL): ↓ 19.5% from 200 ± 3 to 161 ± 5 min/day in higher-frequency scanners (mean 20.3 scans/day); $P<0.0001$ ↓ 24.5% from 196 ± 3 to 148 ± 4 min/day in medium-frequency scanners (mean 11.6 scans/day); $P<0.0001$ ↓ 24.5% from 204 ± 3 to 154 ± 4 min/day in low-frequency scanners (mean 7 scans/day); $P<0.0001$ | High-risk hyperglycemia group (BG >240 mg/dL): ↓ 14.2% from 5.7 ± 0.10 to 4.9 ± 0.14 hours/day in higher-frequency scanners (mean 18.1 scans/day); $P<0.0001$ ↓ 6.3% from 5.8 ± 0.09 to 5.5 ± 0.13 hours/day in medium-frequency scanners (mean 10.5 scans/day); $P=0.02$ No effect in low-frequency scanners (mean 6.2 scans/day) | |
| Gomez-Peralta et al. 2020 [26] n=22,949 | ↑ Scanning frequency: 39.6 highest and 3.9 lowest scans/day (mean 13 scans/day) | Highest vs. lowest scan rate group: BG <70 mg/dL: ↓ 14%; 85.3 (95% CI 79.3–91.2) vs. 99.2 (95% CI 93.9–104.4) min/day; $P<0.001$ BG <54 mg/dL: ↓ 37%; 29.7 (95% CI 26.6–32.8) vs. 46.8 (95% CI 43.6–49.9) min/day; $P<0.001$ | Highest vs. lowest scan rate group: BG >180 mg/dL: ↓ 37%; 6.9 (95% CI 6.7–7.2) vs. 10.9 (95% CI 10.6–11.2) hours/day; $P<0.001$ | Highest vs. lowest scan rate group: BG 70–180 mg/dL: ↑ 36%; 15.6 (95% CI 15.4–15.9) vs. 11.5 (95% CI 11.2–11.7) hours/day; $P<0.001$ |
| Calliari et al. 2020 [27] Brazil: 17,691 readers and 147,166 sensors Worldwide: 688,640 readers and 7,329,052 sensors | ↑ Scanning frequency Brazil: 43.1 highest and 3.6 lowest scans/day (average 14 scans/day) Worldwide: 37.8 highest and 3.4 lowest scans/day (average 12 scans/day) | Highest vs. lowest scan rate group (BG <54 mg/dL): Brazil: 27.1 (95% CI 23.8–30.5) vs. 28.3 (95% CI 25.0–31.5) min/day; $P=0.64$ Worldwide: 22.9 (95% CI 22.5–23.4) vs. 31.1 (95% CI 30.6–31.6) min/day; $P<0.01$ | Highest vs. lowest scan rate group (BG >180 mg/dL): Brazil: 6.0 (95% CI 5.7–6.3) vs. 8.7 (95% CI 8.3–9.1) hours/day; $P<0.01$ Worldwide: 5.8 (95% CI 5.8–5.9) vs. 10.8 (95% CI 10.7–10.8) hours/day; $P<0.01$ | Highest vs. lowest scan rate group (BG 70–180 mg/dL): Brazil:16.6 vs. 14.2 hours/day; $P<0.01$ Worldwide: 17.0 vs. 12.1 hours/day; $P<0.01$ |

BG levels are presented as mg/dL, which can be converted to mmol/L by multiplying values by 0.05551.
[a] Scanning frequency decreased gradually from >18 scans/day during first sensor use to ≈ 15 scans/day at 2 months, and was maintained at the lower level for the remainder of the 6-month analysis period.
[b] Glucose results were analyzed after being divided into high, medium and low-risk groups based on tertiles of time spent in hypoglycemia (min/day <70 mg/dL) or hyperglycemia (hours/day >240 mg/dL), and further subdivision into tertiles of glucose scanning frequency (high, medium, low).
BG, blood glucose; CI, confidence interval; ↑ indicates increased; ↓ indicates decreased/reduced.

FIG. 17C

SYSTEMS, DEVICES, AND METHODS OF ANALYTE MONITORING

CROSS-REFERENCE TO RELATED APPLICATIONS

This application claims priority to and the benefit of U.S. Provisional Patent Application No. 63/029,339, filed May 22, 2020, U.S. Provisional Patent Application No. 63/034,118, filed Jun. 3, 2020, and U.S. Provisional Patent Application No. 63/080,763, filed Sep. 20, 2020, which are incorporated by reference herein in their entirety for all purposes.

FIELD

The subject matter described herein relates generally to improved analyte monitoring systems, as well as methods and devices relating thereto.

BACKGROUND

The detection and/or monitoring of analyte levels, such as glucose, ketones, lactate, oxygen, hemoglobin A1C, albumin, alcohol, alkaline phosphatase, alanine transaminase, aspartate aminotransferase, bilirubin, blood urea nitrogen, calcium, carbon dioxide, chloride, creatinine, hematocrit, lactate, magnesium, oxygen, pH, phosphorus, potassium, sodium, total protein, uric acid, etc., or the like, can be important to the health of an individual having diabetes. Patients suffering from diabetes mellitus can experience complications including loss of consciousness, cardiovascular disease, retinopathy, neuropathy, and nephropathy. Diabetics are generally required to monitor their glucose levels to ensure that they are being maintained within a clinically safe range, and may also use this information to determine if and/or when insulin is needed to reduce glucose levels in their bodies, or when additional glucose is needed to raise the level of glucose in their bodies.

Growing clinical data demonstrates a strong correlation between the frequency of glucose monitoring and glycemic control. Despite such correlation, however, many individuals diagnosed with a diabetic condition do not monitor their glucose levels as frequently as they should due to a combination of factors including convenience, testing discretion, pain associated with glucose testing, and cost.

To increase patient adherence to a plan of frequent glucose monitoring, in vivo analyte monitoring systems can be utilized, in which a sensor control device may be worn on the body of an individual who requires analyte monitoring. To increase comfort and convenience for the individual, the sensor control device may have a small form-factor and can be applied by the individual with a sensor applicator. The application process includes inserting at least a portion of a sensor that senses a user's analyte level in a bodily fluid located in a layer of the human body, using an applicator or insertion mechanism, such that the sensor comes into contact with a bodily fluid. The sensor control device may also be configured to transmit analyte data to another device, from which the individual, her health care provider ("HCP"), or a caregiver can review the data and make therapy decisions.

Despite their advantages, however, some people are reluctant to use analyte monitoring systems for various reasons, including the complexity and volume of data presented, a learning curve associated with the software and user interfaces for analyte monitoring systems, and an overall paucity of actionable information presented.

Thus, needs exist for analyte monitoring systems, as well as methods and devices relating thereto, for improving clinical outcomes.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to systems, devices, and methods of analyte monitoring and benefits thereof. According to some embodiments, a glucose monitoring system can include a sensor control device comprising an analyte sensor coupled with sensor electronics, the sensor control device configured to transmit data indicative of an analyte level and a reader device comprising a wireless communication circuitry configured to receive the data indicative of the analyte level, and one or more processors coupled with a memory. The memory can be configured to store instructions that, when executed by the one or more processors, cause the one or more processors to determine a frequency of interaction over a first time period based on one or more instances of user operation of the reader device, and output a first notification if the determined frequency of interaction is below a predetermined target level of interaction and output a second notification if the determined frequency of interaction is above the predetermined target level of interaction, wherein below the predetermined target level of interaction, an increase in the determined frequency of interaction corresponds to a first improvement in a metabolic parameter, and above the predetermined target level of interaction, an increase in the determined frequency of interaction corresponds to a second improvement in the metabolic parameter. The first improvement can be greater than the second improvement.

According to embodiments, the user operation of the reader device can include a user view of a current analyte level. According to embodiments, user operation of the reader device can include a user scan of the data processing unit with the reader device.

According to embodiments, the metabolic parameter is HbA1c. In some embodiments, the instructions, when executed by the one or more processors, can cause the one or more processors to output the first notification and second notification if HbA1c is at or above a predetermined level. According to embodiments, the first improvement can be a reduction in HbA1c of 0.02-0.12% per user operation of the reader device. According to embodiments, the second improvement can be a reduction in HbA1c of at least 0.03% per user operation of the reader device.

According to embodiments, the metabolic parameter is time spent in hypoglycemia. In some embodiments, the predetermined target level of interaction is 8 scans per day.

According to embodiments, the metabolic parameter is time in target range. In some embodiments, the instructions, when executed by the one or more processors, can cause the one or more processors to output the first notification and second notification if the time in target range is at or below a predetermined level. According to embodiments, the first improvement can be an increase in time in target range of 3-19 minutes per day per user operation of the reader device. According to embodiments, the second improvement can be an increase in time in target range of approximately at least 7 minutes per user operation of the reader device.

According to embodiments, the predetermined target level of interaction can be 14 scans per day. The predetermined target level of interaction can be user-determined. The predetermined target level of interaction can be determined by a health care provider. According to embodiments, the predetermined target level of is intelligently determined using machine learning.

According to embodiments, the first time period can be 1, 2, 3, 4, 5, 6, or more days. The first time period can be 1, 2, 3, 4, 5, 6, or more weeks. The first time period can be a date range. The first time period can be 30 days. The first time period can be 90 days. The first time period can be 1, 2, 3, or more months.

According to embodiments, the first time period can include one or more second time periods, and the instructions, when executed by the one or more processors, can cause the one or more processors to record no more than one instance of user operation of the reader device during each second time period. The one or more second time periods can be an increment of one hour and the first time period is one day.

According to embodiments, the first notification and the second notification can include a visual notification. The first notification and the second notification can include an audio notification. The first notification can be an alert. The second notification can be a prompt.

In accordance with the disclosed subject matter, a glucose monitoring system is also provided. The system includes a sensor control device comprising an analyte sensor coupled with sensor electronics, the sensor control device configured to transmit data indicative of an analyte level, and a reader device comprising wireless communication circuitry configured to receive the data indicative of the analyte level, and one or more processors coupled with a memory. The memory can be configured to store instructions that, when executed by the one or more processors, cause the one or more processors to: record a time corresponding to a first user operation of the reader device, record a time corresponding to a second user operation of the reader device, wherein the second user operation c after the first user operation, calculate a time elapsed between the first user operation and the second user operation, determine a frequency of interaction over a time period based on user operation of the reader device; and output a notification if the calculated time elapsed is equal to or greater than a predetermined time period, wherein the notification is an alert if the determined frequency of interaction is below a predetermined target level of interaction and a prompt if the determined frequency of interaction is above the predetermined target level of interaction.

According to embodiments, a glucose monitoring system can include a sensor control device comprising an analyte sensor coupled with sensor electronics, the sensor control device configured to transmit data indicative of an analyte level, and a reader device comprising wireless communication circuitry configured to receive the data indicative of the analyte level, and one or more processors coupled with a memory. The memory can be configured to store instructions that, when executed by the one or more processors, cause the one or more processors to: record a time corresponding to a user interaction with the reader device, calculate a time elapsed from the user interaction to a current time, and output a notification for a subsequent user interaction corresponding to a determined frequency of interaction.

According to embodiments, the notification comprises displaying a current analyte concentration value. In some embodiments, the notification is output if a second user interaction is not recoded in the calculated time elapsed.

According to embodiments, the predetermined time period can be programmable.

Many of the embodiments provided herein are improved GUIs or GUI features for analyte monitoring systems that are highly intuitive, user-friendly, and provide for rapid access to physiological information of a user. More specifically, these embodiments allow a user to easily navigate through and between different user interfaces that can quickly indicate to the user various physiological conditions and/or actionable responses, without requiring the user (or an HCP) to go through the arduous task of examining large volumes of analyte data. Furthermore, some of the GUIs and GUI features, such as the sensor usage interfaces, allow for users (and their caregivers) to better understand and improve their respective levels of engagement with their analyte monitoring systems. Likewise, many other embodiments provided herein comprise improved digital interfaces and/or features for analyte monitoring systems that improve upon: the accuracy and integrity of the analyte data being collected by the analyte monitoring system by allowing for data backfilling, flexibility of the analyte monitoring system by allowing users to transition between different reader devices, alarming functionality of the analyte monitoring system by providing for more robust inter-device communications during certain adverse conditions, to name only a few. Other improvements and advantages are provided as well. The various configurations of these devices are described in detail by way of the embodiments which are only examples.

Other systems, devices, methods, features and advantages of the subject matter described herein will be or will become apparent to one with skill in the art upon examination of the following figures and detailed description. It is intended that all such additional systems, devices, methods, features, and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 2D to 2I are example embodiments of GUIs comprising sensor results interfaces.

FIGS. 5C to 5F are example embodiments of report GUIs including sensor usage information.

FIGS. 8C to 8E are graphs depicting data at various stages of processing according to an example embodiment of a method for data merging in an analyte monitoring system.

FIGS. 13A-13K show the result of an exemplary study which analyses reduction in HbA1c levels associated with use of continuous glucose monitoring.

FIGS. 14A-14I show an example study which analyses collected glucose data.

FIGS. 15A-15E show an example study which analyses patients with type 2 diabetes mellitus treated with multiple daily injection therapy FIGS. 16A-16I show an example study of certain effects of FLASH glucose monitoring systems.

FIGS. 17A-17C show the results of a meta-analysis of various studies which indicate improvement in several glycemic parameters in users with a continuous glucose monitor system.

DETAILED DESCRIPTION

Figure 1:
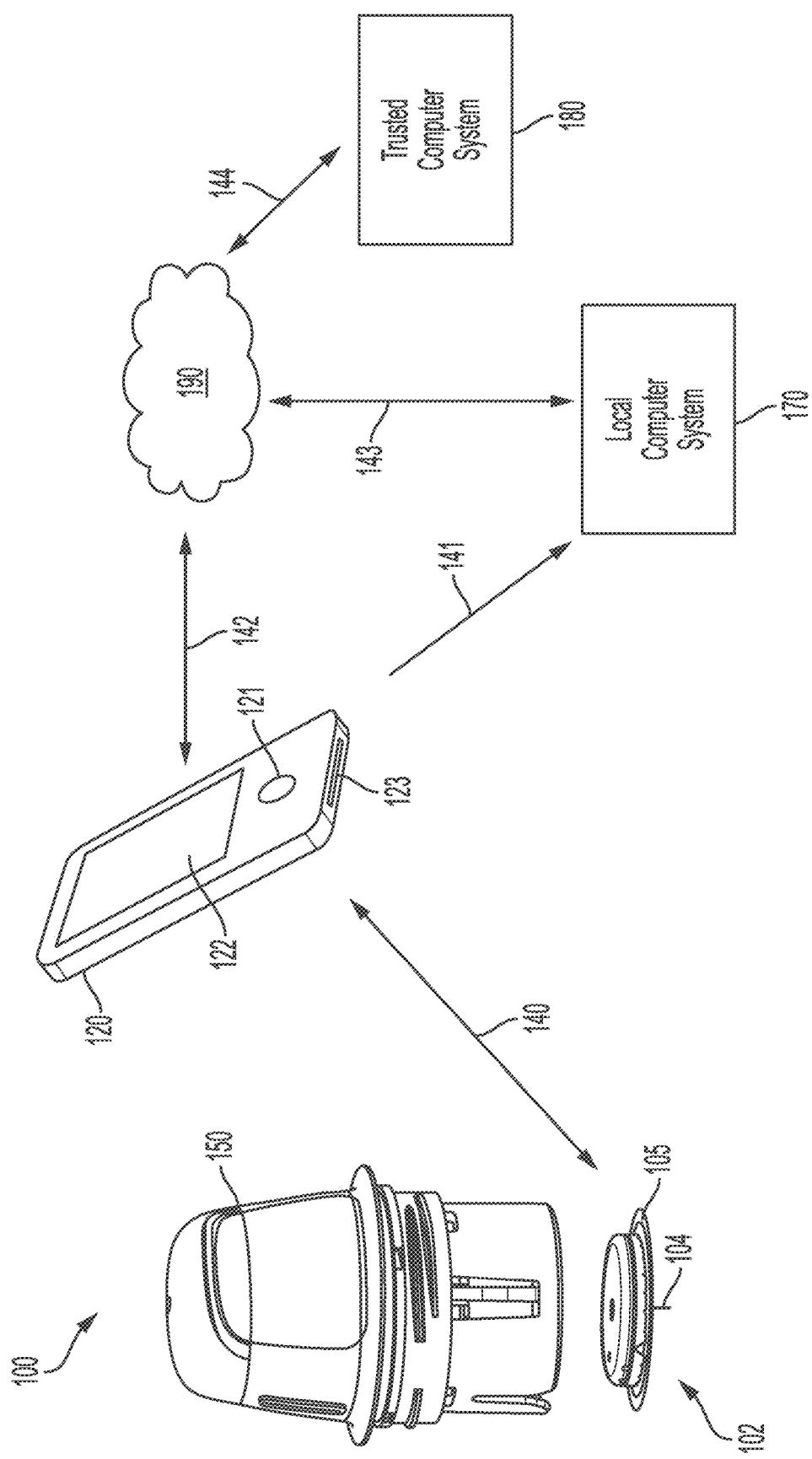
FIG. 1 is a system overview of an analyte monitoring system comprising a sensor applicator, a sensor control device, a reader device, a network, a trusted computer system, and a local computer system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of this disclosure will be limited only by the appended claims.

As used herein and in the appended claims, the singular forms "a," "an," and "the" include plural referents unless the context clearly dictates otherwise.

The publications discussed herein are provided solely for their disclosure prior to the filing date of this application. Nothing herein is to be construed as an admission that this disclosure is not entitled to antedate such publication by virtue of prior disclosure. Further, the dates of publication provided may be different from the actual publication dates which may need to be independently confirmed.

Generally, embodiments of this disclosure include GUIs and digital interfaces for analyte monitoring systems, and methods and devices relating thereto. Accordingly, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of this disclosure. For example, embodiments of sensor control devices, reader devices, local computer systems, and trusted computer systems are disclosed, and these devices and systems can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps.

As previously described, a number of embodiments described herein provide for improved GUIs for analyte monitoring systems, wherein the GUIs are highly intuitive, user-friendly, and provide for rapid access to physiological information of a user. According to some embodiments, a Time-in-Ranges GUI of an analyte monitoring system is provided, wherein the Time-in-Ranges GUI comprises a plurality of bars or bar portions, wherein each bar or bar portion indicates an amount of time that a user's analyte level is within a predefined analyte range correlating with the bar or bar portion. According to another embodiment, an Analyte Level/Trend Alert GUI of an analyte monitoring system is provided, wherein the Analyte Level/Trend Alert GUI comprises a visual notification (e.g., alert, alarm, pop-up window, banner notification, etc.), and wherein the visual notification includes an alarm condition, an analyte level measurement associated with the alarm condition, and a trend indicator associated with the alarm condition. In sum, these embodiments provide for a robust, user-friendly interfaces that can increase user engagement with the analyte monitoring system and provide for timely and actionable responses by the user, to name a few advantages.

In addition, a number of embodiments described herein provide for improved digital interfaces for analyte monitoring systems. According to some embodiments, improved methods, as well as systems and device relating thereto, are provided for data backfilling, aggregation of disconnection and reconnection events for wireless communication links, expired or failed sensor transmissions, merging data from multiple devices, transitioning of previously activated sensors to new reader devices, generating sensor insertion failure system alarms, and generating sensor termination system alarms. Collectively and individually, these digital interfaces improve upon the accuracy and integrity of analyte data being collected by the analyte monitoring system, the flexibility of the analyte monitoring system by allowing users to transition between different reader devices, and the alarming capabilities of the analyte monitoring system by providing for more robust inter-device communications during certain adverse conditions, to name only a few. Other improvements and advantages are provided as well. The various configurations of these devices are described in detail by way of the embodiments which are only examples.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

Example Embodiment of In Vivo Analyte Monitoring System

FIG. 1 is a conceptual diagram depicting an example embodiment of an analyte monitoring system 100 that includes a sensor applicator 150, a sensor control device 102, and a reader device 120. Here, sensor applicator 150 can be used to deliver sensor control device 102 to a monitoring location on a user's skin where a sensor 104 is maintained in position for a period of time by an adhesive patch 105. Sensor control device 102 is further described in FIGS. 2B and 2C, and can communicate with reader device 120 via a communication path 140 using a wired or wireless technique. Example wireless protocols include Bluetooth, Bluetooth Low Energy (BLE, BTLE, Bluetooth SMART, etc.), Near Field Communication (NFC) and others. Users can view and use applications installed in memory on reader device 120 using screen 122 (which, in many embodiments, can comprise a touchscreen), and input 121. A device battery of reader device 120 can be recharged using power port 123. While only one reader device 120 is shown, sensor control device 102 can communicate with multiple reader devices 120. Each of the reader devices 120 can communicate and share data with one another. More details about reader device 120 is set forth with respect to FIG. 2A below. Reader device 120 can communicate with local computer system 170 via a communication path 141 using a wired or wireless communication protocol. Local computer system 170 can include one or more of a laptop, desktop, tablet, phablet, smartphone, set-top box, video game console, or other computing device and wireless communication can include any of a number of applicable wireless networking protocols including Bluetooth, Bluetooth Low Energy (BTLE), Wi-Fi or others. Local computer system 170 can communicate via communications path 143 with a network 190 similar to how reader device 120 can communicate via a communications path 142 with network 190, by a wired or wireless communication protocol as described previously. Network 190 can be any of a number of networks, such as private networks and public networks, local area or wide area networks, and so forth. A trusted computer system 180 can include a cloud-based platform or server, and can provide for authentication services, secured data storage, report generation, and can communicate via communications path 144 with network 190 by wired or wireless technique. In addition, although FIG. 1 depicts trusted computer system 180 and local computer system 170 communicating with a single sensor control device 102 and a single reader device 120, it will be appreciated by those of skill in the art that local computer system 170 and/or trusted computer system 180 are each capable of being in wired or wireless communication with a plurality of reader devices and sensor control devices.

Additional details of suitable analyte monitoring devices, systems, methods, components and the operation thereof along with related features are set forth in U.S. Pat. No. 9,913,600 to Taub et. al., International Publication No. WO2018/136898 to Rao et. al., International Publication No. WO2019/236850 to Thomas et. al., and U.S. Patent Publication No. 2020/01969191 to Rao et al., each of which is incorporated by reference in its entirety herein.

Example Embodiment of Reader Device

Figure 2A:
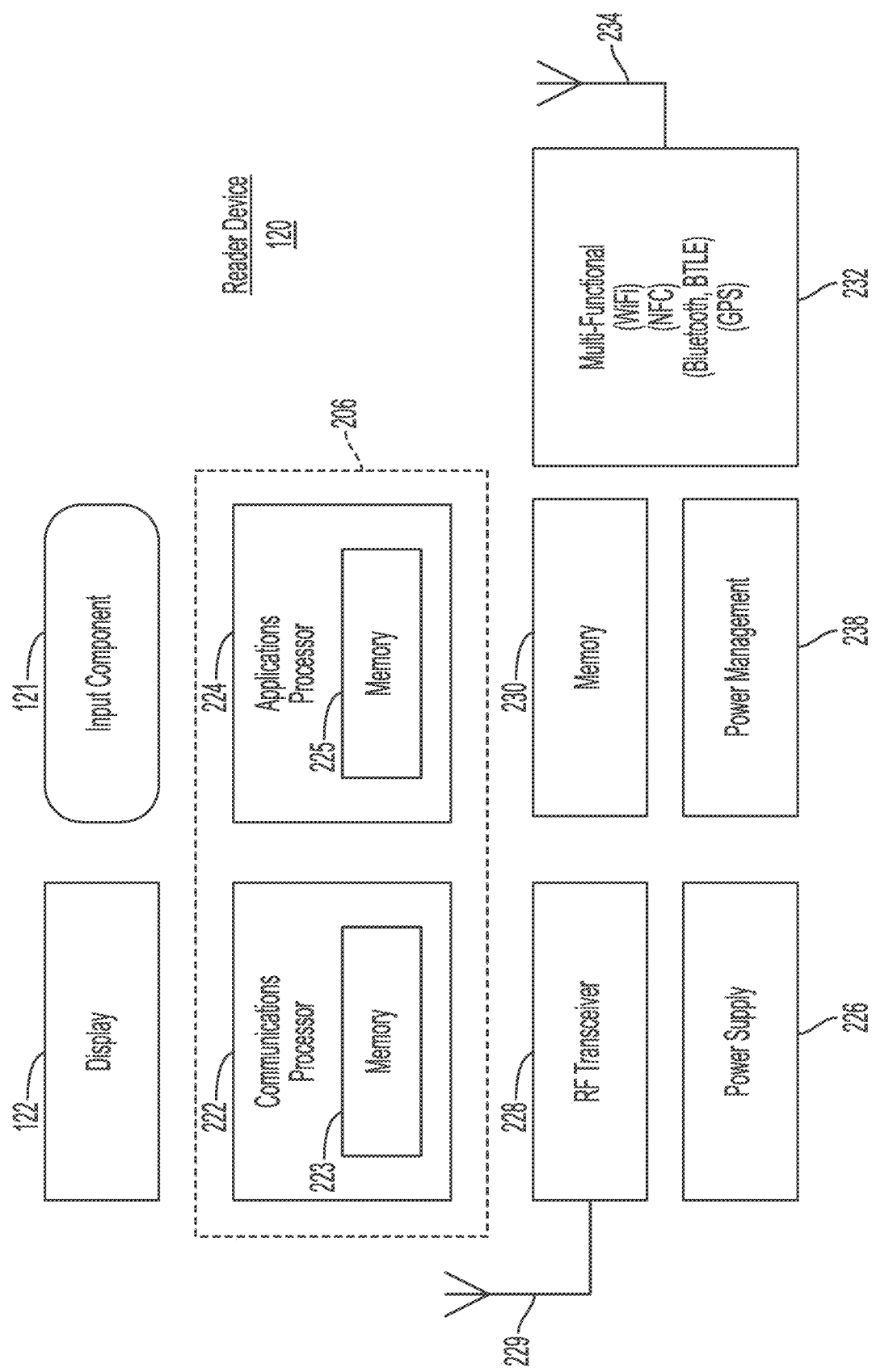
FIG. 2A is a block diagram depicting an example embodiment of a reader device.

FIG. 2A is a block diagram depicting an example embodiment of a reader device 120, which, in some embodiments, can comprise a smart phone or a smart watch. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Further, reader device 120 can also include a multi-functional transceiver 232, which can comprise wireless communication circuitry, and which can be configured to communicate over Wi-Fi, NFC, Bluetooth, BTLE, and GPS with one or more antenna 234. As understood by one of skill in the art, these components are electrically and communicatively coupled in a manner to make a functional device.

Example Embodiments of Sensor Control Devices

Figure 2B:
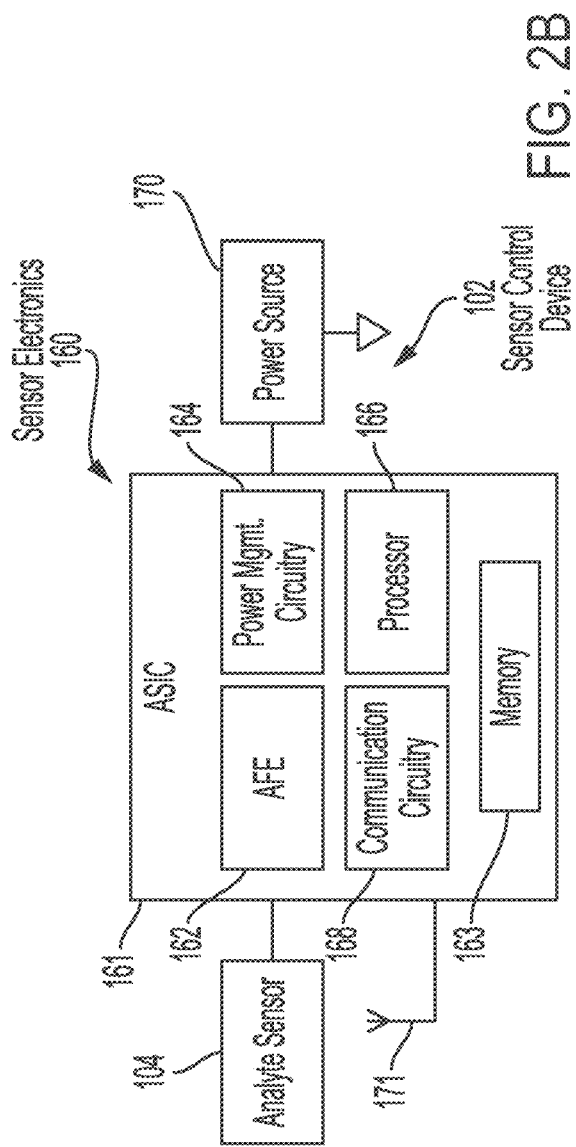
FIGS. 2B and 2C are block diagrams depicting example embodiments of sensor control devices.
Figure 2C:
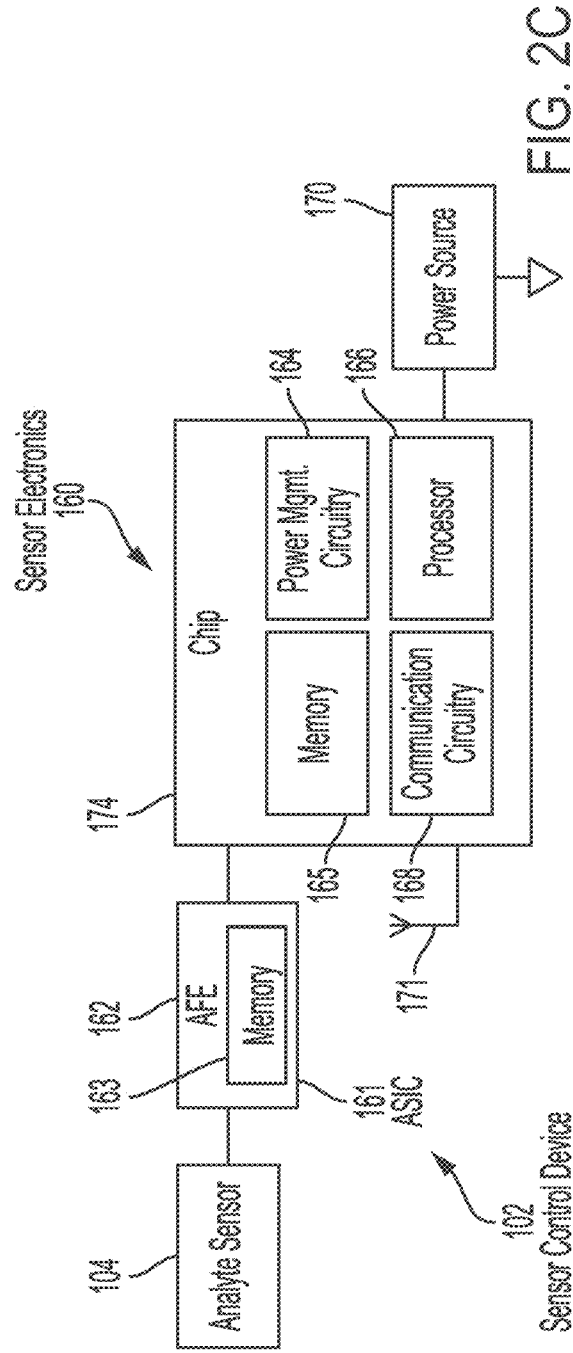

FIGS. 2B and 2C are block diagrams depicting example embodiments of sensor control devices 102 having analyte sensors 104 and sensor electronics 160 (including analyte monitoring circuitry) that can have the majority of the processing capability for rendering end-result data suitable for display to the user. In FIG. 2B, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 170, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to reader device 120 (not shown), for example, where minimal further processing is needed by the resident software application to display the data. According to some embodiments, for example, a current glucose value can be transmitted from sensor control device 102 to reader device 120 every minute, and historical glucose values can be transmitted from sensor control device 102 to reader device 120 every five minutes.

In some embodiments, to conserve power and processing resources on sensor control device 102, digital data received from AFE 162 can be sent to reader device 120 (not shown) with minimal or no processing. In still other embodiments, processor 166 can be configured to generate certain predetermined data types (e.g., current glucose value, historical glucose values) either for storage in memory 163 or transmission to reader device 120 (not shown), and to ascertain certain alarm conditions (e.g., sensor fault conditions), while other processing and alarm functions (e.g., high/low glucose threshold alarms) can be performed on reader device 120. Those of skill in the art will understand that the methods, functions, and interfaces described herein can be performed—in whole or in part—by processing circuitry on sensor control device 102, reader device 120, local computer system 170, or trusted computer system 180.

FIG. 2C is similar to FIG. 2B but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 may include memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Example Embodiments of Graphical User Interfaces for Analyte Monitoring Systems

Described herein are example embodiments of GUIs for analyte monitoring systems. As an initial matter, it will be understood by those of skill in the art that the GUIs described herein comprise instructions stored in a memory of reader device 120, local computer system 170, trusted computer system 180, and/or any other device or system that is part of, or in communication with, analyte monitoring system 100. These instructions, when executed by one or more processors of the reader device 120, local computer system 170, trusted computer system 180, or other device or system of analyte monitoring system 100, cause the one or more processors to perform the method steps and/or output the GUIs described herein. Those of skill in the art will further recognize that the GUIs described herein can be stored as instructions in the memory of a single centralized device or, in the alternative, can be distributed across multiple discrete devices in geographically dispersed locations.

Example Embodiments of Sensor Results Interfaces

FIGS. 2D to 2I depict example embodiments of sensor results interfaces or GUIs for analyte monitoring systems. In accordance with the disclosed subject matter, the sensor results GUIs described herein are configured to display analyte data and other health information through a user interface application (e.g., software) installed on a reader device, such as a smart phone or a receiver, like those described with respect to FIG. 2B. Those of skill in the art will also appreciate that a user interface application with a sensor results interface or GUI can also be implemented on a local computer system or other computing device (e.g., wearable computing devices, smart watches, tablet computer, etc.).

Referring first to FIG. 2D, sensor results GUI 235 depicts an interface comprising a first portion 236 that can include a numeric representation of a current analyte concentration value (e.g., a current glucose value), a directional arrow to indicate an analyte trend direction, and a text description to provide contextual information such as, for example, whether the user's analyte level is in range (e.g., "Glucose in Range"). First portion 236 can also comprise a color or shade that is indicative of an analyte concentration or trend. For example, as shown in FIG. 2D, first portion 236 is a green shade, indicating that the user's analyte level is within a target range. According to some embodiments, for example, a red shade can indicate an analyte level below a low analyte level threshold, an orange shade can indicate an analyte level above a high analyte level threshold, and an yellow shade can indicate an analyte level outside a target range. In addition, according to some embodiments, sensor results GUI 235 also includes a second portion 237 comprising a graphical representation of analyte data. In particular, second portion 237 includes an analyte trend graph reflecting an analyte concentration, as shown by the y-axis, over a predetermined time period, as shown by the x-axis. In some embodiments, the predetermined time period can be shown in five-minute increments, with a total of twelve hours of data. Those of skill in the art will appreciate, however, that other time increments and durations of analyte data can be utilized and are fully within the scope of this disclosure. Second portion 237 can also include a point 239 on the analyte trend graph to indicate the current analyte concentration value, a shaded green area 240 to indicate a target analyte range, and two dotted lines 238*a* and 238*b* to indicate, respectively, a high analyte threshold and a low analyte threshold. According to some embodiments, GUI 235 can also include a third portion 241 comprising a graphical indicator and textual information representative of a remaining amount of sensor life.

Referring next to FIG. 2E, another example embodiment of a sensor results GUI 245 is depicted. In accordance with the disclosed subject matter, first portion 236 is shown in a yellow shade to indicate that the user's current analyte concentration is not within a target range. In addition, second portion 237 includes: an analyte trend line 241 which can reflect historical analyte levels over time and a current analyte data point 239 to indicate the current analyte concentration value (shown in yellow to indicate that the current value is outside the target range).

According to another aspect of the embodiments, data on sensor results GUI 245 is automatically updated or refreshed according to an update interval (e.g., every second, every minute, every 5 minutes, etc.). For example, according to many of the embodiments, as analyte data is received by the reader device, sensor results GUI 245 will update: (1) the current analyte concentration value shown in first portion 236, and (2) the analyte trend line 241 and current analyte data point 239 show in second portion 237. Furthermore, in some embodiments, the automatically updating analyte data can cause older historical analyte data (e.g., in the left portion of analyte trend line 241) to no longer be displayed.

FIG. 2F is another example embodiment of a sensor results GUI 250. According to the depicted embodiment, sensor results GUI 250 includes first portion 236 which is shown in an orange shade to indicate that the user's analyte levels are above a high glucose threshold (e.g., greater than 250 mg/dL). Sensor results GUI 250 also depicts health information icons 251, such as an exercise icon or an apple icon, to reflect user logged entries indicating the times when the user had exercised or eaten a meal.

FIG. 2G is another example embodiment of a sensor results GUI 255. According to the depicted embodiments, sensor results GUI 255 includes first portion 236 which is also shown in an orange shade to indicate that the user's analyte levels are above a high glucose threshold. As can be seen in FIG. 2G, first portion 236 does not report a numeric value but instead displays the text "HI" to indicate that the current analyte concentration value is outside a glucose reporting range high limit. Although not depicted in FIG. 2G, those of skill in the art will understand that, conversely, an analyte concentration below a glucose reporting range low limit will cause first portion 236 not to display a numeric value, but instead, the text "LO".

FIG. 2H is another example embodiment of a sensor results GUI 260. According to the depicted embodiments, sensor results GUI 260 includes first portion 236 which is shown in a green shade to indicate that the user's current analyte level is within the target range. In addition, according to the depicted embodiments, first portion 236 of GUI 260 includes the text, "GLUCOSE GOING LOW," which can indicate to the user that his or her analyte concentration value is predicted to drop below a predicted low analyte level threshold within a predetermined amount of time (e.g., predicted glucose will fall below 75 mg/dL within 15 minutes). Those of skill in the art will understand that if a user's analyte level is predicted to rise above a predicted high analyte level threshold within a predetermined amount of time, sensor results GUI 260 can display a "GLUCOSE GOING HIGH" message.

FIG. 2I is another example embodiment of a sensor results GUI 265. According to the depicted embodiments, sensor results GUI 265 depicts first portion 236 when there is a sensor error. In accordance with the disclosed subject matter, first portion 236 includes three dashed lines 266 in place of the current analyte concentration value to indicate that a current analyte value is not available. In some embodiments, three dashed lines 266 can indicate one or more error conditions such as, for example, (1) a no signal condition; (2) a signal loss condition; (3) sensor too hot/cold condition; or (4) a glucose level unavailable condition. Furthermore, as can be seen in FIG. 2I, first portion 236 comprises a gray shading (instead of green, yellow, orange, or red) to indicate that no current analyte data is available. In addition, according to another aspect of the embodiments, second portion 237 can be configured to display the historical analyte data in the analyte trend graph, even though there is an error condition preventing the display of a numeric value for a current analyte concentration in first portion 236. However, as shown in FIG. 2I, no current analyte concentration value data point is shown on the analyte trend graph of second portion 237.

Example Embodiments of Time-in-Ranges Interfaces

FIGS. 3A to 3F depict example embodiments of GUIs for analyte monitoring systems. In particular, FIGS. 3A to 3F depict Time-in-Ranges (also referred to as Time-in-Range and/or Time-in-Target) GUIs, each of which comprise a plurality of bars or bar portions, wherein each bar or bar portion indicates an amount of time that a user's analyte level is within a predefined analyte range correlating with the bar or bar portion. In some embodiments, for example, the amount of time can be expressed as a percentage of a predefined amount of time.

Figure 3B:
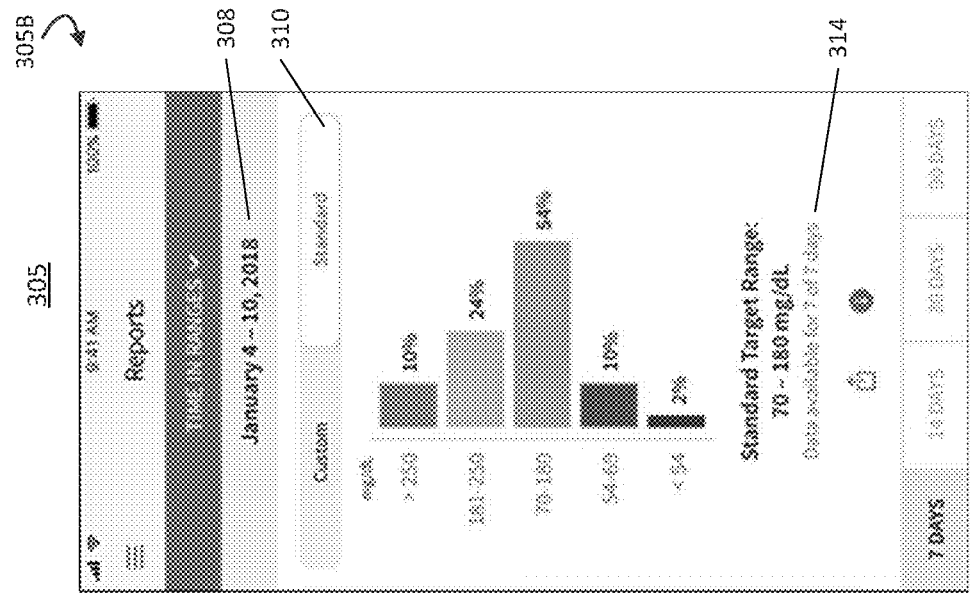
FIGS. 3A to 3F are example embodiments of GUIs comprising time-in-ranges interfaces.
Figure 3A:
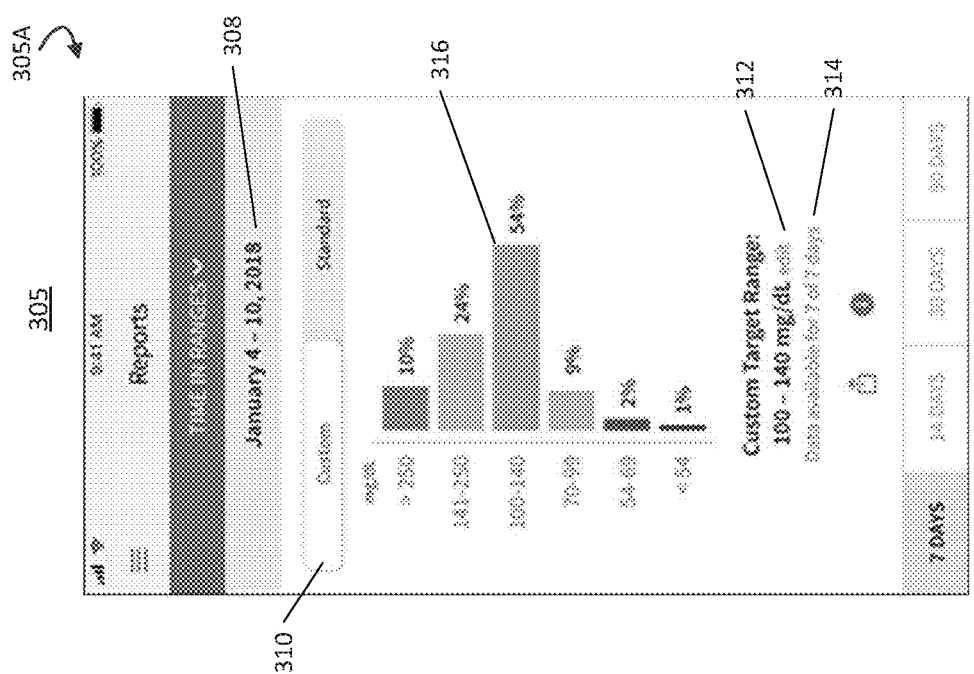

Turning to FIGS. 3A and 3B, an example embodiment of a Time-in-Ranges GUI 305 is shown, wherein Time-in-Ranges GUI 305 comprises a "Custom" Time-in-Ranges view 305A and a "Standard" Time-in-Ranges view 305B, with a slidable element 310 that allows the user to select between the two views. In accordance with the disclosed subject matter, Time-in-Ranges views 305A, 305B can each comprise multiple bars, wherein each bar indicates an amount of time that a user's analyte level is within a predefined analyte range correlating with the bar. In some embodiments, Time-in-Ranges views 305A, 305B further comprise a date range indicator 308, showing relevant dates associated with the displayed plurality of bars, and a data availability indicator 314, showing the period(s) of time in which analyte data is available for the displayed analyte data (e.g., "Data available for 7 of 7 days").

Referring to FIG. 3A, "Custom" Time-in-Ranges view 305A includes six bars comprising (from top to bottom): a first bar indicating that the user's glucose range is above 250 mg/dL for 10% of a predefined amount of time, a second bar indicating that the user's glucose range is between 141 and 250 mg/dL for 24% of the predefined amount of time, a third bar 316 indicating that the user's glucose range is between 100 and 140 mg/dL for 54% of the predefined amount of time, a fourth bar indicating that the user's glucose range is between 70 and 99 mg/dL for 9% of the predefined amount of time, a fifth bar indicating that the user's glucose range is between 54 and 69 mg/dL for 2% of the predefined amount of time, and a sixth bar indicating that the user's glucose range is less than 54 mg/dL for 1% of the predefined amount of time. Those of skill in the art will recognize that the glucose ranges and percentages of time associated with each bar can vary depending on the ranges defined by the user and the available analyte data of the user. Furthermore, although FIGS. 3A and 3B show a predefined amount of time 314 equal to seven days, those of skill in the art will appreciate that other predefined amounts of time can be utilized (e.g., one day, three days, fourteen days, thirty days, ninety days, etc.), and are fully within the scope of this disclosure.

According to another aspect of the embodiments, "Custom" Time-in-Ranges view 305A also includes a user-definable custom target range 312 that includes an actionable "edit" link that allows a user to define and/or change the custom target range. As shown in "Custom" Time-in-Ranges view 305A, the custom target range 312 has been defined as a glucose range between 100 and 140 mg/dL and corresponds with third bar 316 of the plurality of bars. Those of skill in the art will also appreciate that, in other embodiments, more than one range can be adjustable by the user, and such embodiments are fully within the scope of this disclosure.

Referring to FIG. 3B, "Standard" Time-in-Ranges view 305B includes five bars comprising (from top to bottom): a first bar indicating that the user's glucose range is above 250 mg/dL for 10% of a predefined amount of time, a second bar indicating that the user's glucose range is between 181 and 250 mg/dL for 24% of the predefined amount of time, a third bar indicating that the user's glucose range is between 70 and 180 mg/dL for 54% of the predefined amount of time, a fourth bar indicating that the user's glucose range is between 54 and 69 mg/dL for 10% of the predefined amount of time, and a fifth bar indicating that the user's glucose range is less than 54 mg/dL for 2% of the predefined amount of time. As with the "Custom" Time-in-Ranges view 305A, those of skill in the art will recognize that the percentages of time associated with each bar can vary depending on the available analyte data of the user. Unlike the "Custom" Time-in-Ranges view 305A, however, the glucose ranges shown in "Standard" view 305B cannot be adjusted by the user.

Figure 3D:
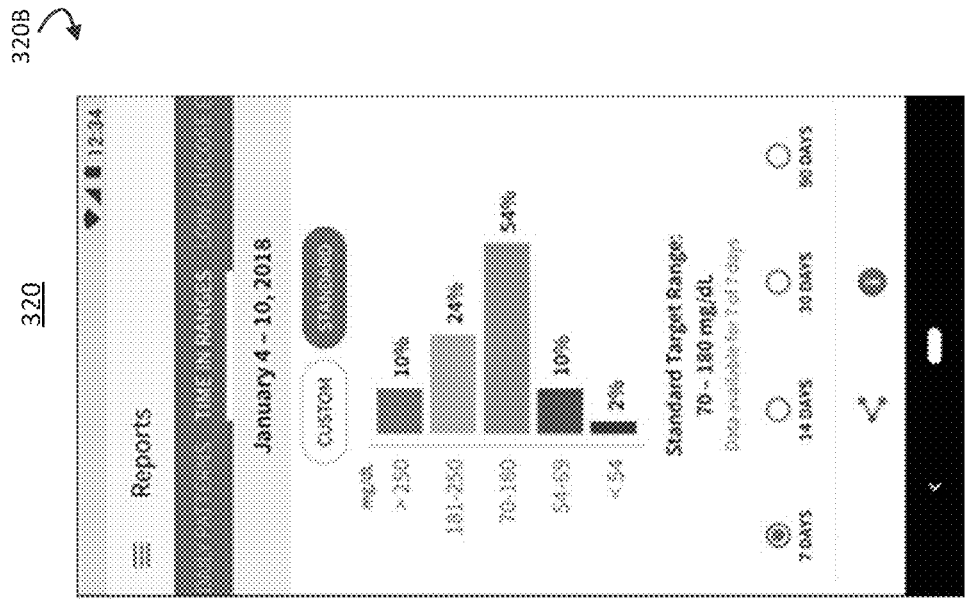
Figure 3C:
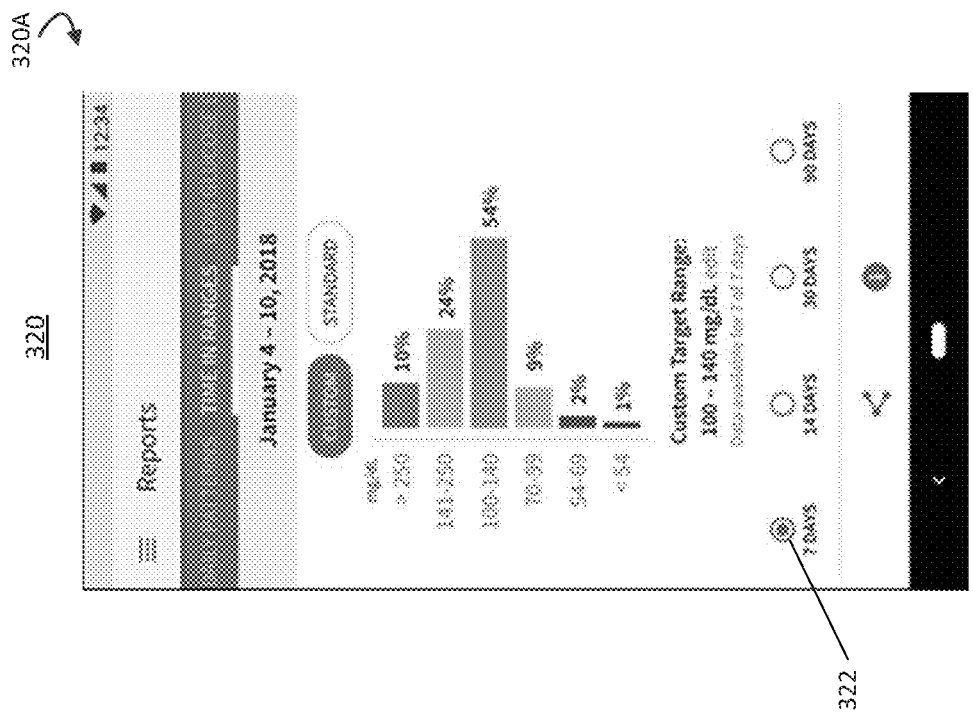

FIGS. 3C and 3D depict another example embodiment of Time-in-Ranges GUI 320 with multiple views, 320A and 320B, which are analogous to the views shown in FIGS. 3A and 3B, respectively. According to some embodiments, Time-in-Ranges GUI 320 can further include one or more selectable icons 322 (e.g., radio button, check box, slider, switch, etc.) that allow a user to select a predefined amount of time over which the user's analyte data will be shown in the Time-in-Range GUI 320. For example, as shown in FIGS. 3C and 3D, selectable icons 322 can be used to select a predefined amount of time of seven days, fourteen days, thirty days, or ninety days. Those of skill in the art will appreciate that other predefined amounts of time can be utilized and are fully within the scope of this disclosure.

Figure 3F:
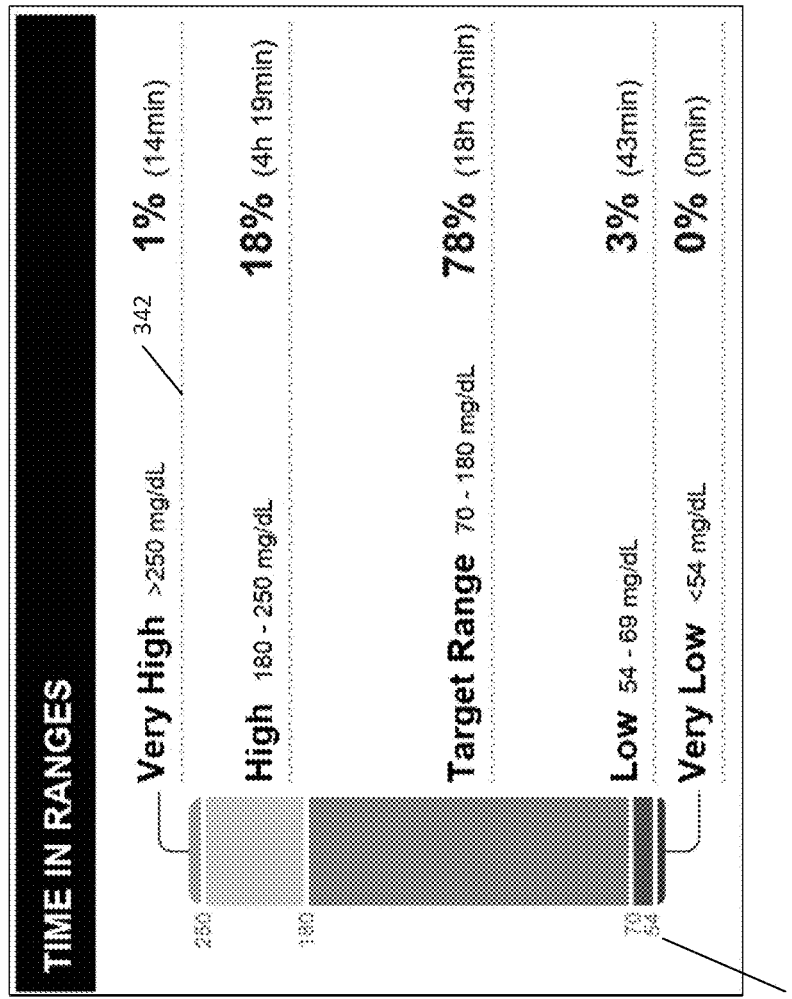
Figure 3E:
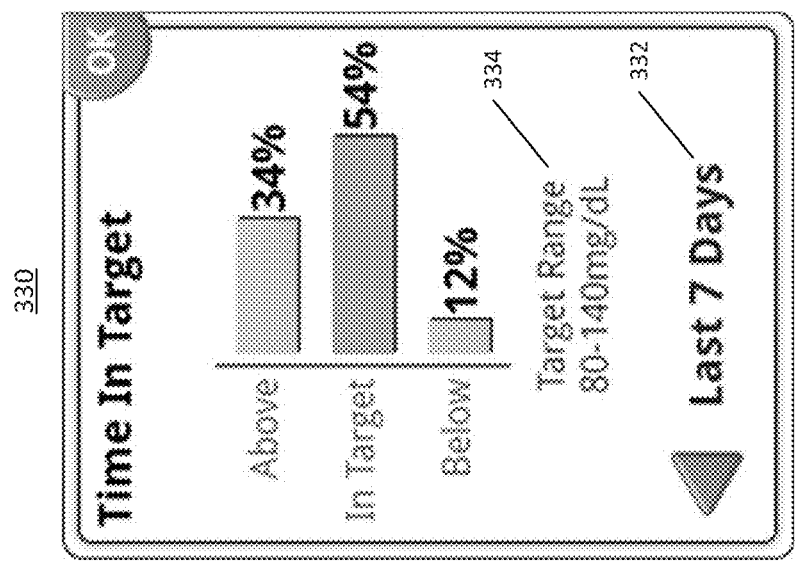

FIG. 3E depicts an example embodiment of a Time-in-Target GUI 330, which can be visually output to a display of a reader device (e.g., a dedicated reader device, a meter device, etc.). In accordance with the disclosed subject matter, Time-in-Target GUI 330 includes three bars comprising (from top to bottom): a first bar indicating that the user's glucose range is above a predefined target range for 34% of a predefined amount of time, a second bar indicating that the user's glucose range is within the predefined target range for 54% of the predefined amount of time, and a third bar indicating that the user's glucose range is below the predefined target range for 12% of the predefined amount of time. Those of skill in the art will recognize that the percentages of time associated with each bar can vary depending on the available analyte data of the user. Furthermore, although FIG. 3E shows a predefined amount of time 332 equal to the last seven days and a predefined target range 334 of 80 to 140 mg/dL, those of skill in the art will appreciate that other predefined amounts of time (e.g., one day, three days, fourteen days, thirty days, ninety days, etc.) and/or predefined target ranges (e.g., 70 to 180 mg/dL) can be utilized, and are fully within the scope of this disclosure.

FIG. 3F depicts another example embodiment of a Time-in-Ranges GUI 340, which includes a single bar comprising five bar portions including (from top to bottom): a first bar portion indicating that the user's glucose range is "Very High" or above 250 mg/dL for 1% (14 minutes) of a predefined amount of time, a second bar portion indicating that the user's glucose range is "High" or between 180 and 250 mg/dL for 18% (4 hours and 19 minutes) of the predefined amount of time, a third bar portion indicating that the user's glucose range is within a "Target Range" or between 70 and 180 mg/dL for 78% (18 hours and 43 minutes) of the predefined amount of time, a fourth bar portion indicating that the user's glucose range is "Low" or between 54 and 69 mg/dL for 3% (43 minutes) of the predefined amount of time, and a fifth bar portion indicating that the user's glucose range is "Very Low" or less than 54 mg/dL for 0% (0 minutes) of the predefined amount of time. As shown in FIG. 3F, according to some embodiments, Time-in-Ranges GUI 340 can display text adjacent to each bar portion indicating an actual amount of time, e.g., in hours and/or minutes.

According to one aspect of the embodiment shown in FIG. 3F, each bar portion of Time-in-Ranges GUI 340 can comprise a different color. In some embodiments, bar portions can be separated by dashed or dotted lines 342 and/or interlineated with numeric markers 344 to indicate the ranges reflected by the adjacent bar portions. In some embodiments, the time in ranges reflected by the bar portions can be further expressed as a percentage, an actual amount of time (e.g., 4 hours and 19 minutes), or, as shown in FIG. 3F, both. Furthermore, those of skill in the art will recognize that the percentages of time associated with each bar portion can vary depending on the analyte data of the user. In some embodiments of Time-in-Ranges GUI 340, the Target Range can be configured by the user. In other embodiments, the Target Range of Time-in-Ranges GUI 340 is not modifiable by the user.

Example Embodiments of Analyte Level and Trend Alert Interfaces

Figure 4C:
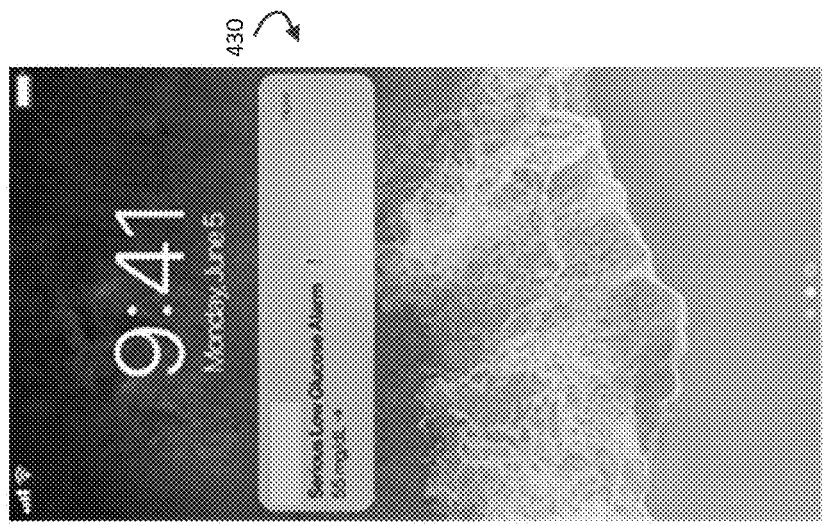
FIGS. 4A to 4O are example embodiments of GUIs comprising analyte level and trend alert interfaces.
Figure 4B:
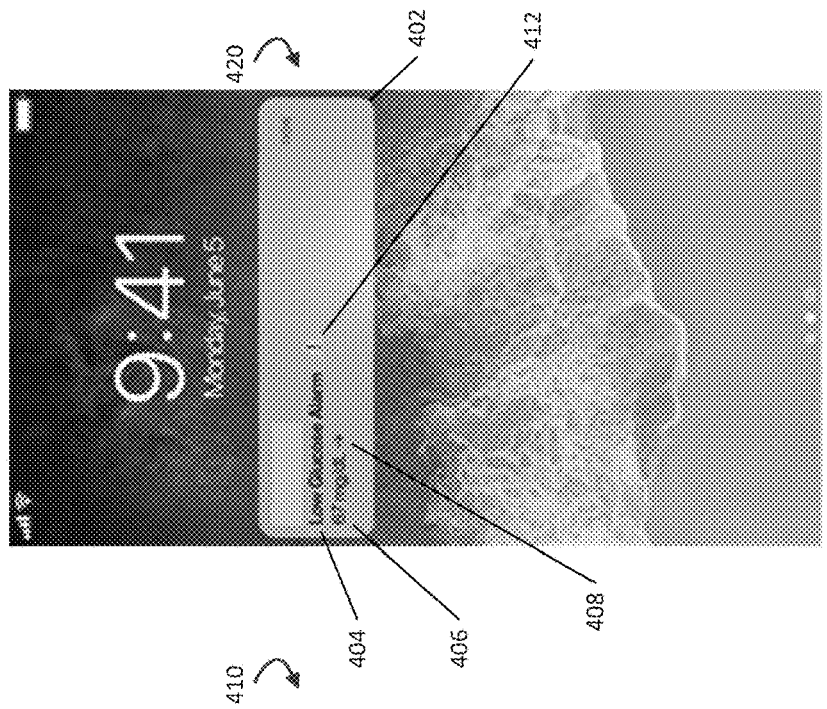
Figure 4A:
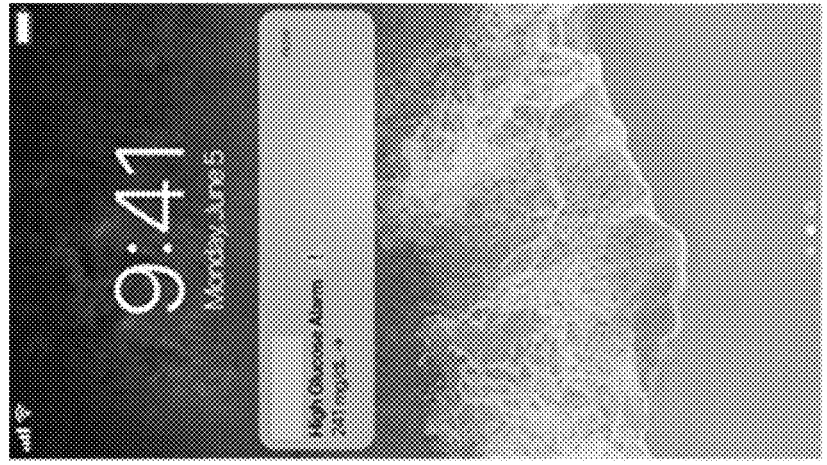
Figure 4D:
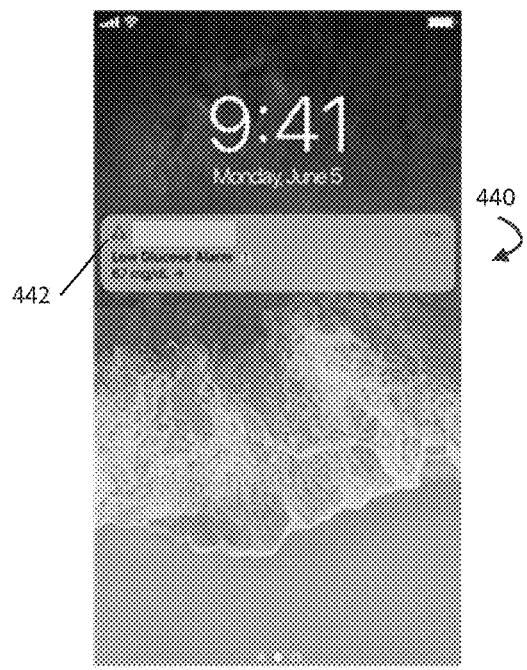
Figure 4E:
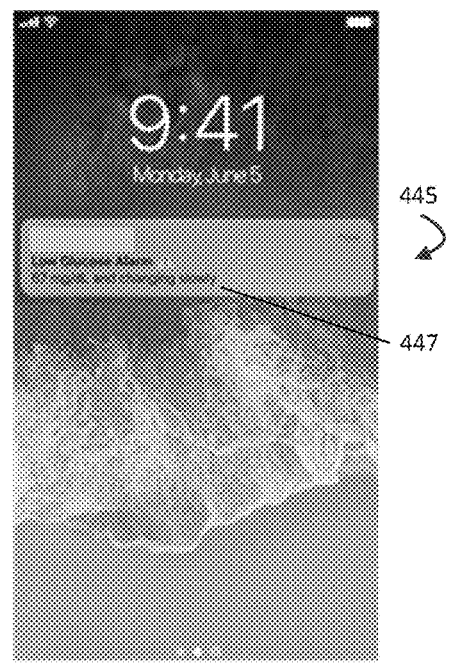
Figure 4F:
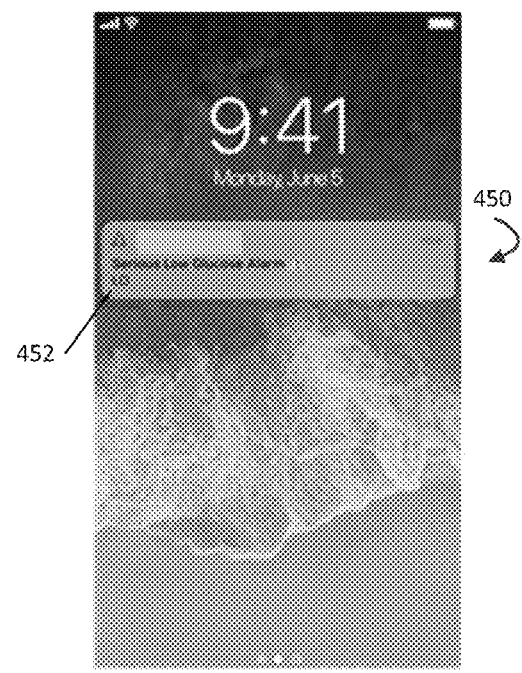
Figure 4G:
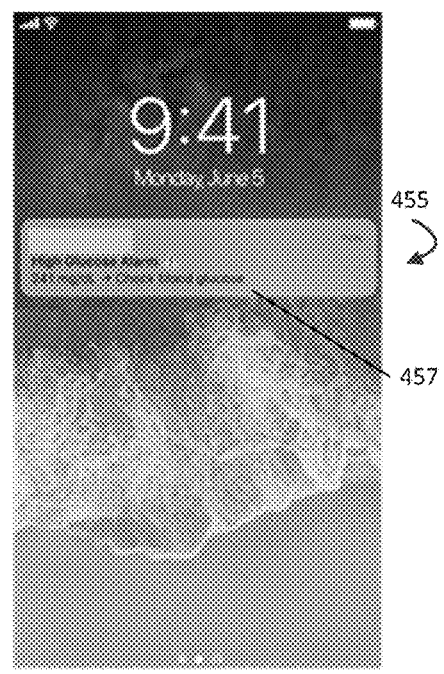
Figure 4J:
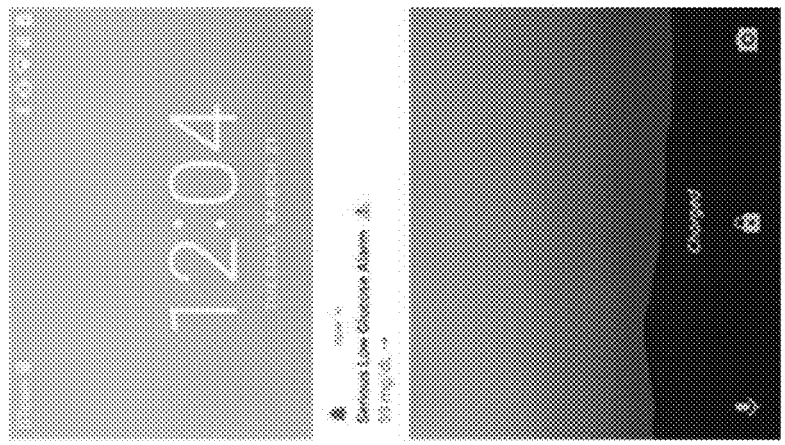
Figure 4I:
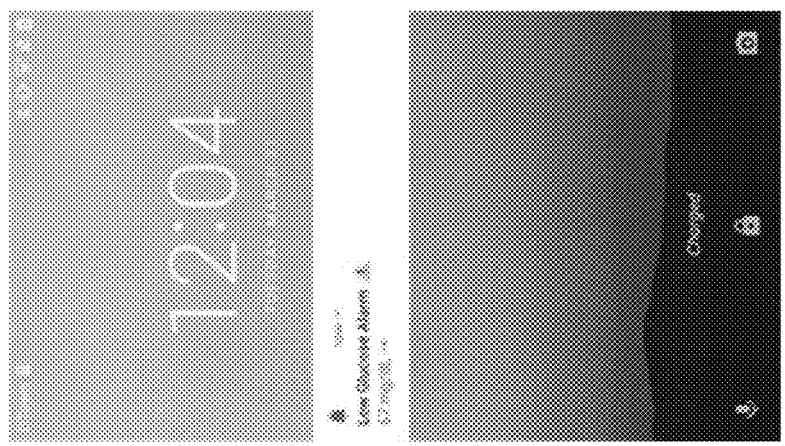
Figure 4H:
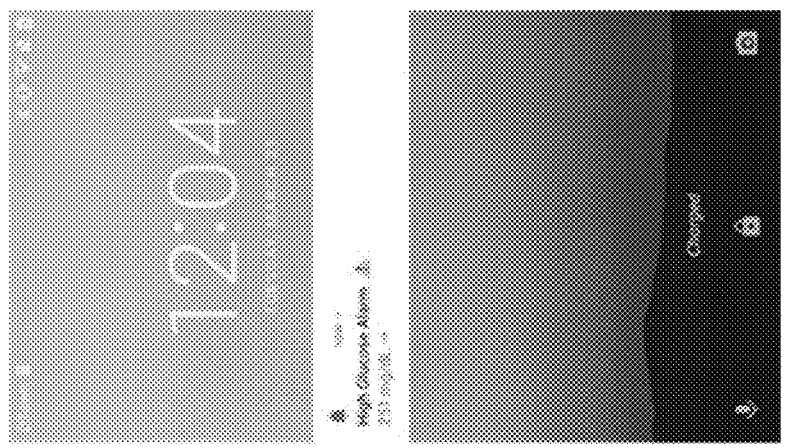
Figure 4K:
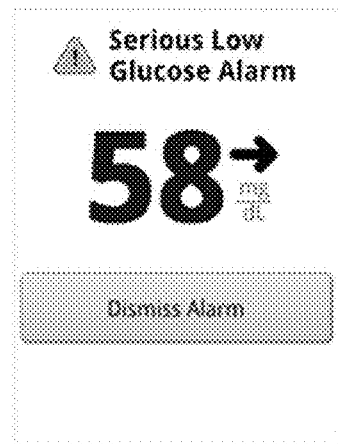
Figure 4L:
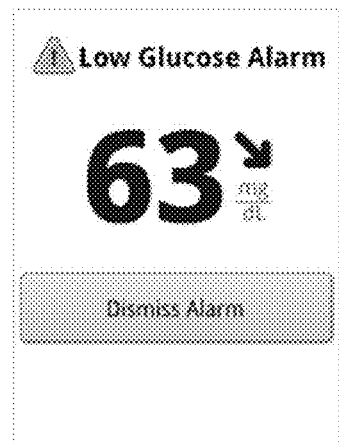
Figure 4M:
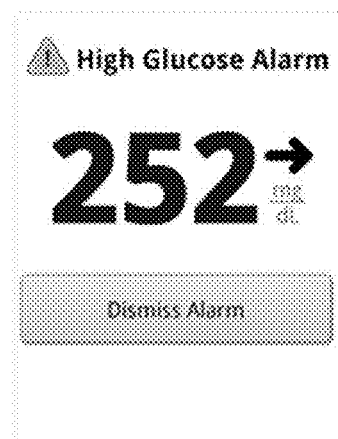
Figure 4N:
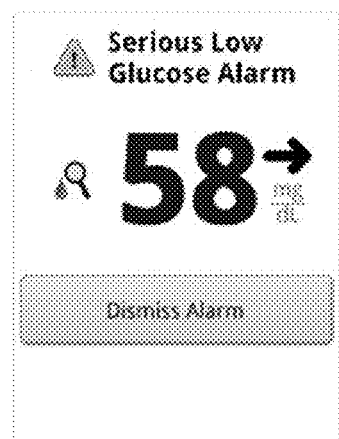
Figure 4O:
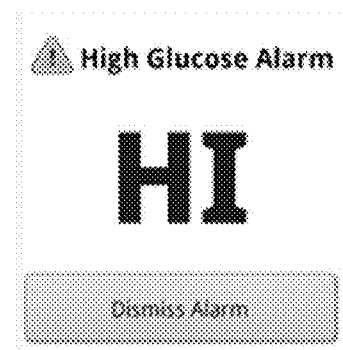

FIGS. 4A to 4O depict example embodiments of Analyte Level/Trend Alert GUIs for analyte monitoring systems. In accordance with the disclosed subject matter, the Analyte Level/Trend Alert GUIs comprise a visual notification (e.g., alert, alarm, pop-up window, banner notification, etc.), wherein the visual notification includes an alarm condition, an analyte level measurement associated with the alarm condition, and a trend indicator associated with the alarm condition.

Turning to FIGS. 4A to 4C, example embodiments of a High Glucose Alarm 410, Low Glucose Alarm 420, and a Serious Low Glucose Alarms 430 are depicted, respectively, wherein each alarm comprises a pop-up window 402 containing an alarm condition text 404 (e.g., "Low Glucose Alarm"), an analyte level measurement 406 (e.g., a current glucose level of 67 mg/dL) associated with the alarm condition, and a trend indicator 408 (e.g., a trend arrow or directional arrow) associated with the alarm condition. In some embodiments, an alarm icon 412 can be adjacent to the alarm condition text 404.

Referring next to FIGS. 4D to 4G, additional example embodiments of Low Glucose Alarms 440, 445, Serious Low Glucose Alarm 450, and High Glucose Alarm 455 are depicted, respectively. As shown in FIG. 4D, Low Glucose Alarm 440 is similar to the Low Glucose Alarm of FIG. 4B (e.g., comprises a pop-up window containing an alarm condition text, an analyte level measurement associated with the alarm condition, and a trend indicator associated with the alarm condition), but further includes an alert icon 442 to indicate that the alarm has been configured as an alert (e.g., will display, play a sound, vibrate, even if the device is locked or if the device's "Do Not Disturb" setting has been enabled). With respect to FIG. 4E, Low Glucose Alarm 445 is also similar to the Low Glucose Alarm of FIG. 4B, but instead of including a trend arrow, Log Glucose Alarm 445 includes a textual trend indicator 447. According to one aspect of some embodiments, textual trend indicator 447 can be enabled through a device's Accessibility settings such that the device will "read" the textual trend indicator 447 to the user via the device's text-to-speech feature (e.g., Voiceover for iOS or Select-to-Speak for Android).

Referring next to FIG. 4F, Low Glucose Alarm 450 is similar to the Low Glucose Alarm of FIG. 4D (including the alert icon), but instead of displaying an analyte level measurement associated with an alarm condition and a trend indicator associated with the alarm condition, Low Glucose Alarm 450 displays a out-of-range indicator 452 to indicate that the current glucose level is either above or below a predetermined reportable analyte level range (e.g., "HI" or "LO"). With respect to FIG. 4G, High Glucose Alarm 455 is similar to the High Glucose Alarm of FIG. 4A (e.g., comprises a pop-up window containing an alarm condition text, an analyte level measurement associated with the alarm condition, and a trend indicator associated with the alarm condition), but further includes an instruction to the user 457. In some embodiments, for example, the instruction can be a prompt for the user to "Check blood glucose." Those of skill in the art will appreciate that other instructions or prompts can be implemented (e.g., administer a corrective bolus, eat a meal, etc.).

Furthermore, although FIGS. 4A to 4G depict example embodiments of Analyte Level/Trend Alert GUIs that are displayed on smart phones having an iOS operating system, those of skill in the art will also appreciate that the Analyte Level/Trend Alert GUIs can be implemented on other devices including, e.g., smart phones with other operating systems, smart watches, wearables, reader devices, tablet computing devices, blood glucose meters, laptops, desktops, and workstations, to name a few. FIGS. 4H to 4J, for example, depict example embodiments of a High Glucose Alarm, Low Glucose Alarm, and a Serious Low Glucose Alarm for a smart phone having an Android Operating System. Similarly, FIGS. 4K to 4O depict, respectively, example embodiments of a Serious Low Glucose Alarm, Low Glucose Alarm, High Glucose Alarm, Serious Low Glucose Alarm (with a Check Blood Glucose icon), and High Glucose Alarm (with an out-of-range indicator) for a reader device.

Example Embodiments of Sensor Usage Interfaces

FIGS. 5A to 5F depict example embodiments of sensor usage interfaces relating to GUIs for analyte monitoring systems. In accordance with the disclosed subject matter, sensor usage interfaces provide for technological improvements including the capability to quantify and promote user engagement with analyte monitoring systems. For example, the user can benefit from subtle behavioral modification as the sensor usage interface encourages more frequent interaction with the device and the expected improvement in outcomes. The user can also benefit from increased frequent interaction which leads to improvement in a number of metabolic parameters, as discussed in further detail below.

In some embodiments, HCPs can receive a report of the user's frequency of interaction and a history of the patient's recorded metabolic parameters (e.g., estimated HbA1c levels, time in range of 70-180 mg/dL, etc.). If an HCP sees certain patients in their practice are less engaged than others, the HCPs can focus their efforts on improving engagement in users/patients that are less engaged than others. HCPs can benefit from more cumulative statistics (such as average glucose views per day, average glucose views before/after meals, average glucose views on "in-control" vs. "out-of-control" days or time of day) which may be obtained from the record of user's interaction frequency with the analyte monitoring systems and which can be used to understand why a patient may not be realizing expected gains from the analyte monitoring system. If an HCP sees that a patient is not benefiting as expected from the analyte monitoring system, they may recommend an increased level of interaction (e.g., increase interaction target level). Accordingly, an HCP can change the predetermined target level of interaction.

In some embodiments, caregivers can receive a report of the user's frequency of interaction. In turn, caregivers may be able to nudge the user to improve interaction with the analyte monitoring system. The caregivers may be able to use the data to better understand and improve their level of engagement with the user's analyte monitoring systems or alter therapy decisions.

According to some embodiments, for example, a sensor usage interface can include the visual display of one or more "view" metrics, each of which can be indicative of a measure of user engagement or interaction with the analyte monitoring system. A "view" can comprise, for example, an instance in which a sensor results interface is rendered or brought into the foreground (e.g., in certain embodiments, to view any of the GUI described herein). In some embodiments, the update interval as described above, data on sensor results GUI 245 is automatically updated or refreshed according to an update interval (e.g., every second, every minute, every 5 minutes, etc.). As such, a "view" can comprise one instance per update interval in which a sensor results interface is rendered or brought into the foreground. For example, if the update interval is every minute, rendering or bringing into the foreground the sensor results GUI 245 several times in that minute would only comprise one "view." Similarly, if the sensor results GUI 245 is rendered or brought into the foreground for 20 continuous minutes, data on the senor results GUI 245 would be updated 20 times (i.e., once every minute). However, this would only constitute 20 "views" (i.e., one "view" per update interval). Similarly, if the update interval is every five minutes, rendering or bringing into the foreground the sensor results GUI 245 several times in those five minutes would only comprise one "view." If the sensor results interface is rendered or brought into the foreground for 20 continuous minutes, this would constitute 4 "views" (i.e., one "view" each for each of the four five-minute intervals). According to other embodiments, a "view" can be defined as an instance when a user views a sensor results interface with a valid sensor reading for the first time in a sensor lifecount. According to disclosed embodiments, user can receive a notification, as described below, indicating when an instance of rendering or brining into the foreground the sensor results GUI is not counted as a "view." For example, the user can receive a visual notification indicating such as "Results have not updated," or "View does not count," or "Please check glucose level again." In some embodiments, the user can receive a check-in for each instance which counts as a "view," as described in greater detail below.

According to disclosed embodiments, the one or more processors can be configured to record no more than one instance of user operation of the reader device during a defined time period. For example, and not limitation, a defined time period can include an hour. A person of ordinary skill in the art would understand defined time period to include any appropriate period of time, such as, one hour, two hours, three hours, 30 minutes, 15 minutes, etc.

According to some embodiments, a "view" can comprise, for example, a visual notification (e.g., prompt, alert, alarm, pop-up window, banner notification, etc.). In some embodiments, the visual notification can include an alarm condition, an analyte level measurement associated with the alarm condition, and a trend indicator associated with the alarm condition. For example, Analyte Level/Trend Alert GUIs, such as those embodiments depicted in FIGS. 4A to 4O can constitute a "view."

In some embodiments, a sensor user interface can include a visual display of a "scan" metric indicative of another measure of user engagement or interaction with the analyte monitoring system. A "scan" can comprise, for example, an instance in which a user uses a reader device (e.g., smart phone, dedicated reader, etc.) to scan a sensor control device, such as, for example, in a Flash Analyte Monitoring system. As described above in connection with "views", a "scan" can comprise one instance per update interval in a user uses a reader device to scan a sensor control device.

Figures 5A, 5B:
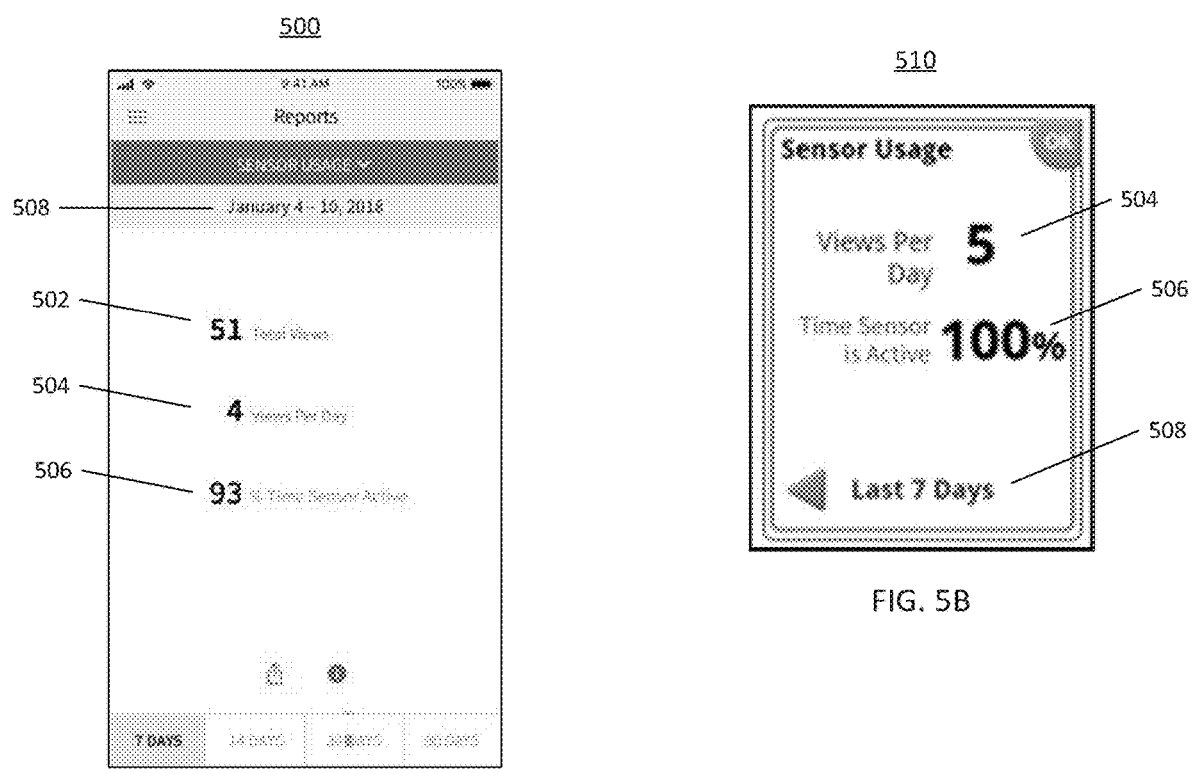
FIGS. 5A and 5B are example embodiments of GUIs comprising sensor usage interfaces.

FIGS. 5A and 5B depict example embodiments of sensor usage interfaces 500 and 510, respectively. In accordance with the disclosed subject matter, sensor usage interfaces 500 and 510 can be rendered and displayed, for example, by a mobile app or software residing in non-transitory memory of reader device 120, such as those described with respect to FIGS. 1 and 2A. In some embodiments, for each instance of a "views" or "scans," the software can record the date and time of the user's interaction with the system. In some embodiments, for each instance of a "view" or "scan," the software can record the current glucose value. Referring to FIG. 5A, sensor user interface 500 can comprise: a predetermined time period interval 508 indicative of a time period (e.g., a date range) during which view metrics are measured, a Total Views metric 502, which is indicative of a total number of views over the predetermined time period 508; a Views Per Day metric 504, which is indicative of an average number of views per day over the predetermined time period 508; and a Percentage Time Sensor Active metric 506, which is indicative of the percentage of predetermined time period 508 that reader device 120 is in communication with sensor control device 102, such as those described with respect to FIGS. 1, 2B, and 2C. Referring to FIG. 5B, sensor user interface 510 can comprise a Views per Day metric 504 and a Percentage Time Sensor Active metric 508, each of which is measured for predetermined time period 508.

According to another aspect of the embodiments, although predetermined time period 508 is shown as one week, those of skill in the art will recognize that other predetermined time periods (e.g., 3 days, 14 days, 30 days) can be utilized. In addition, predetermined time period 508 can be a discrete period of time—with a start date and an end date—as shown in sensor usage interface 500 of FIG. 5A, or can be a time period relative to a current day or time (e.g., "Last 7 Days," "Last 14 Days," etc.), as shown in sensor usage interface 510 of FIG. 5B.

Figure 5C:
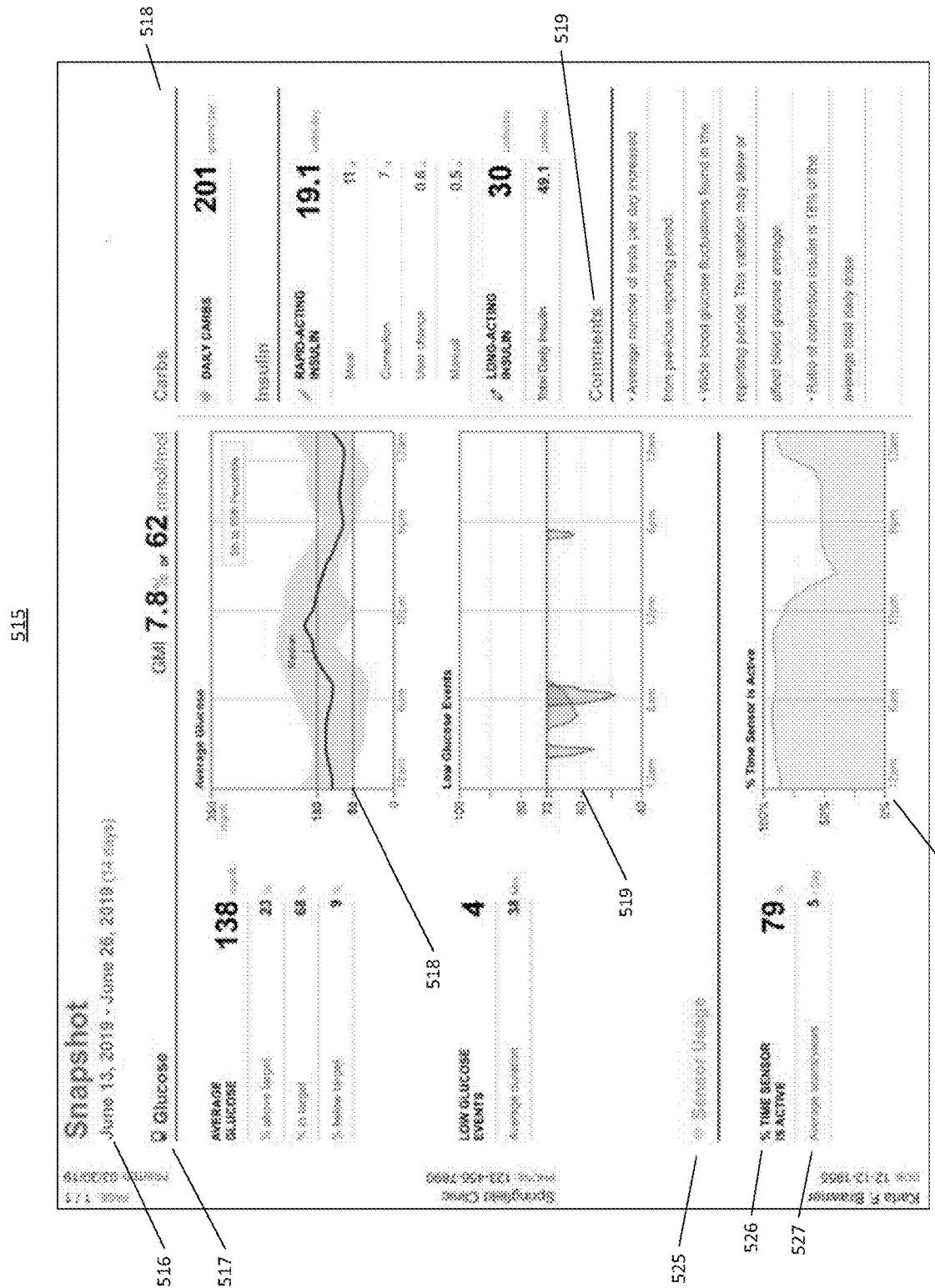

FIG. 5C depicts an example embodiment of sensor usage interface 525, as part of analyte monitoring system report GUI 515. In accordance with the disclosed subject matter, GUI 515 is a snapshot report covering a predetermined time period 516 (e.g., 14 days), and comprising a plurality of report portions on a single report GUI, including: a sensor usage interface portion 525, a glucose trend interface 517, which can include an glucose trend graph, a low glucose events graph, and other related glucose metrics (e.g., Glucose Management Indicator); a health information interface 518, which can include information logged by the user about the user's average daily carbohydrate intake and medication dosages (e.g., insulin dosages); and a comments interface 519, which can include additional information about the user's analyte and medication patterns presented in a narrative format. According to another aspect of the embodiments, sensor usage interface 525 can comprise a Percentage Time Sensor Active metric 526, an Average Scans/Views metric 527 (e.g., indicative of an average sum of a number of scans and a number of views), and a Percentage Time Sensor Active graph 528. As can be seen in FIG. 5C, an axis of the Percentage Time Sensor Active graph can be aligned with a corresponding axis of one or more other graphs (e.g., average glucose trend graph, low glucose events graph), such that the user can visually correlate data between multiple graphs from two or more portions of the report GUI by the common units (e.g., time of day) from the aligned axes.

Figure 5D:
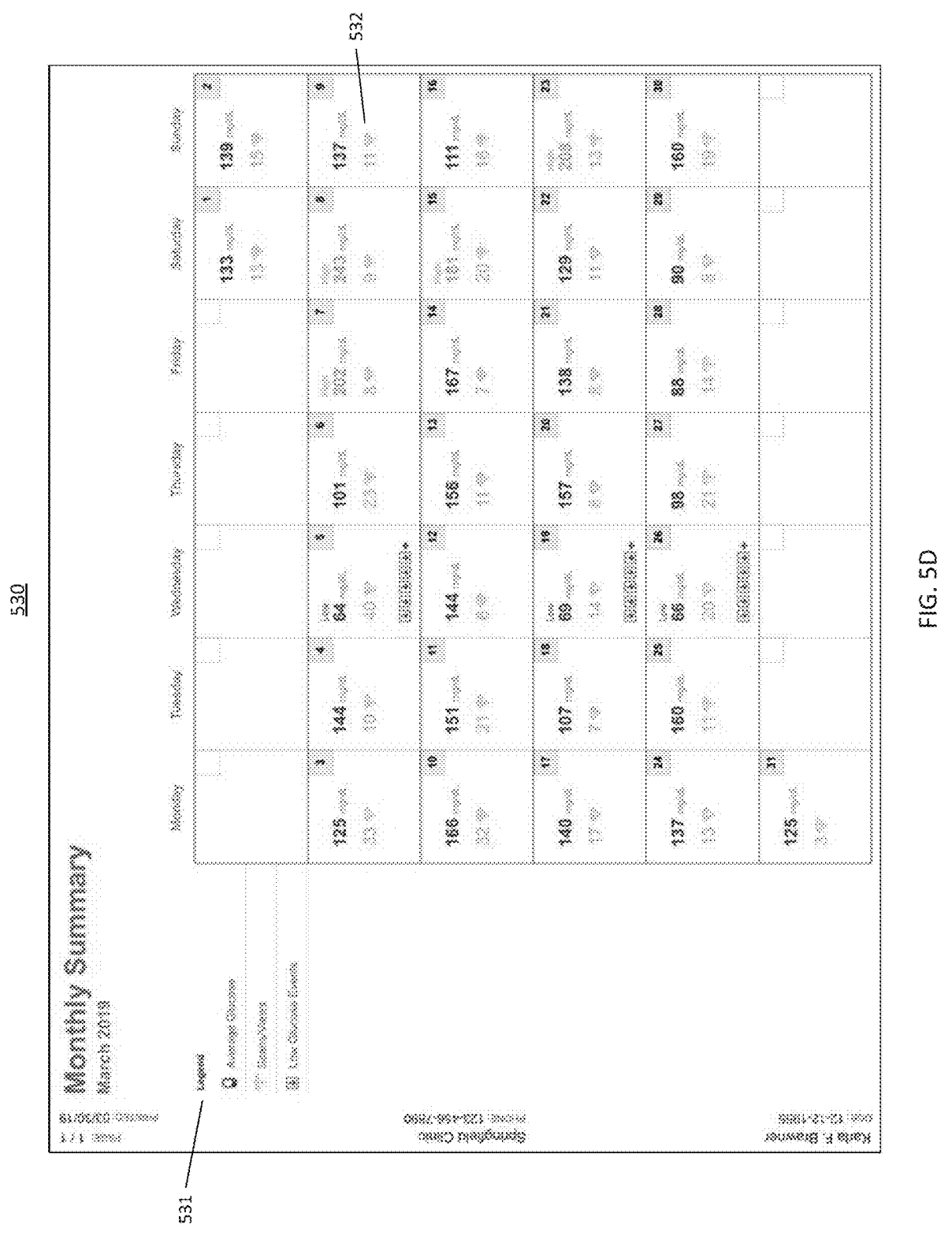

FIG. 5D depicts an example embodiment of another analyte monitoring system report GUI 530 including sensor usage information. In accordance with the disclosed subject matter, GUI 530 is a monthly summary report including a first portion comprising a legend 531, wherein legend 531 includes a plurality of graphical icons each of which is adjacent to a descriptive text. As shown in FIG. 5D, legend 531 includes an icon and descriptive text for "Average Glucose," an icon and descriptive text for "Scans/Views," and an icon and descriptive text for "Low Glucose Events." GUI 530 also includes a second portion comprising a calendar interface 532. For example, as shown in FIG. 5D, GUI 530 comprises a monthly calendar interface, wherein each day of the month can include one or more of an average glucose metric, low glucose event icons, and a sensor usage metric 532. In some embodiments, such as the one shown in FIG. 5D, the sensor usage metric ("scans/views") is indicative of a total sum of a number of scans and a number of views for each day.

Figure 5E:
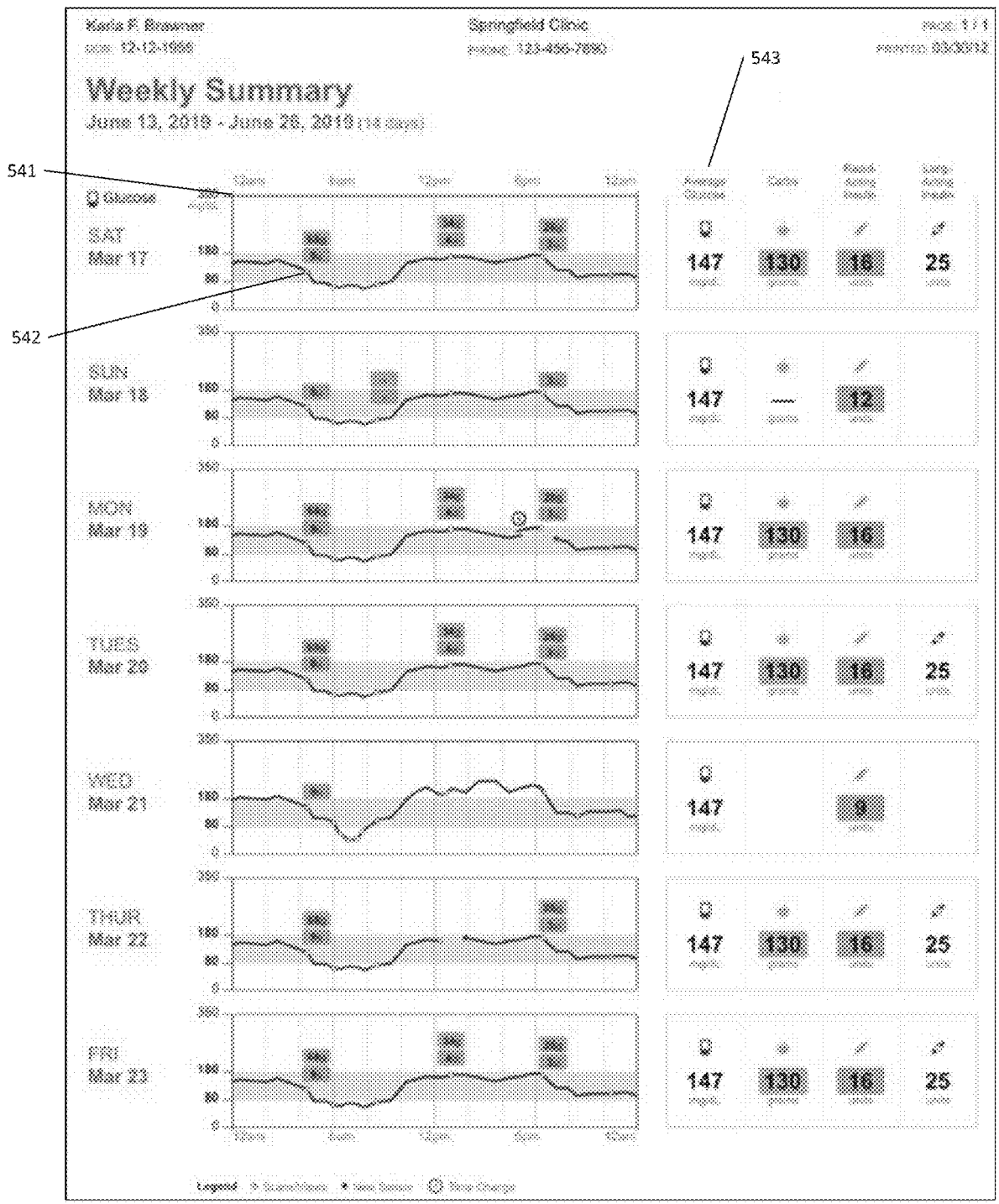

FIG. 5E depicts an example embodiment of another analyte monitoring system report GUI 540 including sensor usage information. In accordance with the disclosed subject matter, GUI 540 is a weekly summary report including a plurality of report portions, wherein each report portion is representative of a different day of the week, and wherein each report portion comprises a glucose trend graph 541, which can include the user's measured glucose levels over a twenty-four hour period, and a health information interface 543, which can include information about the user's average daily glucose, carbohydrate intake, and/or insulin dosages. In some embodiments, glucose trend graph 541 can include sensor usage markers 542 to indicate that a scan, a view, or both had occurred at a particular time during the twenty-four hour period.

Figure 5F:
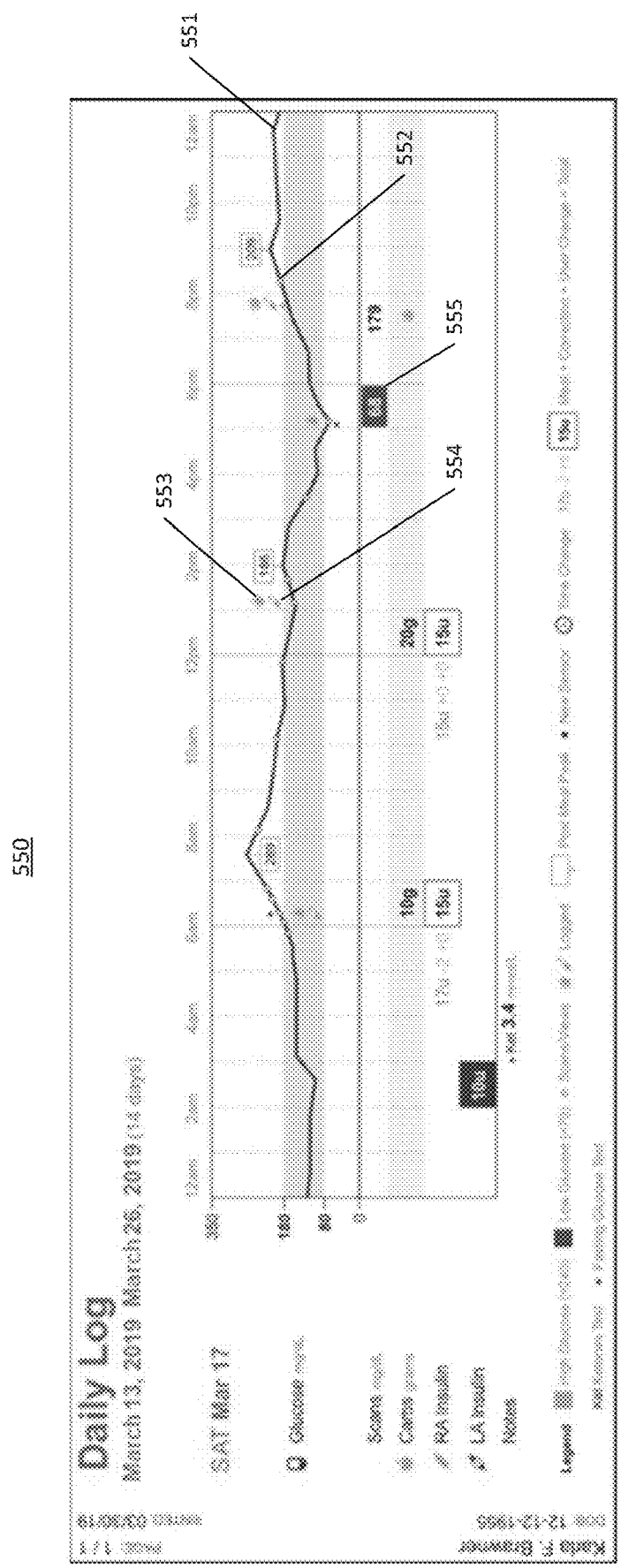

FIG. 5F depicts an example embodiment of another analyte monitoring system report GUI 550 including sensor usage information. In accordance with the disclosed subject matter, GUI 550 is a daily log report comprising a glucose trend graph 551, which can include the user's glucose levels over a twenty-four hour period. In some embodiments, glucose trend graph 551 can include sensor usage markers 552 to indicate that a scan, a view, or both had occurred at a particular time during the twenty-four hour period. Glucose trend graph 551 can also include logged event markers, such as logged carbohydrate intake markers 553 and logged insulin dosage markers 554, as well as glucose event markers, such as low glucose event markers 555.

FIGS. 5I to 5L depict various GUIs for improving usability and user privacy with respect to analyte monitoring software. FIG. 5G, GUI 5540 depicts a research consent interface 5540, which prompts the user to choose to either decline or opt in (through buttons 5542) with respect to permitting the user's analyte data and/or other product-related data to be used for research purposes. According to embodiments of the disclosed subject matter, the analyte data can be anonymized (de-identified) and stored in an international database for research purposes.

Figure 5H:
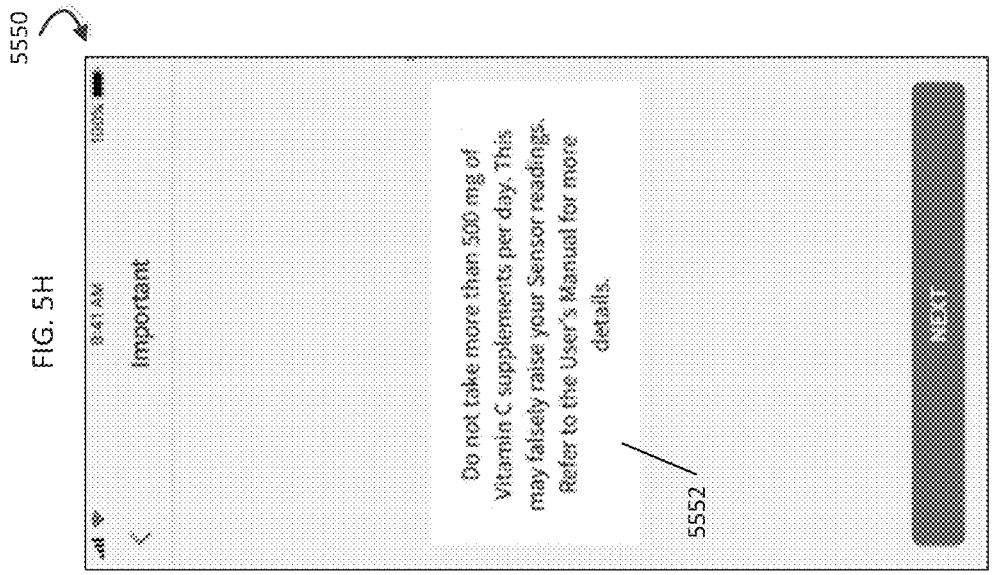
FIGS. 5G-5L are example embodiments of GUIs relating to an analyte monitoring software application.
Figure 5G:

Referring next to FIG. 5H, GUI 5550 depicts a "Vitamin C" warning interface 5550 which displays a warning to the user that the daily use of more than 500 mg of Vitamin C supplements can result in falsely high sensor readings.

Figure 5I:
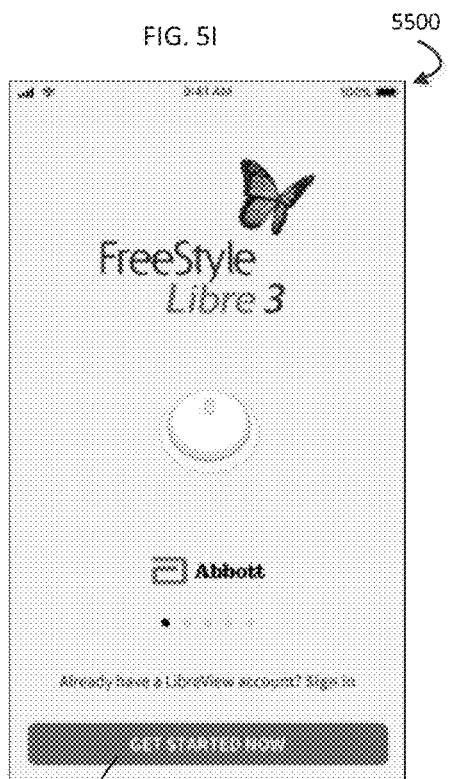
Figure 5J:
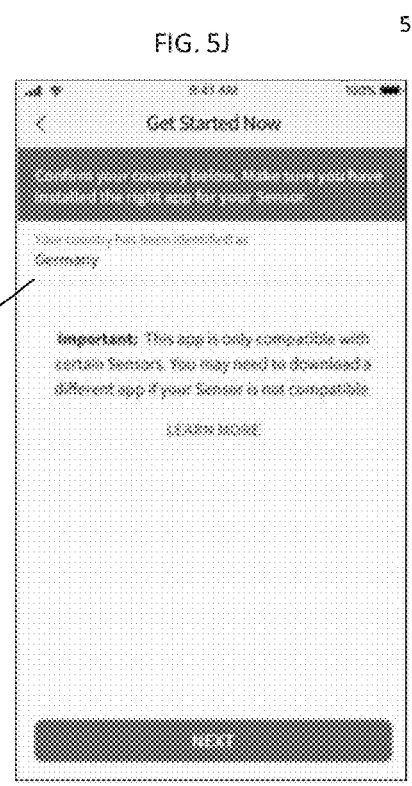

FIG. 5I is GUI 5500 depicting a first start interface which can be displayed to a user the first time the analyte monitoring software is started. In accordance with the disclosed subject matter, GUI 5500 can include a "Get Started Now" button 5502 that, when pressed, will navigate the user to GUI 5510 of FIG. 5J. GUI 5510 depicts a country confirmation interface 5512 that prompts the user to confirm the user's country. According to another aspect of the embodiments, the country selected can limit and/or enable certain interfaces within the analyte monitoring software application for regulatory compliance purposes.

Figure 5K:
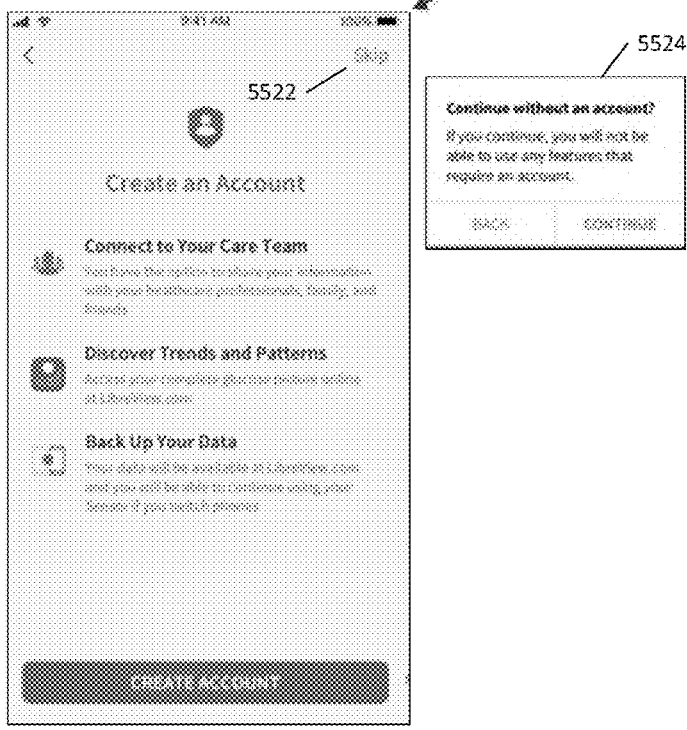

Turning next to FIG. 5K, GUI 5520 depicts a user account creation interface which allows the user to initiate a process to create a cloud-based user account. Iin accordance with the disclosed subject matter, a cloud-based user account can allow the user to share information with healthcare professionals, family and friends; utilize a cloud-based reporting platform to review more sophisticated analyte reports; and back up the user's historical sensor readings to a cloud-based server. In some embodiments, GUI 5520 can also include a "Skip" link 5522 that allows a user to utilize the analyte monitoring software application in an "accountless mode" (e.g., without creating or linking to a cloud-based account). Upon selecting the "Skip" link 5522, an information window 5524 can be displayed to inform that certain features are not available in "accountless mode." Information window 5524 can further prompt the user to return to GUI 5520 or proceed without account creation.

Figure 5L:
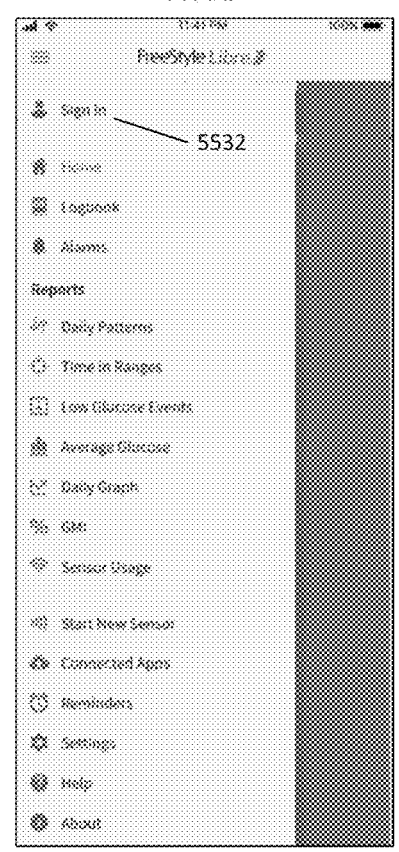

FIG. 5L is GUI 5530 depicting a menu interface displayed within an analyte monitoring software application while the user is in "accountless mode." According to an aspect of the embodiments, GUI 5530 includes a "Sign in" link 5532 that allows the user to leave "accountless mode" and either create a cloud-based user account or sign-in with an existing cloud-based user account from within the analyte monitoring software application.

It will be understood by those of skill in the art that any of the GUIs, reports interfaces, or portions thereof, as described herein, are meant to be illustrative only, and that the individual elements, or any combination of elements, depicted and/or described for a particular embodiment or figure are freely combinable with any elements, or any combination of elements, depicted and/or described with respect to any of the other embodiments.

Figure 12A:
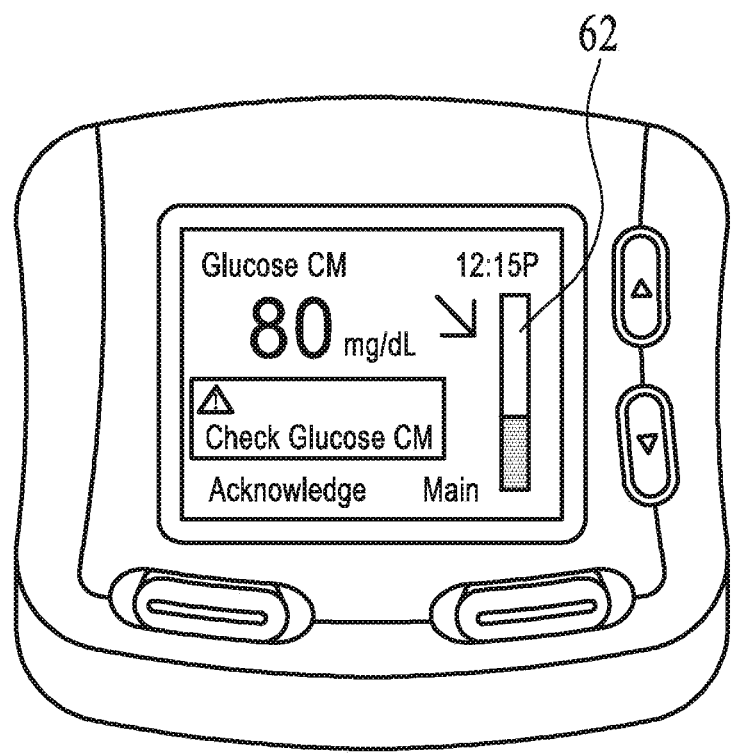
FIGS. 12A-12B are example embodiments of GUIs which manage an alarm system.

In another exemplary embodiment, as illustrated in FIG. 12A, the display 122 can display a bar graph 62, or any other suitable indicator, comparing the user's frequency of interaction (e.g., without limitation, frequency of "view" or "scans", scanning frequency, or viewing frequency, reviewing historical glucose reports, interacting with HCPs through the CGM system's platform) with the reader device 120 to a predetermined target frequency. In this exemplary embodiment, the reader device 120 can further include an algorithm for comparing the frequency of user interaction with the reader device to a predetermined frequency of interaction. In some embodiments, the predetermined frequency can be output to a display on reader device 120. In this exemplary embodiment, if the frequency of a user's interaction with the reader device 120 matches or falls below the predetermined level of interaction, the reader device can alert the user through an audible or vibratory alert. The alert system will be described in greater detail below.

In another exemplary embodiment of this disclosure, the reader device 120 can also contain software designed to encourage interaction with the reader devices. For example, the software can set target rates for the user, so that the user strives to achieve a desired interaction frequency with the reader device. In another exemplary embodiment, the software can offer educational information related to treatment as well as helpful hints and tips, thereby educating the user as to the importance of maintaining a predetermined target level of interaction with the reader device.

In yet another embodiment, the reader device 120 can include software that prompts user interaction, e.g., an electronic game, or cartoon-like character or the like, that requires feedback from the user. In one exemplary embodiment, the cartoon-like character or the like can have a "health bar" or a "life bar" which would represent the level of interaction between the user and the analyte monitoring system. That is, by frequently interacting with the cartoon-like character, the user will keep the health, or life, level of the cartoon-like character above the predetermined target level. In one exemplary embodiment, the user can "feed" the cartoon-like character by interacting with the device. The user's analyte level, or other relevant information should also be displayed on the screen of the device during interaction between the user and the cartoon-like character. In one exemplary embodiment, the user will be limited in the amount of interaction in a predetermined time. That is, the user will not be able to front-load the amount of interaction with the device, and then ignore the device for a prolonged period of time. As such, the device can only record a predetermined number of interactions within a certain period of time.

By interacting with the cartoon-like character, the user can also be educated as to the benefits of maintaining a proper target rate of interaction with the device, or can at least stay informed as to his own state of health. This embodiment can be particularly interesting to children as it can help ensure that children maintain a predetermined level of interaction with the monitoring device of this disclosure. This exemplary embodiment can also be coupled with education regarding treatment options, helpful hints and tips. Moreover, the above-described embodiment need not be used with a continuous glucose monitoring ("CGM") device.

In an embodiment, software on the reader device 120 can include check-ins or badges that the user can "earn." In some embodiments, the user can receive a check-in for each instance of user interaction. In some embodiments, a user can earn a check-in for an instance of user interaction if a period of time has elapsed since the user's last interaction with the device. For example, and not limitation, a period of time which must elapse between subsequent instances of user interaction for the user to earn a check-in could include any reasonable period of time, such as, for example, 5 minutes, 10 minutes, 15 minutes, 30 minutes, 45 minutes, 60 minutes, etc. According to a preferred embodiment, the period of time which must elapse can include 60 minutes. In some embodiments, a user can earn a badge if the user's frequency of interaction with the system is equal to or greater than a predetermined target level of user interaction over a period of time. For example, and not limitation, the period of time can include any reasonable period of time, such as, for example, one day, 7 days, 14 days, a date range, 30 days, 90 days, etc. For example, and not limitation, check-ins and badges can include a visual notification or an audio notification. For example, and not limitation, badges and check-ins can include a star, icon, or any other commemorative graphic to commemorate frequency of user interaction, cumulative user interactions, or each user interaction.

In one exemplary embodiment, the system can automatically adjust the period of time based upon the user's activity level or state of general wellness. In one exemplary embodiment, the system can automatically adjust the period of time based upon machine learning or artificial intelligence techniques. In these exemplary embodiments, the system can use steps per day, pulse rate, body temperature, respiration rate, time in target range, estimated HbA1c level, number of insulin injection over a period of time, or other indicators to adjust the period of time. For example, and not limitation, if the user has been active, the system can reduce or increase the period of time. Additionally, the target period of time can be automatically or intelligently adjusted based on the user's baseline level of interaction. For example, the period of time can be initially low, but can thereafter be automatically and intelligently increased or decreased based on the user's baseline level of interaction over a period of time. For example, and not limitation, the period of time can include any reasonable period of time, such as, for example, one day, 7 days, 14 days, a date range, 30 days, 90 days, etc.

In an embodiment, the period of time can be set by an HCP. In one exemplary embodiment, the period of time can be programmed (or user modifiable) to vary during the course of the day or week (work week vs. weekend), with the period of time being easily adjustable to account for events or changes, such as, during sick days, times of high activity (e.g., high number of steps per day), or other times when more frequent interactions should be encouraged.

In order to achieve the full benefit of the analyte monitoring system, the user should maintain a predetermined target frequency of interaction with the system. In one exemplary embodiment, the predetermined target level of user interaction is set by an HCP, or the user's health care team. Thus, each predetermined target level of interaction will likely depend on the specific user. However, in one exemplary embodiment, factors affecting the predetermined level of user interaction with the system can be: the particular analyte to be measured, the user's general state of health, (for example, more frequent during sick days), symptoms exhibited by the user, time of day, time since or until meal, activity level and other events.

In one exemplary embodiment, the target level can be programmed (or user modifiable) to vary during the course of the day or week (work week vs. weekend), with these rates being easily adjustable to account for events or changes, such as, during sick days, times of high activity (e.g., high number of steps per day), or other times when more frequent interactions should be encouraged. Although HCPs can recommend only general interaction levels (e.g., once per hour during waking hours), these levels can be tailored to the individual user. For example, if a user feels overwhelmed with CGM technology, lower target levels of interaction can be needed, whereas a user who feels empowered by the technology can be encouraged to interact with the device at a higher frequency. Generally, HCPs will review interaction levels during routine visits when assessing general health and reviewing data uploads (e.g., approximately every 3 months for patients with diabetes). However, this approach can differ depending on the user, or other factors.

In another exemplary embodiment, the predetermined target level of user interaction with the reader device 120 can be set according to the time of day. For example, a user can interact with the reader device 120 more frequently during the day than at night. Additionally, in another exemplary embodiment, the predetermined target level of user interaction with the reader device 120 can be set according to the type of activity being performed by the user. For example, a user on a long-distance bicycle ride or car ride can need to check the analyte levels more frequently. In one exemplary embodiment, an HCP can recommend target levels of interaction corresponding to various events. In another exemplary embodiment, the target level of user interaction can be set by the user, or any other authorized party.

In one exemplary embodiment, the system can automatically adjust the target level of interaction based upon the user's activity level or state of general wellness. In one exemplary embodiment, the system can automatically adjust the target level of interaction based upon machine learning or artificial intelligence techniques. In these exemplary embodiments, the system can use steps per day, pulse rate, body temperature, respiration rate, time in target range, estimated HbA1c level, number of insulin injection over a period of time, or other indicators to adjust the analyte level. Additionally, the target level of interaction can be automatically or intelligently adjusted based on the user's baseline level of interaction. For example, the target level of interaction can be initially high, but can thereafter be automatically and intelligently reduced based on the user's baseline level of interaction over a period of time. Conversely, the target level of interaction can initially be low, but can thereafter be automatically and intelligently increased based on the user's baseline level of interaction over a period of time. For example, and not limitation, the period of time can include any reasonable period of time, such as, for example, one day, 7 days, 14 days, a date range, 30 days, 90 days, etc. Alternatively, position sensors, accelerometers or the like can be used to detect sleep and reduce (or even suspend) the target interaction frequency.

In an exemplary embodiment, the target level of interaction can gradually or incrementally increase over a period of time. For example, and not limitation, an initial target level of interaction can be an easier target level (e.g., 5 scans per day). The initial target level of interaction can remain unchanged for a first predetermined time period (e.g., one week) Thereafter, during a second predetermined period of time (e.g., one week), the initial target level of interaction can increase by an incremental level of change to medium target level (e.g., 6 scans per day during the second week), and thereafter, after another second predetermined period of time, increase by an incremental level of change to a high target level (i.e., 7 scans per day during third week). According to another aspect of the embodiments, although initial, medium, and high target levels are described as 5 scans per day, 6 scans per day, 7 scans per day, those of skill in the art will recognize that other predetermined target levels can be utilized. Additionally, the initial, medium, and high target level of interaction, and the incremental level of change, can be any suitable target level of interaction, and can, without limitation, vary based on the user, can be programmable, set by the HCP or user, or adjustable as described herein. Those of skill in the art will recognize that first and second predetermined time period can be any suitable time periods (e.g., 1 or more days, 1 or more weeks, 1 or more months, etc.).

In another exemplary embodiment, the analyte monitoring system can use the detected analyte levels to adjust future target levels of interaction. For example, the system can use an increase in glucose level, an increase in the rate of change of the glucose level, user entered information or some other analysis of the measured analyte level to identify a need to adjust the current target level of interaction. In one exemplary embodiment, the analyte levels can detect that the user has recently had a meal and can then adjust the interaction frequency automatically to a pre-programmed or user-set level.

Another exemplary embodiment can include a plurality of predetermined target levels of user interaction with the system of this disclosure. For example, this disclosure can include an "ideal" level of interaction, an "acceptable" level of interaction and a "critical" level of interaction. These levels can shift based on several factors. In one exemplary embodiment, the level of interaction can be adjusted to an increased or decreased target level of interaction based upon the monitoring results, based upon some user interaction with the device (e.g., meal or activity level entry), or can be pre-programmed to vary with the time of day or day of the week. The monitoring results can include, analyte levels, the rate of change of analyte levels, etc.

In another exemplary embodiment, the interaction frequency level can be relative to the predetermined target interaction frequency. For example, "ideal" can be approximately 90% or more of the target level; "acceptable" can be 70-90% of the target level; and "critical" can be below 70% of the target level.

In another exemplary embodiment of this disclosure, the analyte monitoring system can adjust the predetermined target levels of user interaction according to the condition of the user. Using glucose as an example, if the user's level of glucose drops below a certain threshold, the system can alert the user that hypoglycemia can occur. In this exemplary embodiment, the analyte monitoring system can adjust the target rate of user interaction to be more frequent, thus prompting the user to interact with the device more often, and thus encourage the user to raise his level of glucose to a more acceptable level. Once the glucose level returns to an acceptable level, the system can adjust the target interaction rate accordingly.

In the above exemplary embodiment, the system can include a multiplier for adjusting target levels of user interaction, wherein the predetermined target rate of interaction is multiplied by a predetermined amount according to the condition reached. In one exemplary embodiment, a multiplier can be associated with a predetermined target level, such as for example the "critical" target level. In another exemplary embodiment, a multiplier can be associated with a specific condition, or analyte level of the user, such as when the user is in danger of becoming hypoglycemic.

In another exemplary embodiment, the system can adjust the rate of interaction according to predicted future analyte levels. For example, the analyte monitoring system can predict the future analyte level of a user by monitoring the present rate of change of the user's analyte level.

A reader device can also optionally include an alarm system. In one exemplary embodiment, the alarm system is triggered when the user's frequency of interaction with the reader device 120 falls below a predetermined target level of interaction. In another exemplary embodiment, the alarm system can be triggered when the user's level of interaction matches the predetermined target level of interaction. In another exemplary embodiment, the alarm system can be triggered when the user's level of interaction is above a predetermined target level of interaction.

The alarm system can contain one or more individual notifications (e.g., prompts, alert, alarms, prompt, pop-up window, banner notification, numeric representation of a current analyte concentration value (e.g., a current glucose value)). Each of the notifications can be individually activated to indicate one or more predetermined target levels of user interaction with the reader device 120. The notifications can be, for example, auditory or visual. Other sensory-stimulating alarm systems can be used, including alarm systems that direct the reader device to heat, cool, vibrate, or produce a mild electrical shock. In some embodiments, the notifications are auditory with a different tone, note or volume indicating different predetermined target levels of user interaction with the reader device 120. In one exemplary embodiment of this disclosure, various tones of the alarm system 26 can indicate varying urgency levels of a user's need to interact with the reader device 120. For example, a high-volume alarm can indicate a "critical" predetermined target level being reached, while a lower volume alarm might indicate that the user's frequency of interaction has fallen below the "acceptable" level of interaction with the reader device. Visual notifications can also use a difference in color or brightness of the display, or indicators on the display, to distinguish between different predetermined target levels of user interaction with the reader device 120. In some embodiments, visual alarms can include visual notification (e.g., alert, alarm, pop-up window, banner notification, etc.) wherein the visual notification includes an alarm condition, or an analyte level measurement associated with the alarm condition. In some embodiments, a "view" can comprise a visual alarm. In some embodiments, an auditory alarm system can be configured so that the volume of the alarm increases over time until the alarm is deactivated.

According to embodiments disclosed herein, below the predetermined target level of interaction, an increase in the determined frequency of interaction corresponds to a first improvement in a metabolic parameter, and above the predetermined target level of interaction, an increase in the determined frequency of interaction corresponds to a second improvement in the metabolic parameter.

In some embodiments, the alarms can be individually activated to encourage user interaction with the reader device 120. For example, a visual notification (e.g., prompt, alert, alarm, pop-up window, banner notification, etc.) can prompt a user to check sensor results GUI 235. In some embodiments, visual notification can depict a numeric representation of a current analyte concentration value (e.g., a current glucose value). In some embodiments, the alarm system can output one notification if the user's determined frequency of interaction is below a predetermined target level of interaction over a period of time, another notification if the determined frequency of interaction is equal to the predetermined target level of interaction over a period of time, and yet another notification if the determined frequency of interaction is greater than the predetermined target level of interaction over a period of time. The period of time can include any reasonable period of time, such as, for example, one day, 7 days, 14 days, a date range, 30 days, 90 days, etc. For example, and not limitation, a user can receive an alert if the frequency of user interaction is below a predetermined target level of interaction. An alert can include a visual message such as, for example, "Check Glucose Level," to encourage the user to increase the frequency of user interaction. Similarly, a user can receive a prompt if the frequency of user interaction is equal to a predetermined target level of interaction. A prompt can include a visual message such as, for example, "Keep up the good work," so as to encourage the user to maintain or increase their frequency of interaction. Similarly, a user can receive a prompt if the frequency of user interaction is above a predetermined target level of interaction. A prompt can include a visual message such as, for example, "Great job," so that the user continues to maintain their frequency of interaction. In some embodiments, a user can receive visual notification depicting a numeric representation of a current analyte concentration value (e.g., a current glucose value), a visual notification indicating the user's frequency of interaction and/or the predetermined target level of interaction for all three scenarios. According to disclosed embodiments, visual notification can be accompanied by auditory notifications such as those described herein.

In certain embodiments, alarms can be activated if a predetermined time period has elapsed since the last user interaction. For example, and not limitation, a software on the reader device can record a time corresponding to a user's first operation of the reader device and the user's subsequent, second operation of the reader device. Thereafter, the software can calculate a time elapsed between the user's first and second interactions and determine a frequency of interaction over a time period based on user operation of the reader device. If the calculated time elapsed is equal to or greater than a predetermined period of time, the reader device can output a notification to the user, as described herein. In some embodiments, a notification can be an alert if the determined frequency of interaction is below a predetermined target level of interaction and the notification can be a prompt if the determined frequency of interaction is above the predetermined target level of interaction.

According to embodiments, a software on the reader device can record a time corresponding to a user's first operation of the reader device. Thereafter, the software can calculate a time elapsed since the user's first interactions and output a notification to the user for subsequent user interaction corresponding to a determined frequency of interaction. In some embodiments, a notification can be output if a second user interaction is not recorded in the calculated time elapsed.

For example, and not limitation, if a user has not interacted with the reader device 120 (e.g., checked their current glucose value), alarms such as those described above can be active. A person of ordinary skill in the art would understand predetermined time period to include any appropriate period of time, such as, for example, 10 minutes, 15 minutes, 30 minutes, 45 minutes, 60 minutes, 90 minutes, 120 minutes, etc. In another embodiment, visual notification of a current glucose value is activated regardless of frequency of user interaction. In some embodiments, the period of time can be programmed (or user modifiable) to vary during the course of the day or week (work week vs. weekend), with these rates being easily adjustable to account for events or changes, such as, during sick days, times of high activity, or other times when more frequent interactions should be encouraged (e.g., during period of hyper- or hypo-glycemia). In some embodiments, the period of time can be programmed (or user modifiable) based user-determined goals or targets.

In some embodiments, the notifications can be automatically deactivated after a predetermined time period. In other embodiments, the alarms can be configured to deactivate only when the user interacts with a reader device.

In some embodiments, the notifications can only be activated if the user's metabolic parameter is above or below a predetermined level. Exemplary metabolic parameters can include HbA1c, time in target blood sugar range, time in hyperglycemia, time in hypoglycemia, or time above or below other blood glucose levels. In some embodiments, notifications can only be activated if the user's HbA1c level is above, for example, and not limitation, 5.5%, above 6.5%, or any other suitable range. An HbA1c level below 5.5% is generally considered normal, between 5.5-6.5% implies higher risk of diabetes (e.g. prediabetes), and above 6.5% implies diabetes. In some embodiments, the HbA1c level above which notifications are triggered is adjustable (e.g., by the user, HCP, etc.). In some embodiments, notification can only be activated if the user's time in target blood sugar range is below a target range as defined by the International Consensus Standards on Time In Ranges, or as known to a person of ordinary skill in the art. For example, and not limitation, for type 1 and type 2 diabetic patients, notifications can only be activated if a user's time in the target blood sugar range of 70-180 mg/dl is below 16 hours and 48 minutes per day, or 14 hours and 24 minutes per day for users under the age of 25 years. Similarly, for older or higher risk type 1 and type 2 diabetic patients, notifications can only be activated if a user's time in the target blood sugar range of 70-180 mg/dl is below 12 hours per day. For pregnant type 1 diabetic patients, notifications can only be activated if a user's time in the target blood sugar range of 63-140 mg/dl is below 16 hours and 48 minutes per day. For pregnant type 2 diabetic patients, notifications can only be activated if a user's time in the target blood sugar range of 63-140 mg/dl is below 21 hours and 36 minutes per day. In some embodiments, other minimum time thresholds and/or blood glucose ranges can be used to trigger notifications, consistent with the knowledge of a person of ordinary skill in the art.

Figure 12B:
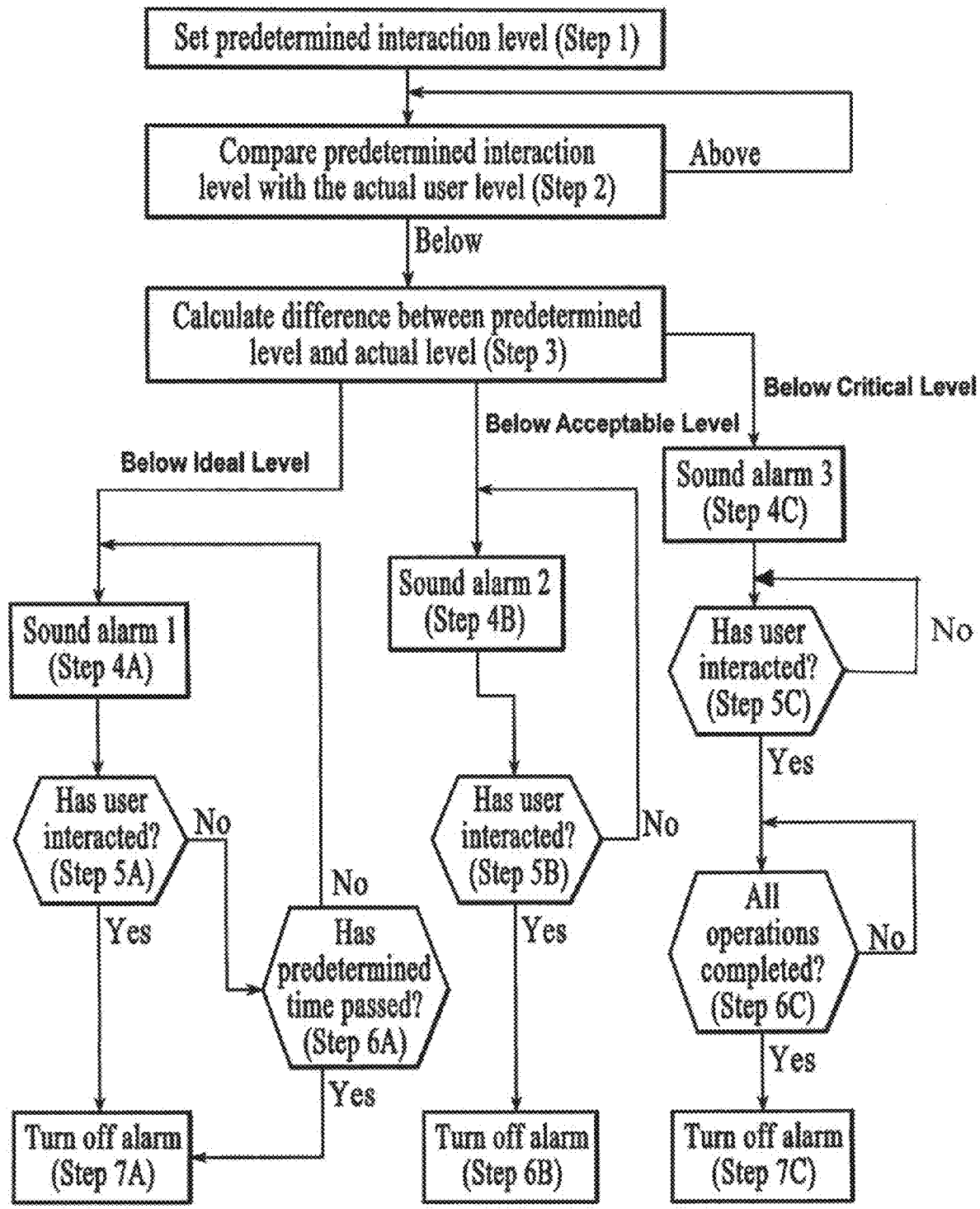

FIG. 12B shows a chart according to an exemplary embodiment of the analyte monitoring system of this disclosure. As shown in Step 1 of FIG. 12B, the predetermined target level of interaction is set. As discussed above, this level can be set by a user, an HCP, any other authorized person, or can automatically change depending on the factors discussed above. Next, in Step 2, the predetermined target level of user interaction is compared to the actual level of user interaction. If the user's actual level of interaction is above the predetermined target level, the system can simply wait. However, if the user's actual level of interaction falls below the target level, the system moves on to Step 3. In Step 3, the system calculates the difference between the actual level of user interaction and the predetermined target level.

In the exemplary embodiment shown in FIG. 12B, there are three levels of user interaction, the "ideal," the "acceptable" and the "critical" level of interaction. In this exemplary embodiment, if the user's actual level of interaction falls below the "ideal" target level of user interaction, the user can be prompted to interact with the device (Step 4A). In one exemplary embodiment, the device will sound a low volume alarm for a predetermined period of time. That is, in Step 5A, the device will determine if the user has interacted with the device, and if the user has interacted, the alarm is turned off (Step 7A). As described above, the user can interact with the device by pressing a button or the like. If the user has not interacted with the device, the device determines whether a predetermined period of time has passed (Step 6A), and if it has, turns off the alarm.

Similarly, if the user's actual level of interaction falls below the "acceptable" target level of interaction, the system will prompt the user to interact with the device, by sounding an alarm or the like (Step 4B). In this example, as shown in Steps 5B and 6B, the alarm will not be turned off until the user has acknowledged the alarm, by pressing a button or the like.

If the user's actual level of interaction falls below the "critical" target level of interaction, the system will set off a third alarm (Step 4C). Similar to the "acceptable" target level, the alarm will not be turned off until the user has acknowledged the alarm (Step 5C). Additionally, to silence an alarm corresponding to the "critical" target level of interaction, the user can be required to perform a series of operations (Step 6C). Once the user completes the series of operations, the alarm is turned off (Step 7C).

One of ordinary skill in the art will understand that the analyte monitoring system of FIG. 12B is simply one possible example of the system according to this disclosure. Steps other than those described in FIG. 6 can be included in the analyte monitoring system, and similarly, the system does not have to include all of the steps shown in FIG. 12B. As such, FIG. 12B should not limit this disclosure in any way, and is simply provided as one example of an analyte monitoring system according to an embodiment of this disclosure.

In one exemplary embodiment, the memory 225 can be used to store the history of user interaction with the reader device, among other data. The memory 225 can also be useful to store data that can be downloaded to a computer or other data storage device in a user's home, at an HCP's office, etc., for evaluation of trends in analyte levels, uploaded to a trusted computer system 180.

In one exemplary embodiment, the HCP can use the recorded history of interaction to modify the treatment of the user. The memory can also store behavior variables, such as events, together with the data of the particular event. These behavior variables can be generated either automatically by the reader device or can, alternatively, be input by the user. In an exemplary embodiment, the user can also edit the event history. Examples of events can include things such as the user's activity level, state of health, medication (e.g., insulin) dosages, meals or any other event that can have an effect on the assessment of a treatment approach and recommendations for treatment modifications of the user.

Additional embodiments of systems and methods for monitoring and analyzing frequency of interaction are described in U.S. Pat. No. 10,856,785, which is incorporated herein by reference in its entirety.

Example Embodiments of Digital Interfaces for Analyte Monitoring Systems

Described herein are example embodiments of digital interfaces for analyte monitoring systems. In accordance with the disclosed subject matter, a digital interface can comprise a series of instructions, routines, subroutines, and/or algorithms, such as software and/or firmware stored in a non-transitory memory, executed by one or more processors of one or more devices in an analyte monitoring system, wherein the instructions, routines, subroutines, or algorithms are configured to enable certain functions and inter-device communications. As an initial matter, it will be understood by those of skill in the art that the digital interfaces described herein can comprise instructions stored in a non-transitory memory of a sensor control device 102, reader device 120, local computer system 170, trusted computer system 180, and/or any other device or system that is part of, or in communication with, analyte monitoring system 100, as described with respect to FIGS. 1, 2A, and 2B. These instructions, when executed by one or more processors of the sensor control device 102, reader device 120, local computer system 170, trusted computer system 180, or other device or system of analyte monitoring system 100, cause the one or more processors to perform the method steps described herein. Those of skill in the art will further recognize that the digital interfaces described herein can be stored as instructions in the memory of a single centralized device or, in the alternative, can be distributed across multiple discrete devices in geographically dispersed locations.

Example Embodiments of Methods for Data Backfilling

Example embodiments of methods for data backfilling in an analyte monitoring system will now be described. In accordance with the disclosed subject matter, gaps in analyte data and other information can result from interruptions to communication links between various devices in an analyte monitoring system 100. These interruptions can occur, for example, from a device being powered off (e.g., a user's smart phone runs out of battery), or a first device temporarily moving out of a wireless communication range from a second device (e.g., a user wearing sensor control device 102 inadvertently leaves her smart phone at home when she goes to work). As a result of these interruptions, reader device 120 may not receive analyte data and other information from sensor control device 102. It would thus be beneficial to have a robust and flexible method for data backfilling in an analyte monitoring system to ensure that once a communication link is re-established, each analyte monitoring device can receive a complete set of data, as intended.

Figure 6A:
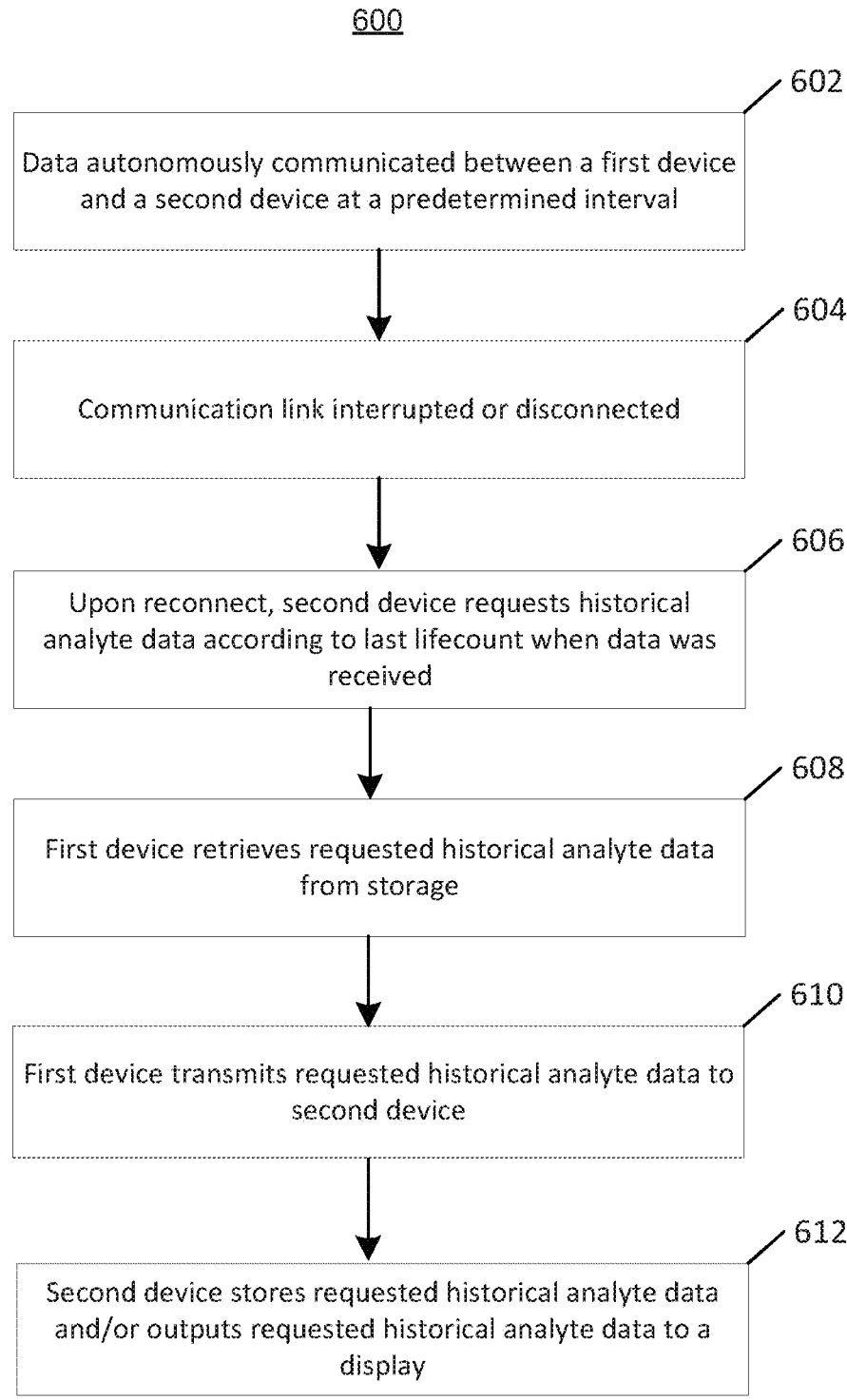
FIGS. 6A and 6B are flow diagrams depicting example embodiments of methods for data backfilling in an analyte monitoring system.

FIG. 6A is a flow diagram depicting an example embodiment of a method 600 for data backfilling in an analyte monitoring system. In accordance with the disclosed subject matter, method 600 can be implemented to provide data backfilling between a sensor control device 102 and a reader device 120. At Step 602, analyte data and other information is autonomously communicated between a first device and a second device at a predetermined interval. In some embodiments, the first device can be a sensor control device 102, and the second device can be a reader device 120, as described with respect to FIGS. 1, 2A, and 2B. In accordance with the disclosed subject matter, analyte data and other information can include, but is not limited to, one or more of: data indicative of an analyte level in a bodily fluid, a rate-of-change of an analyte level, a predicted analyte level, a low or a high analyte level alert condition, a sensor fault condition, or a communication link event. According to another aspect of the embodiments, autonomous communications at a predetermined interval can comprise streaming analyte data and other information according to a standard wireless communication network protocol, such as a Bluetooth or Bluetooth Low Energy protocol, at one or more predetermined rates (e.g., every minute, every five minutes, every fifteen minutes, etc.). In some embodiments, different types of analyte data or other information can be autonomously communicated between the first and second devices at different predetermined rates (e.g., historical glucose data every 5 minutes, current glucose value every minute, etc.).

At Step 604, a disconnection event or condition occurs that causes an interruption to the communication link between the first device and the second device. As described above, the disconnection event can result from the second device (e.g., reader device 120, smart phone, etc.) running out of battery power or being powered off manually by a user. A disconnection event can also result from the first device being moved outside a wireless communication range of the second device, from the presence of a physical barrier that obstructs the first device and/or the second device, or from anything that otherwise prevents wireless communications from occurring between the first and second devices.

At Step 606, the communication link is re-established between the first device and the second device (e.g., the first device comes back into the wireless communication range of the second device). Upon reconnection, the second device requests historical analyte data according to a last lifecount metric for which data was received. In accordance with the disclosed subject matter, the lifecount metric can be a numeric value that is incremented and tracked on the second device in units of time (e.g., minutes), and is indicative of an amount of time elapsed since the sensor control device was activated. For example, in some embodiments, after the second device (e.g., reader device 120, smart phone, etc.) re-establishes a Bluetooth wireless communication link with the first device (e.g., sensor control device 120), the second device can determine the last lifecount metric for which data was received. Then, according to some embodiments, the second device can send to the first device a request for historical analyte data and other information having a lifecount metric greater than the determined last lifecount metric for which data was received.

In some embodiments, the second device can send a request to the first device for historical analyte data or other information associated with a specific lifecount range, instead of requesting historical analyte data associated with a lifecount metric greater than a determined last lifecount metric for which data was received.

At Step 608, upon receiving the request, the first device retrieves the requested historical analyte data from storage (e.g., non-transitory memory of sensor control device 102), and subsequently transmits the requested historical analyte data to the second device at Step 610. At Step 612, upon receiving the requested historical analyte data, the second device stores the requested historical analyte data in storage (e.g., non-transitory memory of reader device 120). In accordance with the disclosed subject matter, when the requested historical analyte data is stored by the second device, it can be stored along with the associated lifecount metric. In some embodiments, the second device can also output the requested historical analyte data to a display of the second device, such as, for example to a glucose trend graph of a sensor results GUI, such as those described with respect to FIGS. 2D to 2I. For example, in some embodiments, the requested historical analyte data can be used to fill in gaps in a glucose trend graph by displaying the requested historical analyte data along with previously received analyte data.

Furthermore, those of skill in the art will appreciate that the method of data backfilling can be implemented between multiple and various devices in an analyte monitoring system, wherein the devices are in wired or wireless communication with each other.

Figure 6B:
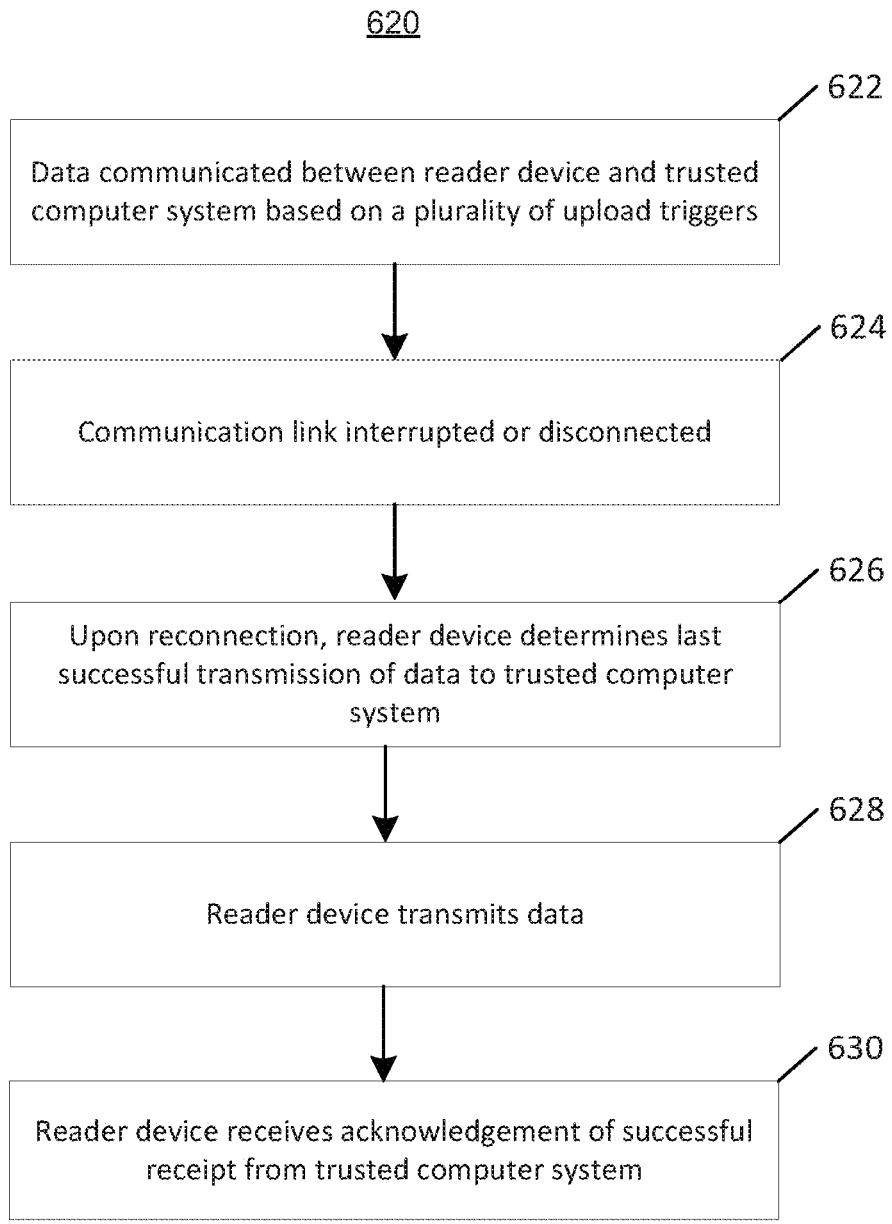

FIG. 6B is a flow diagram depicting another example embodiment of a method 620 for data backfilling in an analyte monitoring system. In accordance with the disclosed subject matter, method 620 can be implemented to provide data backfilling between a reader device 120 (e.g., smart phone, dedicated reader) and a trusted computer system 180, such as, for example, a cloud-based platform for generating reports. At Step 622, analyte data and other information is communicated between reader device 120 and trusted computer system 180 based on a plurality of upload triggers. In accordance with the disclosed subject matter, analyte data and other information can include, but are not limited to, one or more of: data indicative of an analyte level in a bodily fluid (e.g., current glucose level, historical glucose data), a rate-of-change of an analyte level, a predicted analyte level, a low or a high analyte level alert condition, information logged by the user, information relating to sensor control device 102, alarm information (e.g., alarm settings), wireless connection events, and reader device settings, to name a few.

According to another aspect of the embodiments, the plurality of upload triggers can include (but is not limited to) one or more of the following: activation of sensor control device 102; user entry or deletion of a note or log entry; a wireless communication link (e.g., Bluetooth) reestablished between reader device 120 and sensor control device 102; alarm threshold changed; alarm presentation, update, or dismissal; internet connection re-established; reader device 120 restarted; a receipt of one or more current glucose readings from sensor control device 102; sensor control device 120 terminated; signal loss alarm presentation, update, or dismissal; signal loss alarm is toggled on/off; view of sensor results screen GUI; or user sign-in into cloud-based platform.

According to another aspect of the embodiments, in order to track the transmission and receipt of data between devices, reader device 120 can "mark" analyte data and other information that is to be transmitted to trusted computer system 180. In some embodiments, for example, upon receipt of the analyte data and other information, trusted computer system 180 can send a return response to reader device 120, to acknowledge that the analyte data and other information has been successfully received. Subsequently, reader device 120 can mark the data as successfully sent. In some embodiments, the analyte data and other information can be marked by reader device 120 both prior to being sent and after receipt of the return response. In other embodiments, the analyte data and other information can be marked by reader device 120 only after receipt of the return response from trusted computer system 180.

Referring to FIG. 6B, at Step 624, a disconnection event occurs that causes an interruption to the communication link between reader device 120 and trusted computer system 180. For example, the disconnection event can result from the user placing the reader device 120 into "airplane mode" (e.g., disabling of the wireless communication modules), from the user powering off the reader device 120, or from the reader device 120 moving outside of a wireless communication range.

At Step 626, the communication link between reader device 120 and trusted computer system 180 (as well as the internet) is re-established, which is one of the plurality of upload triggers. Subsequently, reader device 120 determines the last successful transmission of data to trusted computer system 180 based on the previously marked analyte data and other information sent. Then, at Step 628, reader device 120 can transmit analyte data and other information not yet received by trusted computer system 180. At Step 630, reader device 120 receives acknowledgement of successful receipt of analyte data and other information from trusted computer system 180.

Although FIG. 6B is described above with respect to a reader in communication with a trusted computer system, those of skill in the art will appreciate that the data backfilling method can be applied between other devices and computer systems in an analyte monitoring system (e.g., between a reader and a local computer system, between a reader and a medical delivery device, between a reader and a wearable computing device, etc.). These embodiments, along with their variations and permutations, are fully within the scope of this disclosure.

In addition to data backfilling, example embodiments of methods for aggregating disconnect and reconnect events for wireless communication links in an analyte monitoring system are described. In accordance with the disclosed subject matter, there can be numerous and wide-ranging causes for interruptions to wireless communication links between various devices in an analyte monitoring system. Some causes can be technical in nature (e.g., a reader device is outside a sensor control device's wireless communication range), while other causes can relate to user behavior (e.g., a user leaving his or her reader device at home). In order to improve connectivity and data integrity in analyte monitoring systems, it would therefore be beneficial to gather information regarding the disconnect and reconnect events between various devices in an analyte monitoring system.

Figure 6C:
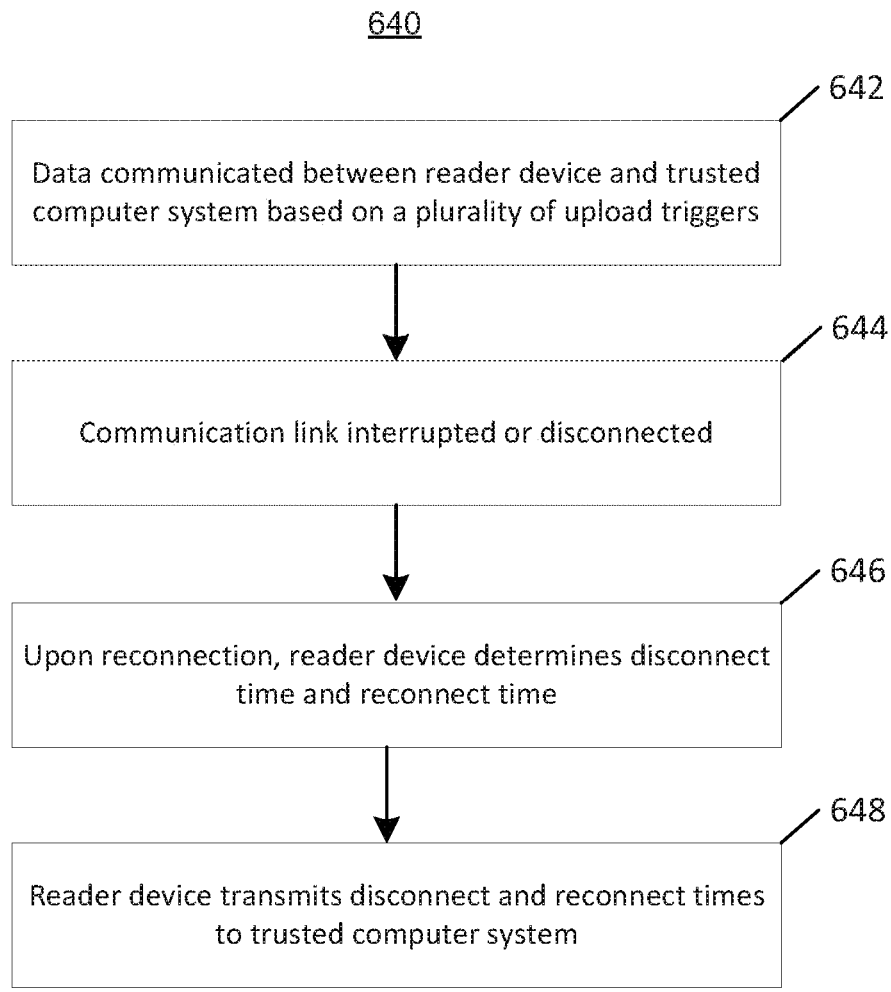
FIG. 6C is a flow diagram depicting an example embodiment of a method for aggregating disconnect and reconnect events in an analyte monitoring system.

FIG. 6C is a flow diagram depicting an example embodiment of a method 640 for aggregating disconnect and reconnect events for wireless communication links in an analyte monitoring system. In some embodiments, for example, method 640 can be used to detect, log, and upload to trusted computer system 180, Bluetooth or Bluetooth Low Energy disconnect and reconnect events between a sensor control device 102 and a reader device 120. In accordance with the disclosed subject matter, trusted computer system 180 can aggregate disconnect and reconnect events transmitted from a plurality of analyte monitoring systems. The aggregated data can then by analyzed to determine whether any conclusions can be made about how to improve connectivity and data integrity in analyte monitoring systems.

At Step 642, analyte data and other information are communicated between reader device 120 and trusted computer system 180 based on a plurality of upload triggers, such as those previously described with respect to method 620 of FIG. 6B. At Step 644, a disconnection event occurs that causes an interruption to the wireless communication link between sensor control device 102 and reader device 120. Example disconnection events can include, but are not limited to, a user placing the reader device 120 into "airplane mode," the user powering off the reader device 120, the reader device 120 running out of power, the sensor control device 102 moving outside a wireless communication range of the reader devices 120, or a physical barrier obstructing the sensor control device 102 and/or the reader device 120, to name only a few.

Referring still to FIG. 6C, at Step 646, the wireless communication link between the sensor control device 102 and reader device 120 is re-established, which is one of the plurality of upload triggers. Subsequently, reader device 120 determines a disconnect time and a reconnect time, wherein the disconnect time is the time that the interruption to the wireless communication link began, and the reconnect time is the time that the wireless communication link between the sensor control device 102 and reader device 120 is re-established. According to some embodiments, the disconnection and reconnection times can also be stored locally in an event log on reader device 120. At Step 648, reader device 120 transmits the disconnect and reconnect times to trusted computer system 180.

According to some embodiments, the disconnect and reconnect times can be stored in non-transitory memory of trusted computer system 180, such as in a database, and aggregated with the disconnect and reconnect times collected from other analyte monitoring systems. In some embodiments, the disconnect and reconnect times can also be transmitted to and stored on a different cloud-based platform or server from trusted computer system 180 that stores analyte data. In still other embodiments, the disconnect and reconnect times can be anonymized.

In addition, those of skill in the art will recognize that method 640 can be utilized to collect disconnect and reconnect times between other devices in an analyte monitoring system, including, for example: between reader device 120 and trusted computer system 180; between reader device 120 and a wearable computing device (e.g., smart watch, smart glasses); between reader device 120 and a medication delivery device (e.g., insulin pump, insulin pen); between sensor control device 102 and a wearable computing device; between sensor control device 102 and a medication delivery device; and any other combination of devices within an analyte monitoring system. Those of skill in the art will further appreciate that method 640 can be utilized to analyze disconnect and reconnect times for different wireless communication protocols, such as, for example, Bluetooth or Bluetooth Low Energy, NFC, 802.11x, UHF, cellular connectivity, or any other standard or proprietary wireless communication protocol.

Example Embodiments of Improved Expired/Failed Sensor Transmissions

Example embodiments of methods for improved expired and/or failed sensor transmissions in an analyte monitoring system will now be described. In accordance with the disclosed subject matter, expired or failed sensor conditions detected by a sensor control device 102 can trigger alerts on reader device 120. However, if the reader device 120 is in "airplane mode," powered off, outside a wireless communication range of sensor control device 102, or otherwise unable to wirelessly communicate with the sensor control device 102, then the reader device 120 may not receive these alerts. This can cause the user to miss information such as, for example, the need to promptly replace a sensor control device 102. Failure to take action on a detected sensor fault can also lead to the user being unaware of adverse glucose conditions (e.g., hypoglycemia and/or hyperglycemia) due to a terminated sensor.

Figure 7:
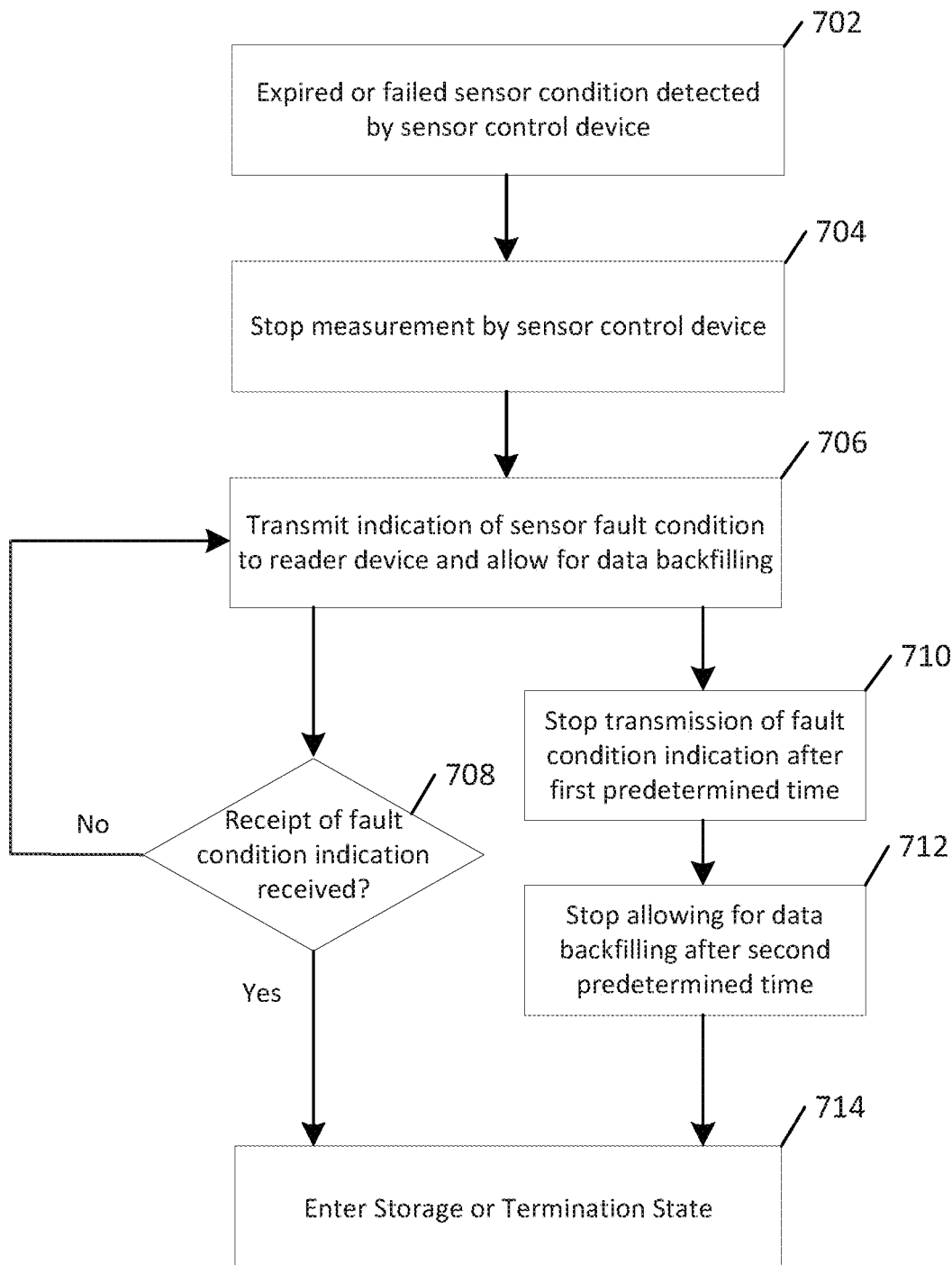
FIG. 7 is a flow diagram depicting an example embodiment of a method for failed or expired sensor transmissions in an analyte monitoring system.

FIG. 7 is a flow diagram depicting an example embodiment of a method 700 for improved expired or failed sensor transmissions in an analyte monitoring system. In accordance with the disclosed subject matter, method 700 can be implemented to provide for improved sensor transmissions by a sensor control device 102 after an expired or failed sensor condition has been detected. At Step 702, an expired or failed sensor condition is detected by sensor control device 102. In some embodiments, the sensor fault condition can comprise one or both of a sensor insertion failure condition or a sensor termination condition. According to some embodiments, for example, a sensor insertion failure condition or a sensor termination condition can include, but is not limited to, one or more of the following: a FIFO overflow condition detected, a sensor signal below a predetermined insertion failure threshold, moisture ingress detected, an electrode voltage exceeding a predetermined diagnostic voltage threshold, an early signal attenuation (ESA) condition, or a late signal attenuation (LSA) condition, to name a few.

Referring again to FIG. 7, at Step 704, sensor control device 102 stops acquiring measurements of analyte levels from the analyte sensor in response to the detection of the sensor fault condition. At Step 706, sensor control device 102 begins transmitting an indication of a sensor fault condition to reader device 120, while also allowing for the reader device 120 to connect to the sensor control device 102 for purposes of data backfilling. In accordance with the disclosed subject matter, the transmission of the indication of the sensor fault condition can comprise transmitting a plurality of Bluetooth or Bluetooth Low Energy advertising packets, each of which can include the indication of the sensor fault condition. In some embodiments, the plurality of Bluetooth or BLE advertising packets can be transmitted repeatedly, continuously, or intermittently. Those of skill in the art will recognize that other modes of wirelessly broadcasting or multicasting the indication of the sensor fault condition can be implemented. According to another aspect of the embodiments, in response to receiving the indication of the sensor fault condition, reader device 120 can visually display an alert or prompt for a confirmation by the user.

At Step 708, sensor control device 102 can be configured to monitor for a return response or acknowledgment of receipt of the indication of the sensor fault condition from reader device 120. In some embodiments, for example, a return response or acknowledgement of receipt can be generated by reader device 120 when a user dismisses an alert on the reader device 120 relating to the indication of the sensor fault condition, or otherwise responds to a prompt for confirmation of the indication of the sensor fault condition. If a return response or acknowledgement of receipt of the indication of the sensor fault condition is received by sensor control device 102, then at Step 714, sensor control device 102 can enter either a storage state or a termination state. According to some embodiments, in the storage state, the sensor control device 102 is placed in a low-power mode, and the sensor control device 102 is capable of being re-activated by a reader device 120. By contrast, in the termination state, the sensor control device 102 cannot be re-activated and must be removed and replaced.

If a receipt of the fault condition indication is not received by sensor control device 102, then at Step 710, the sensor control device 102 will stop transmitting the fault condition indication after a first predetermined time period. In some embodiments, for example, the first predetermined time period can be one of: one hour, two hours, five hours, etc. Subsequently, at Step 712, if a receipt of the fault condition indication is still not received by sensor control device 102, then at Step 712, the sensor control device 102 will also stop allowing for data backfilling after a second predetermined time period. In some embodiments, for example, the second predetermined time period can be one of: twenty-four hours, forty-eight hours, etc. Sensor control device 102 then enters a storage state or a termination state at Step 714.

By allowing sensor control device 102 to continue transmissions of sensor fault conditions for a predetermined time period, the embodiments of this disclosure mitigate the risk of unreceived sensor fault alerts. In addition, although the embodiments described above are in reference to a sensor control device 102 in communication with a reader device 120, those of skill in the art will recognize that indications of sensor fault conditions can also be transmitted between a sensor control device 102 and other types of mobile computing devices, such as, for example, wearable computing devices (e.g., smart watches, smart glasses) or tablet computing devices.

Example Embodiments of Data Merging in Analyte Monitoring Systems

Example embodiments of methods for merging data received from one or more analyte monitoring systems will now be described. As described earlier with respect to FIG. 1, a trusted computer system 180, such as a cloud-based platform, can be configured to generate various reports based on received analyte data and other information from a plurality of reader devices 120 and sensor control devices 102. A large and diverse population of reader devices and sensor control devices, however, can give rise to complexities and challenges in generating reports based on the received analyte data and other information. For example, a single user may have multiple reader devices and/or sensor control devices, either simultaneously or serially over time, each of which can comprise different versions. This can lead to further complications in that, for each user, there may be sets of duplicative and/or overlapping data. It would therefore be beneficial to have methods for merging data at a trusted computer system for purposes of report generation.

Figure 8A:
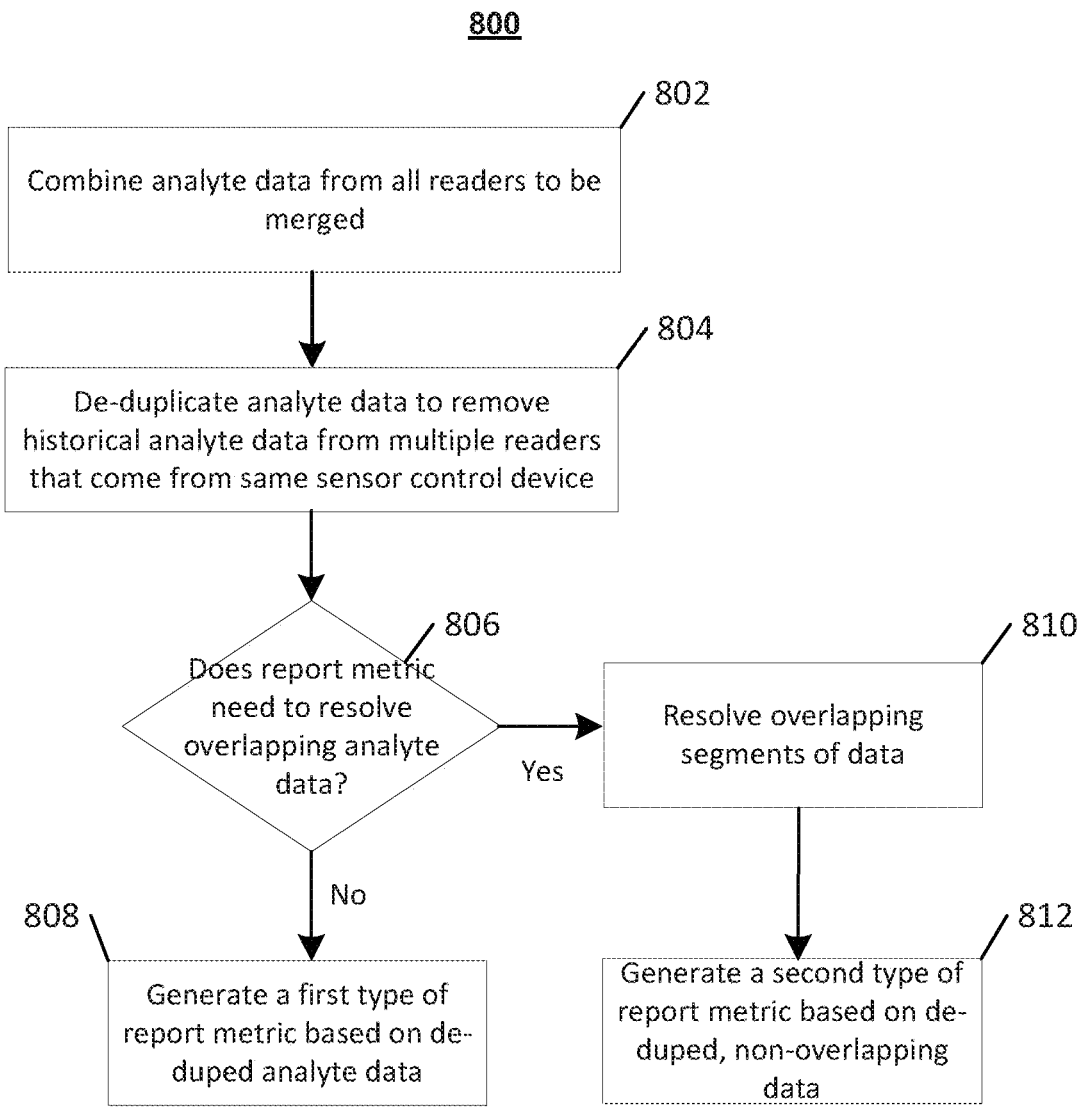
FIGS. 8A and 8B are flow diagrams depicting example embodiments of methods for data merging in an analyte monitoring system.

FIG. 8A is a flow diagram depicting an example embodiment of a method 800 for merging data associated with a user and generating one or more report metrics, wherein the data originates from multiple reader devices and multiple sensor control devices. In accordance with the disclosed subject matter, method 800 can be implemented to merge analyte data in order to generate different types of report metrics utilized in various reports. At Step 802, data is received from one or more reader devices 120 and combined for purposes of merging. At Step 804, the combined data is then de-duplicated to remove historical data from multiple readers originating from the same sensor control device. In accordance with the disclosed subject matter, the process of de-duplicating data can include (1) identifying or assigning a priority associated with each reader device from which analyte data is received, and (2) in the case where there is "duplicate" data, preserving the data associated with the reader device with a higher priority. In some embodiments, for example, a newer reader device (e.g., newer model, having a more recent version of software installed) is assigned a higher priority than an older reader device (e.g., older model, having an older version of software installed). In some embodiments, priority can be assigned by device type (e.g., smart phone having a higher priority over a dedicated reader).

Referring still to FIG. 8A, at Step 806, a determination is made as to whether one or more of the report metrics to be generated requires resolution of overlapping data. If not, at Step 808, a first type of report metric can be generated based on de-duplicated data without further processing. In some embodiments, for example, the first type of report metric can include average glucose levels used in reports, such as a snapshot or monthly summary report (as described with respect to FIGS. 5C and 5D). If it is determined that one or more of the report metrics to be generated requires resolution of overlapping data, then at Step 810, a method for resolving overlapping regions of data is performed. An example embodiment method for resolving overlapping regions of data is described below with respect to FIG. 8B. Subsequently, at Step 812, a second type of report metric based on data that has been de-duplicated and processed to resolve overlapping data segments, is generated. In some embodiments, for example, the second type of report metric can include low glucose event calculations used in reports, such as the daily log report (as described with respect to FIG. 5F).

Figure 8B:
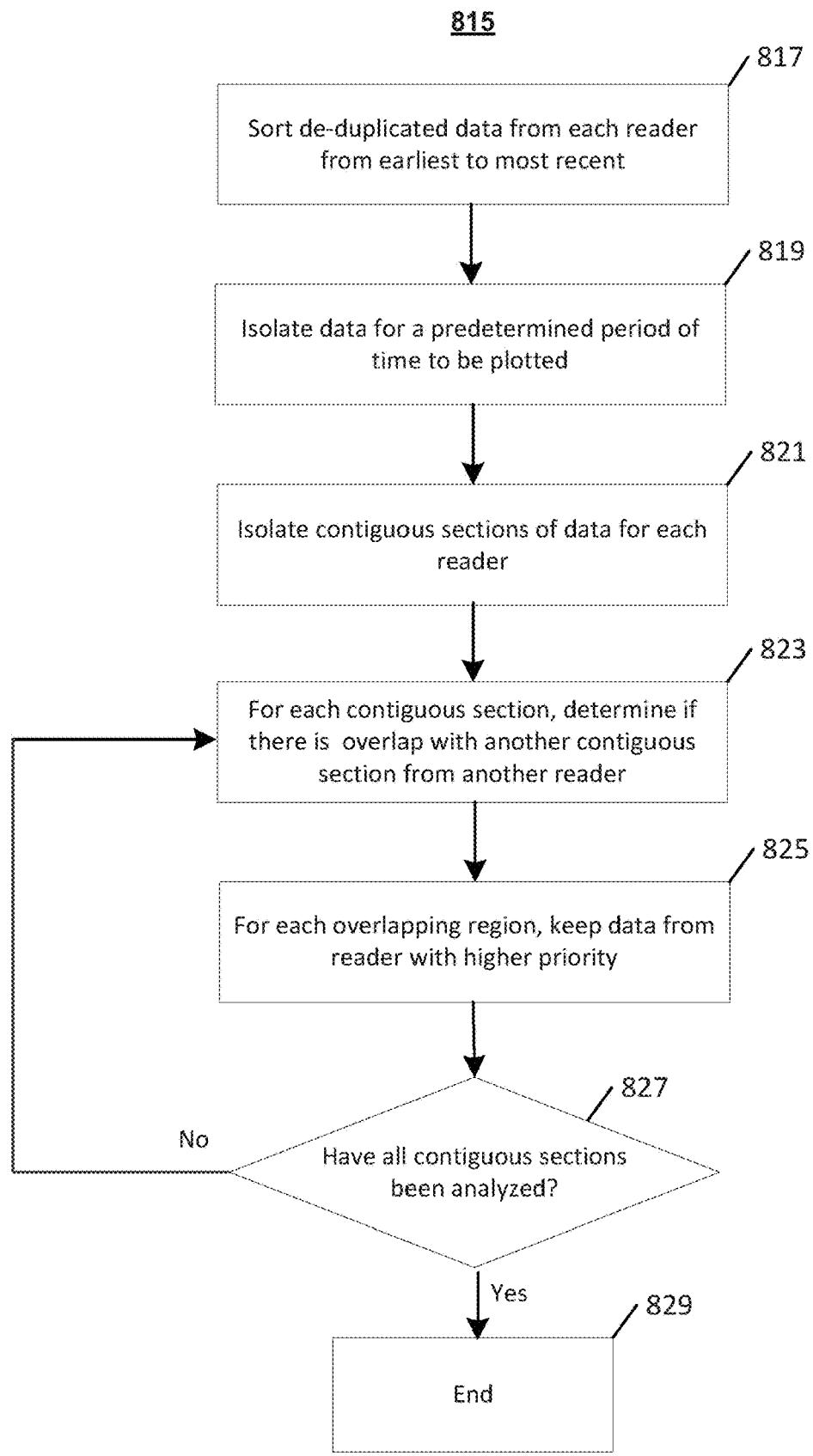

FIG. 8B is a flow diagram depicting an example embodiment of a method 815 for resolving overlapping regions of analyte data, which can be implemented, for example, in Step 810 of method 800, as described with respect to FIG. 8A. At Step 817, the de-duplicated data from each reader (resulting from Step 804 of method 800, as described with respect to FIG. 8A) can be sorted from earliest to most recent. At Step 819, based on the report metric to be generated, the de-duplicated and sorted data is then isolated according to a predetermined period of time. In some embodiments, for example, if the report metric is a graph reflecting glucose values over a specific day, then the de-duplicated and sorted data can be isolated for that specific day. Next, at Step 821, contiguous sections of the de-duplicated and sorted data for each reader device are isolated. In accordance with the disclosed subject matter, non-contiguous data points can be discarded or disregarded (e.g., not used) for purposes of generating report metrics. At Step 823, for each contiguous section of de-duplicated and sorted data of a reader device, a determination is made as to whether there are any overlapping regions with other contiguous sections of de-duplicated and sorted data from other reader devices. At Step 825, for each overlapping region identified, the de-duplicated and sorted data from the reader device with the higher priority is preserved. At Step 827, if it is determined that all contiguous sections have been analyzed according to the previous steps, then method 815 ends at Step 829. Otherwise, method 815 then returns to Step 823 to continue identifying and resolving any overlapping regions between contiguous sections of de-duplicated and sorted data for different reader devices.

FIGS. 8C to 8E are graphs (840, 850, 860) depicting various stages of de-duplicated and sorted data from multiple reader devices, as the data is processed according to method 815 for resolving overlapping regions of data. Referring first to FIG. 8C, graph 840 depicts de-duplicated and sorted data from three different reader devices: a first reader 841 (as reflected by the circular data points), a second reader 842 (as reflected by diamond-shaped data points), and a third reader 843 (as reflected by the square-shaped data points). According to one aspect of graph 840, the data is depicted at Step 821 of method 815, after it has been de-duplicated, sorted, and isolated to a predetermined time period. As can be seen in FIG. 8C, a contiguous section of data for each of the three reader devices (841, 842, and 843) has been identified, and three traces are shown. According to another aspect of the graph 840, non-contiguous points 844 are not included in the three traces.

Referring next to FIG. 8D, graph 850 depicts the data from readers 841, 842, 843 at Step 823 of method 815, wherein three overlapping regions between the contiguous sections of data have been identified: a first overlapping region 851 between all three contiguous sections of data; a second overlapping region 852 between two contiguous sections of data (from reader device 842 and reader device 843); and a third overlapping region 853 between two contiguous sections of data (also from reader device 842 and reader device 843).

FIG. 8E is a graph 860 depicting data at Step 825 of method 815, wherein a single trace 861 indicates the merged, de-duplicated, and sorted data from three reader devices 841, 842, 843 after overlapping regions 851, 852, and 853 have been resolved by using the priority of each reader device. According to graph 860, the order of priority from highest to lowest is: reader device 843, reader device 842, and reader device 841.

Although FIGS. 8C, 8D, and 8E depict three contiguous sections of data with three discrete overlapping regions identified, those of skill in the art will understand that either fewer or more contiguous sections of data (and non-contiguous data points) and overlapping regions are possible. For example, those of skill in the art will recognize that where a user has only two reader devices, there may be fewer contiguous sections of data and overlapping regions, if any at all. Conversely, if a user has five reader devices, those of skill in the art will understand that there may be five contiguous sections of data with three or more overlapping regions.

Example Embodiments of Sensor Transitioning

Example embodiments of methods for sensor transitioning will now be described. In accordance with the disclosed subject matter, as mobile computing and wearable technologies continue to advance at a rapid pace and become more ubiquitous, users are more likely to replace or upgrade their smart phones more frequently. In the context of analyte monitoring systems, it would therefore be beneficial to have sensor transitioning methods to allow a user to continue using a previously activated sensor control device with a new smart phone. In addition, it would also be beneficial to ensure that historical analyte data from the sensor control device could be backfilled to the new smart phone (and subsequently uploaded to the trusted computer system) in a user-friendly and secure manner.

Figure 9A:
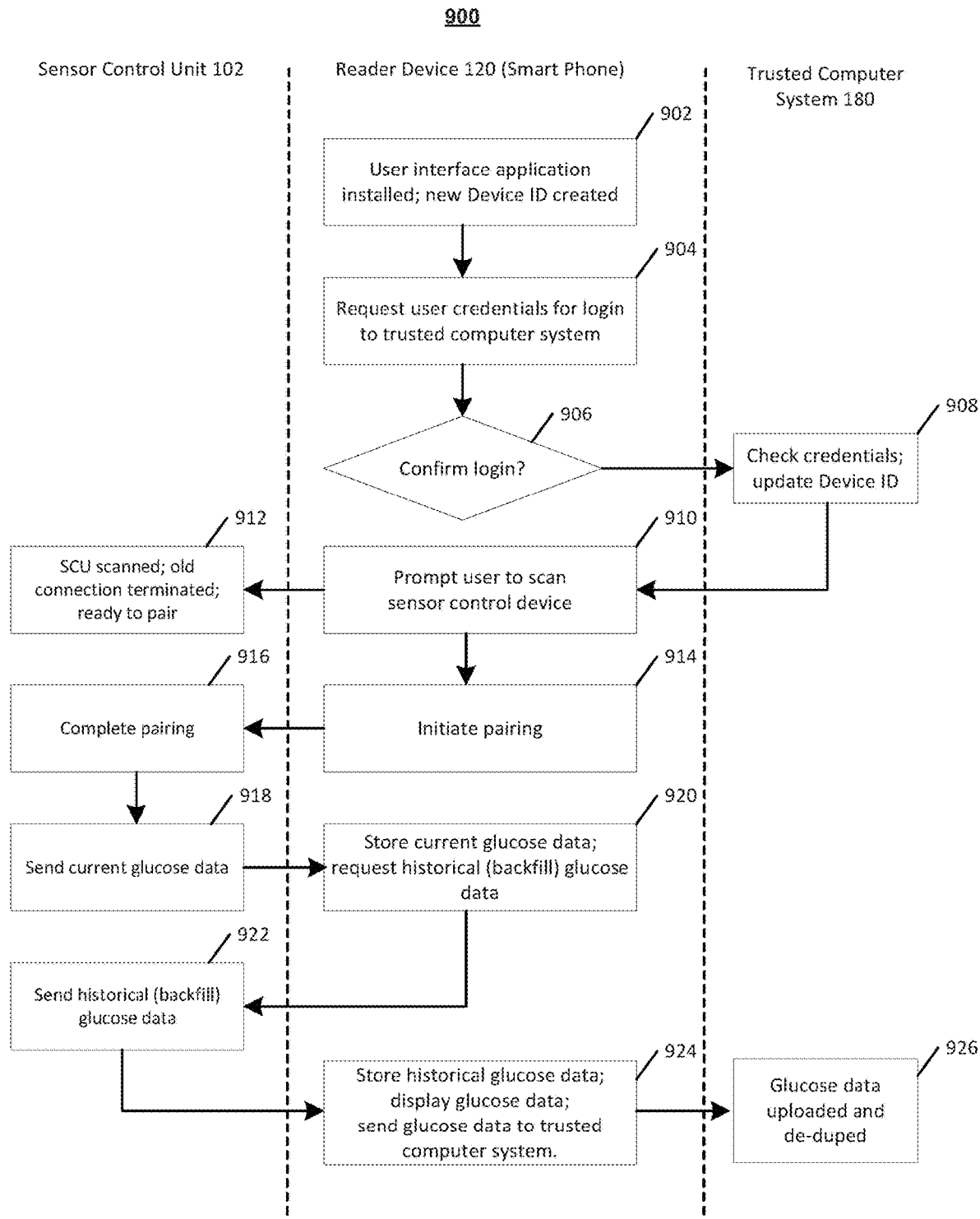
FIG. 9A is a flow diagram depicting an example embodiment of a method for sensor transitioning in an analyte monitoring system.
Figure 9D:
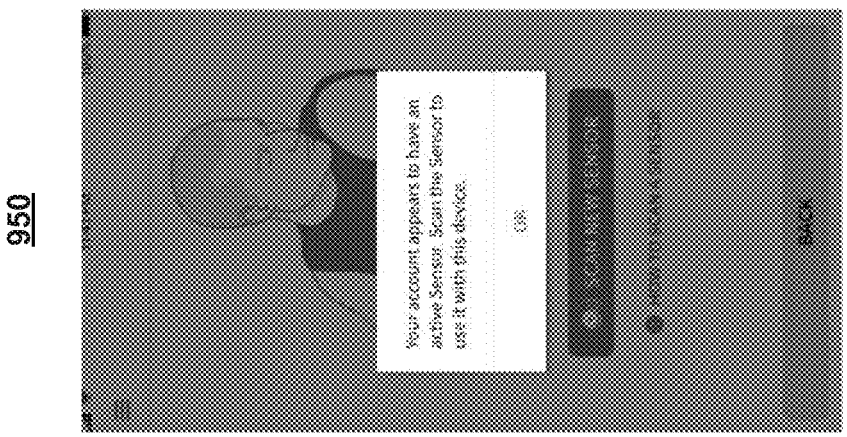
FIGS. 9B to 9D are example embodiments of GUIs to be displayed according to an example embodiment of a method for sensor transitioning in an analyte monitoring system.
Figure 9C:
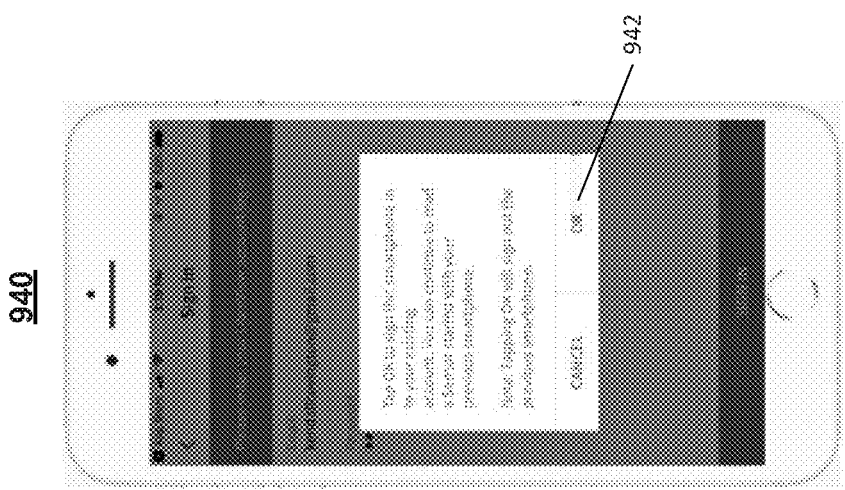
Figure 9B:
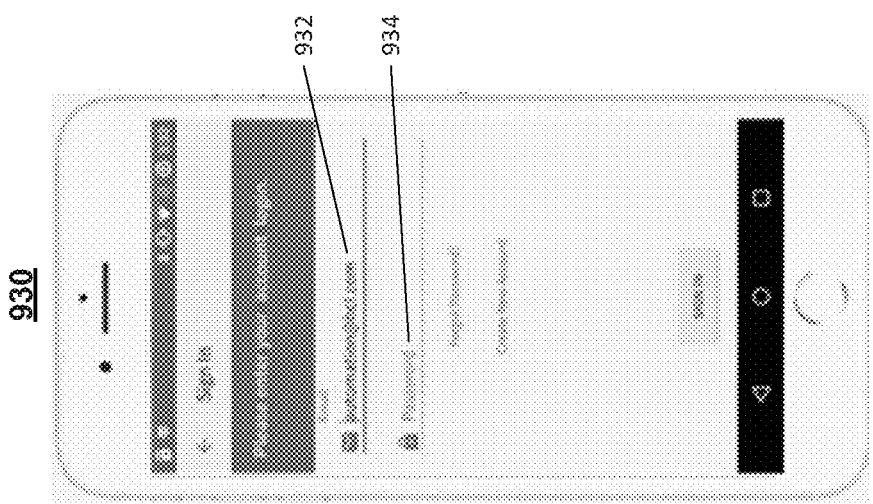

FIG. 9A is a flow diagram depicting an example embodiment of a method 900 for transitioning a sensor control device. In accordance with the disclosed subject matter, method 900 can be implemented in an analyte monitoring system to allow a user to continue using a previously activated sensor control device with a new reader device (e.g., smart phone). At Step 902, a user interface application (e.g., mobile software application or app) is installed on reader device 120 (e.g., smart phone), which causes a new unique device identifier, or "device ID," to be created and stored on reader device 120. At Step 904, after installing and launching the app, the user is prompted to enter their user credentials for purposes of logging into trusted computer system 180 (e.g., cloud-based platform or server). An example embodiment of a GUI 930 for prompting the user to enter their user credentials is shown in FIG. 9B. According to an aspect of the embodiments, GUI 930 can include a username field 932, which can comprise a unique username or an e-mail address, and a masked or unmasked password field 934, to allow the user to enter their password.

Referring again to FIG. 9A, at Step 906, after user credentials are entered into the app, a prompt is displayed requesting user confirmation to login to trusted computer system 180. An example embodiment of GUI 940 for requesting user confirmation to login to trusted computer system 180 is shown in FIG. 9D. According to an aspect of the embodiments, GUI 940 can also include a warning, such as the one shown in FIG. 9D, that confirming the login will cause the user to be logged off from other reader devices (e.g., the user's old smart phone).

If the user confirms login, then at Step 908, the user's credentials are sent to trusted computer system 180 and subsequently verified. In addition, according to some embodiments, the device ID can also be transmitted from the reader device 120 to trusted computer system 180 and stored in a non-transitory memory of trusted computer system 180. According to some embodiments, for example, in response to receiving the device ID, trusted computer system 180 can update a device ID field associated with the user's record in a database.

After the user credentials are verified by trusted computer system 180, at Step 910, the user is prompted by the app to scan the already-activated sensor control device 102. In accordance with the disclosed subject matter, the scan can comprise bringing the reader device 120 in close proximity to sensor control device 102, and causing the reader device 120 to transmit one or more wireless interrogation signals according to a first wireless communication protocol. In some embodiments, for example, the first wireless communication protocol can be a Near Field Communication (NFC) wireless communication protocol. Those of skill in the art, however, will recognize that other wireless communication protocols can be implemented (e.g., infrared, UHF, 802.11x, etc.). An example embodiment of GUI 950 for prompting the user to scan the already-activated sensor control device 102 is shown in FIG. 9D.

Referring still to FIG. 9A, at Step 912, scanning of sensor control device 102 by reader device 120 causes sensor control device 102 to terminate an existing wireless communication link with the user's previous reader device, if there is currently one established. According to an aspect of the embodiments, the existing wireless communication link can comprise a link established according to a second wireless communication protocol that is different from the first wireless communication protocol. In some embodiments, for example, the second wireless communication protocol can be a Bluetooth or Bluetooth Low Energy protocol. Subsequently, sensor control device 102 enters into a "ready to pair" state, in which sensor control device 102 is available to establish a wireless communication link with reader device 120 according to the second wireless communication protocol.

At Step 914, reader device 120 initiates a pairing sequence via the second wireless communication protocol (e.g., Bluetooth or Bluetooth Low Energy) with sensor control device 102. Subsequently, at Step 916, sensor control device 102 completes the pairing sequence with reader device 120. At Step 918, sensor control device 102 can begin sending current glucose data to reader device 120 according to the second wireless communication protocol. In some embodiments, for example, current glucose data can be wirelessly transmitted to reader device 120 at a predetermined interval (e.g., every minute, every two minutes, every five minutes).

Referring still to FIG. 9A, at Step 920, reader device 120 receives and stores current glucose data received from sensor control device 102 in a non-transitory memory of reader device 120. In addition, according to some embodiments, reader device 120 can request historical glucose data from sensor control device 102 for backfilling purposes. According to some embodiments, for example, reader device 120 can request historical glucose data from sensor control device 102 for the full wear duration, which is stored in a non-transitory memory of sensor control device 102. In other embodiments, reader device 120 can request historical glucose data for a specific predetermined time range (e.g., from day 3 to present, from day 5 to present, last 3 days, last 5 days, lifecount>0, etc.). Those of skill will appreciate that other backfilling schemes can be implemented (such as those described with respect to FIGS. 6A and 6B), and are fully within the scope of this disclosure.

Upon receipt of the request at Step 922, sensor control device 102 can retrieve historical glucose data from a non-transitory memory and transmit it to reader device 120. In turn, at Step 924, reader device 120 can store the received historical glucose data in a non-transitory memory. In addition, according to some embodiments, reader device 120 can also display the current and/or historical glucose data in the app (e.g., on a sensor results screen). In this regard, a new reader can display all available analyte data for the full wear duration of a sensor control device. In some embodiments, reader device 120 can also transmit the current and/or historical glucose data to trusted computer system 180. At Step 926, the received glucose data can be stored in a non-transitory memory (e.g., a database) of trusted computer system 180.

In some embodiments, the received glucose data can also be de-duplicated prior to storage in non-transitory memory.

Example Embodiments of Check Sensor and Replace Sensor System Alarms

Example embodiments of autonomous check sensor and replace sensor system alarms, and methods relating thereto, will now be described. In accordance with the disclosed subject matter, certain adverse conditions affecting the operation of the analyte sensor and sensor electronics can be detectable by the sensor control device. For example, an improperly inserted analyte sensor can be detected if an average glucose level measurement over a predetermined period of time is determined to be below an insertion failure threshold. Due to its small form factor and a limited power capacity, however, the sensor control device may not have sufficient alarming capabilities. As such, it would be advantageous for the sensor control device to transmit indications of adverse conditions to another device, such as a reader device (e.g., smart phone), to alert the user of those conditions.

Figure 10A:
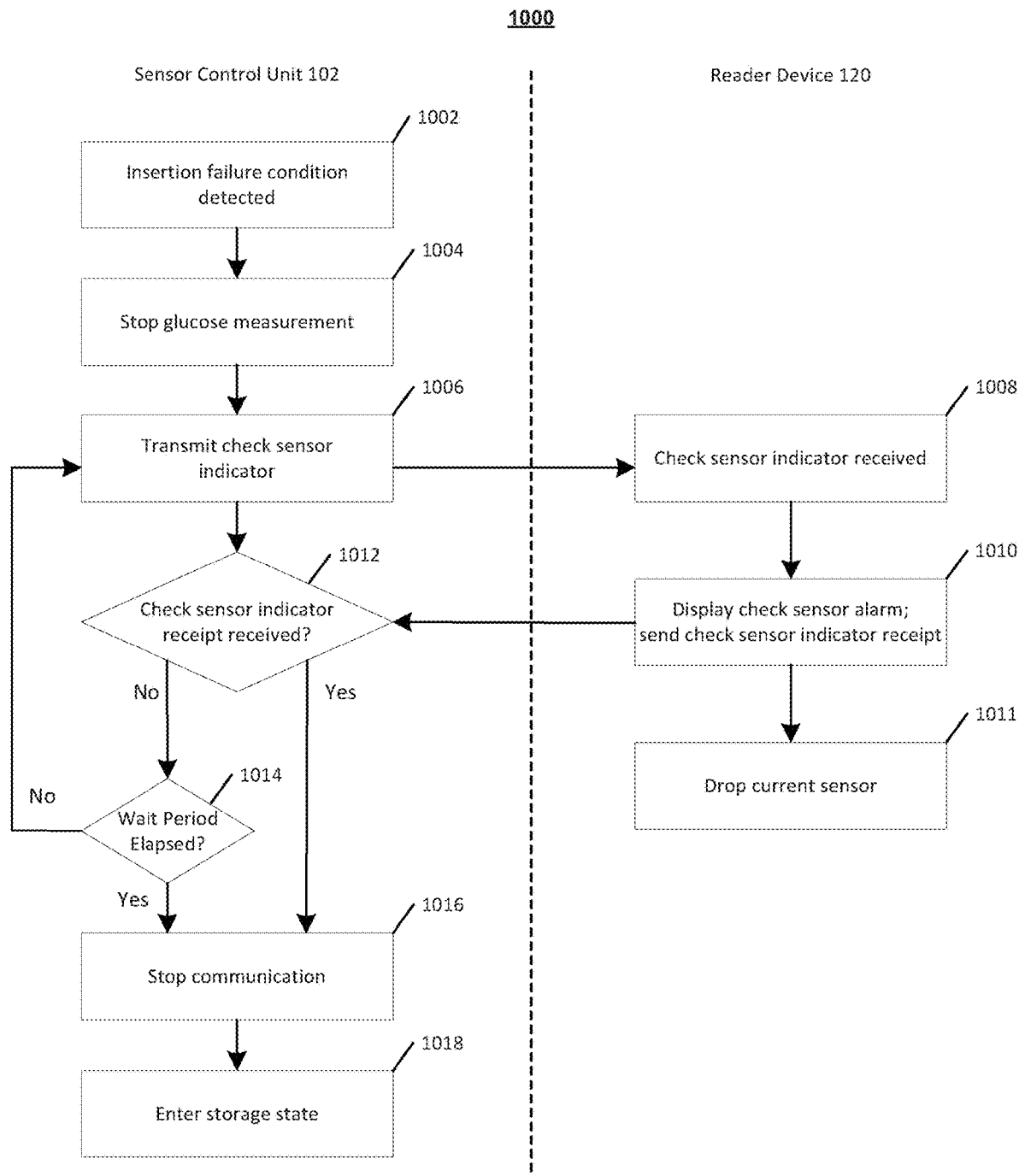
FIG. 10A is a flow diagram depicting an example embodiment of a method for generating a sensor insertion failure system alarm.

FIG. 10A is a flow diagram depicting an example embodiment of a method 1000 for generating a sensor insertion failure system alarm (also referred to as a "check sensor" system alarm). At Step 1002, a sensor insertion failure condition is detected by sensor control device 102. In some embodiments, for example, a sensor insertion failure condition can be detected when an average glucose value during a predetermined time period (e.g., average glucose value over five minutes, eight minutes, 15 minutes, etc.) is below an insertion failure glucose level threshold. At Step 1004, in response to the detection of the insertion failure condition, sensor control device 102 stops taking glucose measurements. At Step 1006, sensor control device 102 generates a check sensor indicator and transmits it via wireless communication circuitry to reader device 120. Subsequently, as shown at Steps 1012 and 1014, sensor control device 102 will continue to transmit the check sensor indicator until either: (1) a receipt of the indicator is received from reader device 120 (step 1012); or (2) a predetermined waiting period has elapsed (Step 1014), whichever occurs first.

Figure 10D:
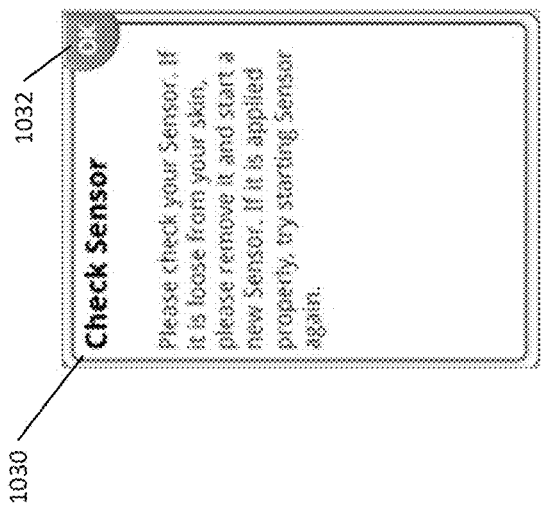
FIGS. 10B to 10D are example embodiments of GUIs to be displayed according to an example embodiment of a method for generating a sensor insertion failure system alarm.
Figure 10C:
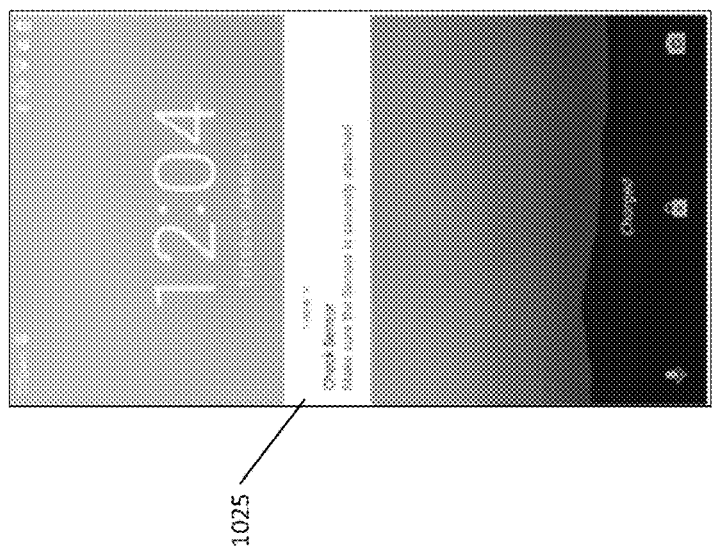
Figure 10B:
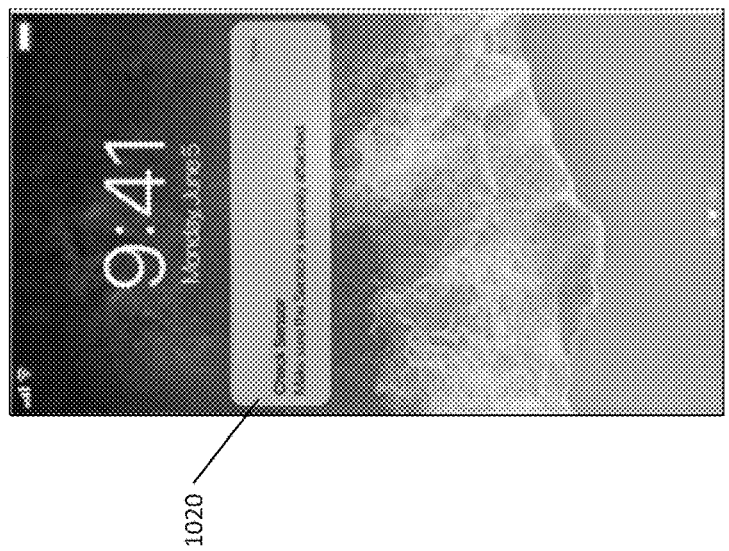

According to another aspect of the embodiments, if a wireless communication link is established between sensor control device 102 and reader device 120, then reader device 120 will receive the check sensor indicator at Step 1008. In response to receiving the check sensor indicator, reader device 120 will display a check sensor system alarm at Step 1010. FIGS. 10B to 10D are example embodiments of check sensor system alarm interfaces, as displayed on reader device 120. In some embodiments, for example, the check sensor system alarm can be a notification box, banner, or pop-up window that is output to a display of a smart phone, such as interfaces 1020 and 1025 of FIGS. 10B and 10C. In some embodiments, the check sensor alarm can be output to a display on a reader device 120, such as a glucose meter or a receiver device, such as interface 1030 of FIG. 10D. According to the embodiments, reader device 120 can also transmit a check sensor indicator receipt back to sensor control device 102. In some embodiments, for example, the check sensor indicator receipt can be automatically generated and sent upon successful display of the check sensor system alarm 1020, 1025, or 1030. In other embodiments, the check sensor indicator receipt is generated and/or transmitted in response to a predetermined user input (e.g., dismissing the check sensor system alarm, pressing a confirmation 'OK' button 1032, etc.).

Subsequently, at Step 1011, reader device 120 drops sensor control device 102. In accordance with the disclosed subject matter, Step 1011 can comprise one or more of: terminating an existing wireless communication link with sensor control device 102; unpairing from sensor control device 102; revoking an authorization or digital certificate associated with sensor control device 102; creating or modifying a record stored on reader device 120 to indicate that sensor control device 102 is in a storage state; or transmitting an update to trusted computer system 180 to indicate that sensor control device 102 is in a storage state.

Referring back to FIG. 10A, if either the check sensor indicator receipt is received (at Step 1012) by sensor control device 102 or the predetermined wait period has elapsed (Step 1014), then at Step 1016, sensor control device 102 stops the transmission of check sensor indicators. Subsequently, at Step 1018, sensor control device 102 enters a storage state in which sensor control device 102 does not take glucose measurements and the wireless communication circuitry is either de-activated or transitioned into a dormant mode. According to one aspect, while in a 'storage state,' sensor control device 102 can be re-activated by reader device 120.

Although method 1000 of FIG. 10A is described with respect to glucose measurements, those of skill in the art will appreciate that sensor control device 102 can be configured to measure other analytes (e.g., lactate, ketone, etc.) as well. In addition, although method 1000 of FIG. 10A describes certain method steps performed by reader device 120 (e.g., receiving check sensor indicator, displaying a check sensor system alarm, and sending a check sensor indicator receipt), those of skill in the art will understand that any or all of these method steps can be performed by other devices in an analyte monitoring system, such as, for example, a local computer system, a wearable computing device, or a medication delivery device. It will also be understood by those of skill in the art that method 1000 of FIG. 10A can combined with any of the other methods described herein, including but not limited to method 700 of FIG. 7, relating to expired and or failed sensor transmissions.

Figure 11A:
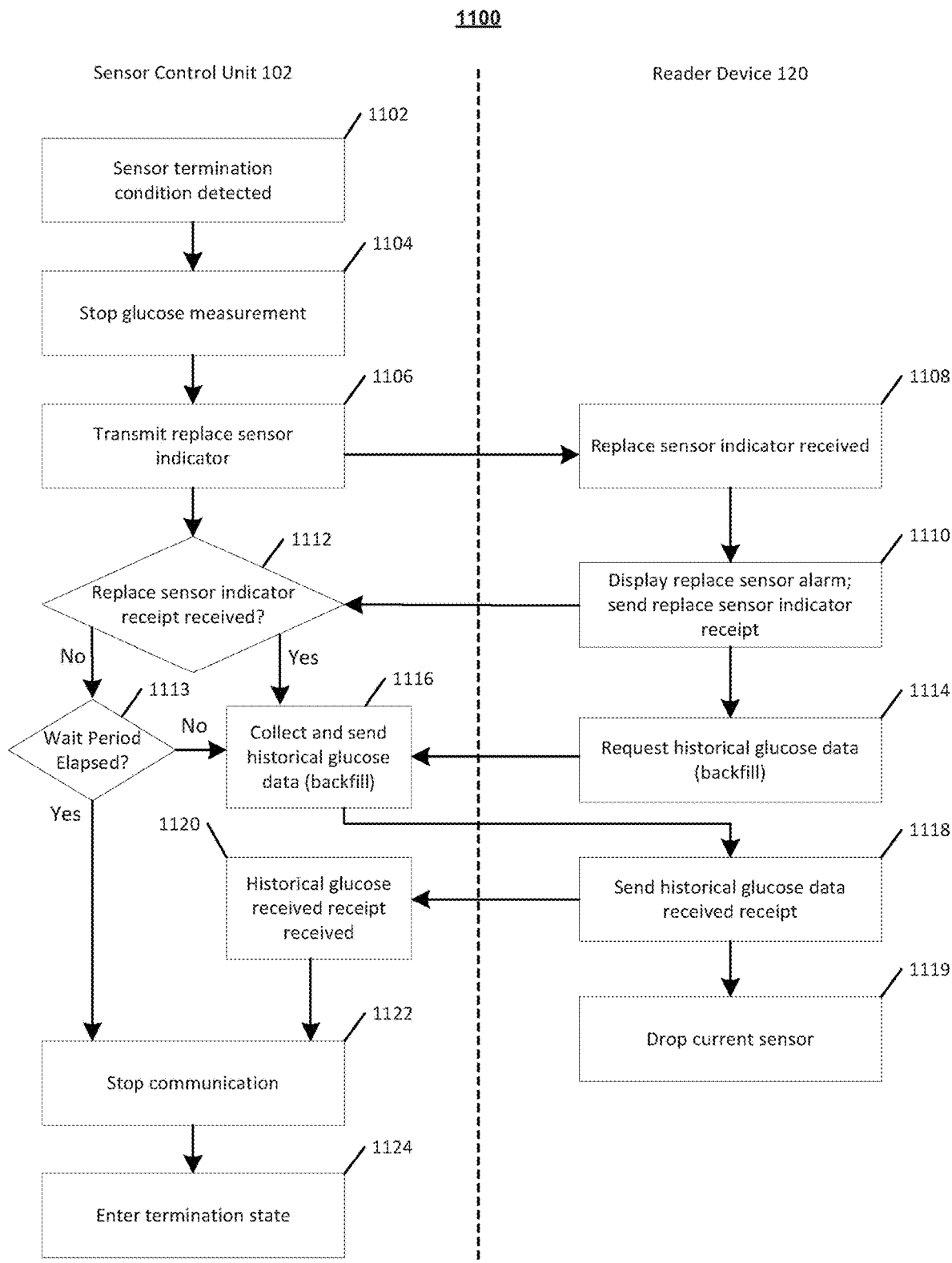
FIG. 11A is a flow diagram depicting an example embodiment of a method for generating a sensor termination system alarm.

FIG. 11A is a flow diagram depicting an example embodiment of a method 1100 for generating a sensor termination system alarm (also referred to as a "replace sensor" system alarm). At Step 1102, a sensor termination condition is detected by sensor control device 102. As described earlier, a sensor termination condition can include, but is not limited to, one or more of the following: a FIFO overflow condition detected, a sensor signal below a predetermined insertion failure threshold, moisture ingress detected, an electrode voltage exceeding a predetermined diagnostic voltage threshold, an early signal attenuation (ESA) condition, or a late signal attenuation (LSA) condition, to name a few.

At Step 1104, in response to the detection of a sensor termination condition, sensor control device 102 stops taking glucose measurements. At Step 1106, sensor control device 102 generates a replace sensor indicator and transmits it via wireless communication circuitry to reader device 120. Subsequently, at Step 1112, sensor control device 102 will continue to transmit the replace sensor indicator while determining whether a replace sensor indicator receipt has been received from reader device 102. In accordance with the disclosed subject matter, sensor control device 102 can continue to transmit the replace sensor indicator until either: (1) a predetermined waiting period has elapsed (Step 1113), or (2) a receipt of the replace sensor indicator is received (Step 1112) and sensor control device 102 has successfully transmitted backfill data (Steps 1116, 1120) to reader device 120.

Figure 11D:
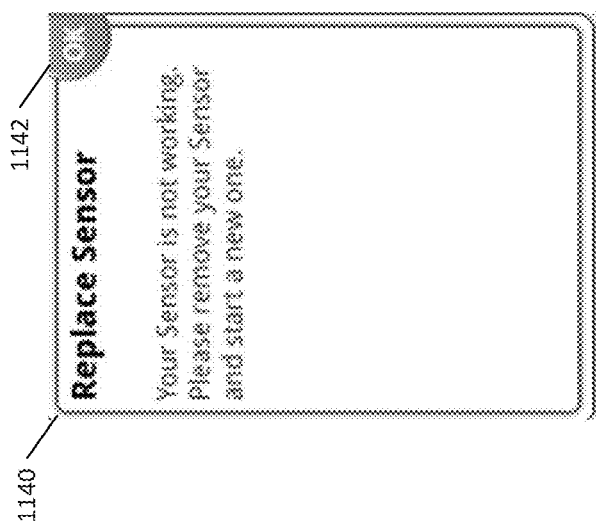
FIGS. 11B to 11D are example embodiments of GUIs to be displayed according to an example embodiment of a method for generating a sensor termination system alarm.
Figure 11C:
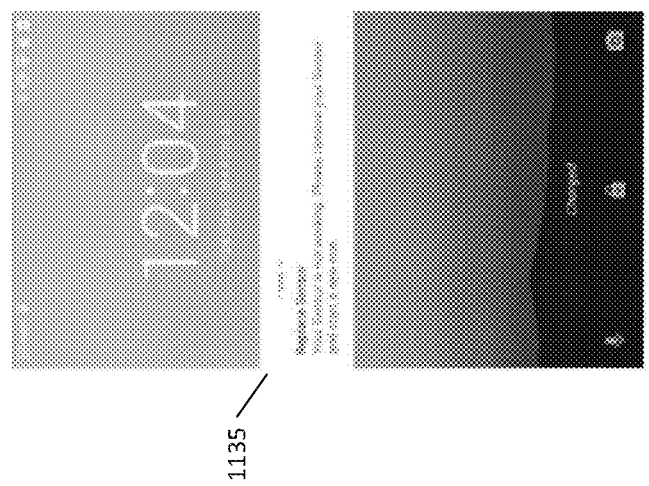
Figure 11B:
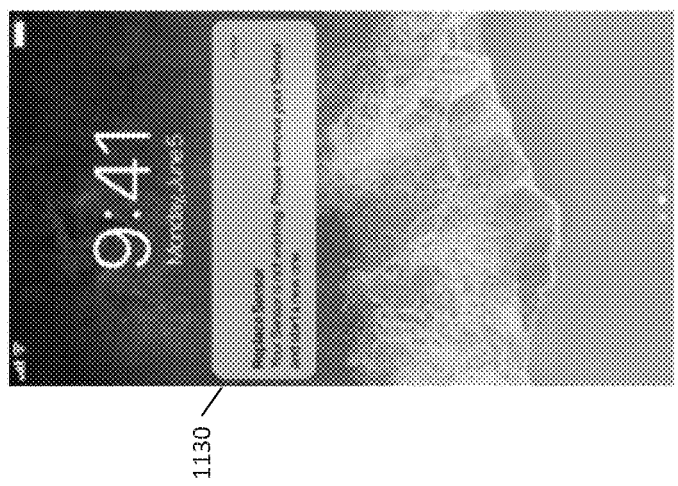

Referring still to FIG. 11A, if a wireless communication link is established between sensor control device 102 and reader device 120, then reader device 120 will receive the replace sensor indicator at Step 1108. In response to receiving the replace sensor indicator, reader device 120 will display a replace sensor system alarm at Step 1110. FIGS. 11B to 11D are example embodiments of replace sensor system alarm interfaces, as displayed on reader device 120. In some embodiments, for example, the replace sensor system alarm can be a notification box, banner, or pop-up window that is output to a display of a smart phone, such as interfaces 1130 and 1135 of FIGS. 11B and 11C. In some embodiments, the check sensor alarm can be output to a display on a reader device 120, such as a glucose meter or a receiver device, such as interface 1140 of FIG. 11D. According to the embodiments, to acknowledge receipt of the indicator, reader device 120 can also transmit a replace sensor indicator receipt back to sensor control device 102. In some embodiments, for example, the replace sensor indicator receipt can be automatically generated and sent upon successful display of the replace sensor system alarm 1130, 1135, or 1140. In other embodiments, the replace sensor indicator is generated and/or transmitted in response to a predetermined user input (e.g., dismissing the check sensor system alarm, pressing a confirmation 'OK' button 1142, etc.).

At Step 1114, after displaying the replace sensor system alarm and transmitting the replace sensor indicator receipt, reader device 120 can then request historical glucose data from sensor control device 102. At Step 1116, sensor control device 102 can collect and send to reader device 120 the requested historical glucose data. In accordance with the disclosed subject matter, the step of requesting, collecting, and communicating historical glucose data can comprise a data backfilling routine, such as the methods described with respect to FIGS. 6A and 6B.

Referring again to FIG. 11A, in response to receiving the requested historical glucose data, reader device 120 can send a historical glucose data received receipt to sensor control device 102 at Step 1118. Subsequently, at Step 1119, reader device 120 drops sensor control device 102. In accordance with the disclosed subject matter, for example, Step 1119 can comprise one or more of: terminating an existing wireless communication link with sensor control device 102; unpairing from sensor control device 102; revoking an authorization or digital certificate associated with sensor control device 102; creating or modifying a record stored on reader device 120 to indicate that sensor control device 102 has been terminated; or transmitting an update to trusted computer system 180 to indicate that sensor control device 102 has been terminated.

At Step 1120, sensor control device 102 receives the historical glucose data received receipt. Subsequently, at Step 1122, sensor control device 102 stops the transmission of the replace sensor indicator and, at Step 1124, sensor control device 102 can enter into a termination state in which sensor control device 102 does not take glucose measurements and the wireless communication circuitry is either de-activated or in a dormant mode. In accordance with the disclosed subject matter, when in a termination state, sensor control device 102 cannot be re-activated by reader device 120.

Although method 1100 of FIG. 11A is described with respect to glucose measurements, those of skill in the art will appreciate that sensor control device 102 can be configured to measure other analytes (e.g., lactate, ketone, etc.) as well. In addition, although method 1100 of FIG. 11A describes certain method steps performed by reader device 120 (e.g., receiving replace sensor indicator, displaying a replace sensor system alarm, and sending a replace sensor indicator receipt), those of skill in the art will understand that any or all of these method steps can be performed by other devices in an analyte monitoring system, such as, for example, a local computer system, a wearable computing device, or a medication delivery device. It will also be understood by those of skill in the art that method 1100 of FIG. 11A can combined with any of the other methods described herein, including but not limited to method 700 of FIG. 7, relating to expired and or failed sensor transmissions.

Example Embodiments of Improved Clinical Outcomes Based on User Engagement

Described herein are example embodiments of improved clinical outcomes based on analyte monitoring systems as described herein. In accordance with disclosed subject matter, a continuous glucose monitor regimen can include standard approved use of an analyte monitoring system. For example, and not limitation, continuous glucose monitor can be available by prescription and a regimen can be prescribed by a health care professional or as otherwise approved by a regulatory authority. In an exemplary embodiment, a regimen can include using a reader device (e.g., smart phone, dedicated reader, etc.) to scan a sensor control device, such as, for example, in a Flash Analyte Monitoring system. In an exemplary embodiment, a regimen can include rendering or brining into the foreground a sensor results interface as described herein.

In diabetes treatment, strict glycemic control from the beginning of the can have an effect on preventing the development of microvascular complications as well as on the development and progression of long-term macrovascular complications.

Therefore, being aware of glycemic variability in everyday life facilitates high-quality self-management and helps the patient aim toward stricter glycemic control. Self-monitoring of blood glucose (SMBG) by finger-stick measurement is the most common monitoring method, and the Japanese Clinical Practice Guideline for Diabetes 2019 states that SMBG is effective in glycemic control in patients with type 1 diabetes and insulin-treated patients with type 2 diabetes and recommends it as Grade A. Although the recommended timing and frequency of SMBG depend on the disease type and treatment goals, the American Diabetes Association (ADA) requires testing 6-10 times daily, although individual needs can vary, for patients using intensive insulin regimens. Further, with SMBG it can be difficult to detect nocturnal/early morning hypoglycemia or hyperglycemia immediately after meals and impossible to monitor glucose fluctuations.

Continuous glucose monitoring (CGM), as disclosed in embodiments of the disclosed subject matter, which periodically displays data (e.g., every 1-5 minutes), have been shown to significantly reduce HbA1c levels compared with SMBG in a systematic review and meta-analysis. According to embodiments disclosed herein, the CGM can be a CGM with 10, 14, 21, or 30 day wear. In some embodiments, the CGM can be a 14-day in-vivo CGM, for example, not limitation, a CGM using a redox mediator and flux limiting membrane as described in U.S. Pat. Nos. 6,605,200, 6,932,894, 8,280,474. This is one way to describe Libre without mentioning it by name.

According to a report by Bailey et al., *The Performance and Usability of a Factory-Calibrated Flash Glucose Monitoring System*, Diabetes Tech. Ther., 2015, 17(11): p. 787-794, which is herein incorporated by reference in its entirety, the mean absolute relative difference (MARD) can be 11.4% for flash glucose monitoring sensor glucose levels against capillary blood glucose reference values, with accuracy remaining stable over 14 days of wear and unaffected by patient characteristics such as body mass index (BMI), age, clinical site, insulin administration, or HbA1c. Other studies comparing flash glucose monitoring with different methods (arterial blood glucose, venous Yellow Springs Instrument (YSI) reference, laboratory random blood sugar) reported MARD within the range of 9.56-15.4%, and this accuracy was considered clinically acceptable.

In one exemplary embodiment, thirteen clinical studies investigating the efficacy of flash glucose monitoring and discussed in this exemplary embodiment are summarized in FIGS. 13A and 13B. Each of these clinical studies is herein incorporated by reference in its entirety.

SHIFT, by Ogawa et al., *Effect of the FreeStyle Libre™ Flash Glucose Monitoring System on Glycemic Control in Subjects with Type 2 Diabetes Treated with Basal-Bolus Insulin Therapy: An Open Label, Prospective, Multicenter Trial in Japan*, J. Diabetes Investigation, 2021, 12(1): p. 82-90, which is herein incorporated by reference in its entirety, was a multicenter, single-arm, prospective study to evaluate the effect of flash glucose monitoring on glycemic control in 94 Japanese patients with type 2 diabetes treated with basal-bolus insulin therapy, in which a 2-week baseline phase was followed by an 11-week flash glucose monitoring intervention. One endpoint was the change from baseline of time in hypoglycemia at 2.5 months. Other studies in Japanese patients include a randomized controlled trial (RCT) by Wada et al., *Flash glucose monitoring helps achieve better glycemic control than conventional self-monitoring of blood glucose in non-insulin-treated type 2 diabetes: a randomized controlled trial*, BMJ Open Diabetes Res. Care, 2020, 8(1), which is herein incorporated by reference in its entirety, that compared the effects of flash glucose monitoring and SMBG on glycemic control in 100 patients with non-insulin-treated type 2 diabetes and an observational study by Ida et al. that evaluated the effects of flash glucose monitoring on dietary variety, physical activity, and self-care behavior in 90 patients with type 1 and type 2 diabetes.

IMPACT, a study by Bolinder et al., *Novel glucose-sensing technology and hypoglycaemia in type 1 diabetes: a multicentre, non-masked, randomised controlled trial*, Lancet, 2016, 388(10057): p. 2254-63, which is herein incorporated by reference in its entirety, was a non-masked RCT in patients with type 1 diabetes, in which 239 type 1 diabetes patients with HbA1c≤7.5% from 23 European centers were enrolled and randomly assigned to the flash glucose monitoring group and the SMBG group in a 1:1 ratio. With an outcome of change in time in hypoglycemia from baseline to 6 months, the trial compared the effectiveness of flash glucose monitoring for glycemic control with that of SMBG.

In the REPLACE, by Haak et al, *Use of Flash Glucose-Sensing Technology for 12 months as a Replacement for Blood Glucose Monitoring in Insulin-treated Type 2 Diabetes*, Diabeter Therapy, 2017, 8(3): p. 573-586, which is herein incorporated by reference in its entirety, study, an open-label RCT in patients with type 2 diabetes, 224 type 2 diabetes patients with HbA1c between 7.5 and 12.0% from 26 European centers were enrolled and randomly assigned to the flash glucose monitoring group and the SMBG group in a 2:1 ratio. One outcome was change in HbA1c from baseline to 6 months. Then, 139 flash glucose monitoring patients who completed the 6-month treatment phase of this study continued into an additional 6-month prospective observational study (open-access phase). In both RCTs, participants had a review of their glycemic control during their visits.

Kröger et al., *Three European Retrospective Real-World Chart Review Studies to Determine the Effectiveness of Flash Glucose Monitoring on HbA1c in Adults with Type* 2, Diabetes Therapy, 2020, 11: p. 279-291, which is herein incorporated by reference in its entirety, reported a retrospective chart review of patients with type 2 diabetes using flash glucose monitoring in 18 centers in France, Austria, and Germany. The 363 patients included in the review had switched from SMBG to flash glucose monitoring at least 3 months before the start of the study and had a baseline HbA1c (measurement within 3 months prior to starting flash glucose monitoring use) between 8.0 and 12.0%. One outcome was change in HbA1c from baseline at 3-6 months after starting flash glucose monitoring use.

An open-label RCT reported by Yaron et al., *Effect of Flash Glucose Monitoring Technology on Glycemic Control and Treatment Satisfaction in Patients With Type* 2 *Diabetes*, Diabetes Care, 2019, 42(7), which is herein incorporated by reference in its entirety, was conducted in 101 patients with type 2 diabetes (baseline HbA1c 7.5-10.0%) from 2 centers in Israel. Patients were randomly assigned to the flash glucose monitoring group and the SMBG group in a 1:1 ratio and treated for 10 weeks. Patients in the flash glucose monitoring group were instructed to perform a scan at least every 8 hours, and all patients were frequently instructed to adjust their insulin doses. One outcome was satisfaction with treatment; other measures including quality of life (QOL), HbA1c, comfort using flash glucose monitoring, and frequency of hypoglycemic events were also evaluated.

Evans et al., *The Impact of Flash Glucose Monitoring on Glycaemic Control as Measured by HbA1c: A Meta-analysis of Clinical Trials and Real-World Observational Studies*, Diabetes Therapy, 2020, 11(1): p. 83-95, which is herein incorporated by reference in its entirety, reported a meta-analysis of 25 studies (n=1,723) that reported change in HbA1c in adult and pediatric patients with type 1 or type 2 diabetes using flash glucose monitoring. A meta-analysis was performed using a random effects model on the 21 studies where HbA1c levels at baseline and 2-4 months after starting flash glucose monitoring use were available, and random effects meta-regression of change in HbA1c was performed versus baseline HbA1c. In addition, a longitudinal analysis was performed in 1,276 adult patients with type 1 and type 2 diabetes whose HbA1c was continuously measured 1-12 months after starting flash glucose monitoring use.

FLARE-NL4, by Fokkert et al, *Improved well-being and decreased disease burden after* 1*-year use of flash glucose monitoring (FLARE-NL4)*, BMJ Open Diabetes Research & Care, 2020, 7(1), which is herein incorporated by reference in its entirety, was a 1-year prospective registry study that included 1,277 patients with type 1 and type 2 diabetes using flash glucose monitoring in the Netherlands. One endpoint was change in HbA1c; other endpoints evaluated included frequency and severity of hypoglycemia, health-related QOL, and disease burden including hospital admission and work absenteeism.

Dunn et al., *Real-world flash glucose monitoring patterns and associations between self-monitoring frequency and glycaemic measures: A European analysis of over 60 million glucose tests*, Diabetes Res. & Clinical Practice, 2017, 137: p. 37-46, which is herein incorporated by reference in its entirety, analyzed real-world data of flash glucose monitoring use from 50,831 readers in Europe stored in a cloud database between September 2014 and May 2016. Patients were grouped by scan frequency, and the relationship between scan frequency and estimated HbA1c (eA1c) was evaluated. Other studies that used real-world data include a report investigating the relationship between scan frequency and CGM measures in clinical practice in Spain, and a report investigating the use of flash glucose monitoring in Brazil.

The HbA1c test can be used for the diagnosis and management of diabetes. Although HbA1c does not detect glucose variability or hypoglycemic events, it is known to reflect the average blood glucose levels over the previous 2 to 3 months, and equations have been described to calculate the estimated average glucose levels from the HbA1c levels or the eA1c from the average glucose levels. In addition, HbA1c correlates with the risk of long-term diabetes complications and is considered a reliable biomarker for diagnosing and evaluating the long-term prognosis of diabetes.

IMPACT and REPLACE did not show a significant difference in the mean change in HbA1c from baseline between the flash glucose monitoring group and the SMBG group at 6 months after the start of the study (IMPACT, difference in mean HbA1c between the 2 groups at 6 months after the start of the study: 0.00, p=0.9556; REPLACE, change in HbA1c at 6 months after the start of the study, SMBG group: −0.31, flash glucose monitoring group: −0.29, p=0.8222).

Figure 13C:
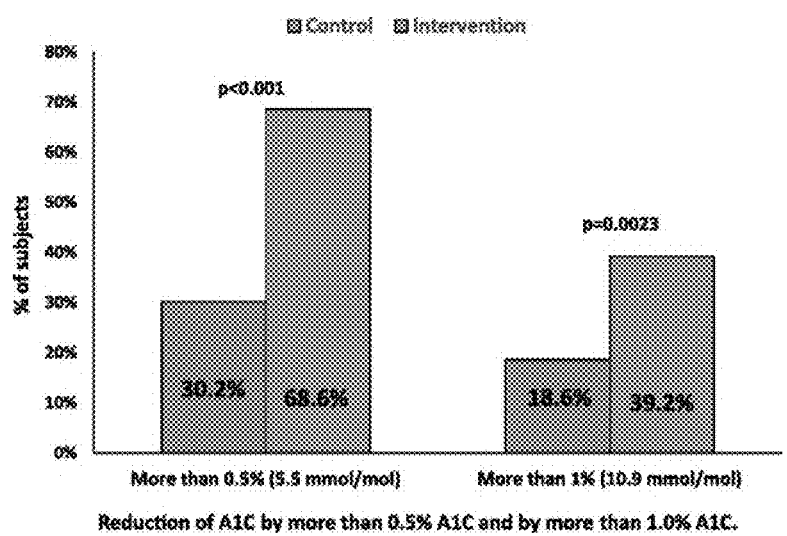

In FIG. 13C, as observed by Yaron et al.'s RCT, the mean change (standard deviation [SD]) in HbA1c from baseline at 10 weeks after the start of the study was significantly lower at −0.82 (0.84) % in the flash glucose monitoring group compared with −0.33 (0.78) % in the SMBG group (p=0.005). In a non-prespecified post hoc analysis, the proportion of patients whose HbA1c was reduced by ≥0.5% was 68.6% in the flash glucose monitoring group compared with 30.2% in the SMBG group, showing a significant difference (p<0.001); a significant difference was similarly seen in the proportion of patients whose HbA1c was reduced by ≥1% (SMBG group: 18.6%, flash glucose monitoring group: 39.2%, p=0.0023).

As illustrated in FIG. 13D, in Kröger et al.'s chart review, HbA1c levels significantly decreased from baseline with the mean (standard error) change of −0.9 (0.05) % in patients with type 2 diabetes who used flash glucose monitoring continuously for 3-6 months (p<0.0001), and this pattern was consistent across the 3 countries in the study.

Figure 13E:
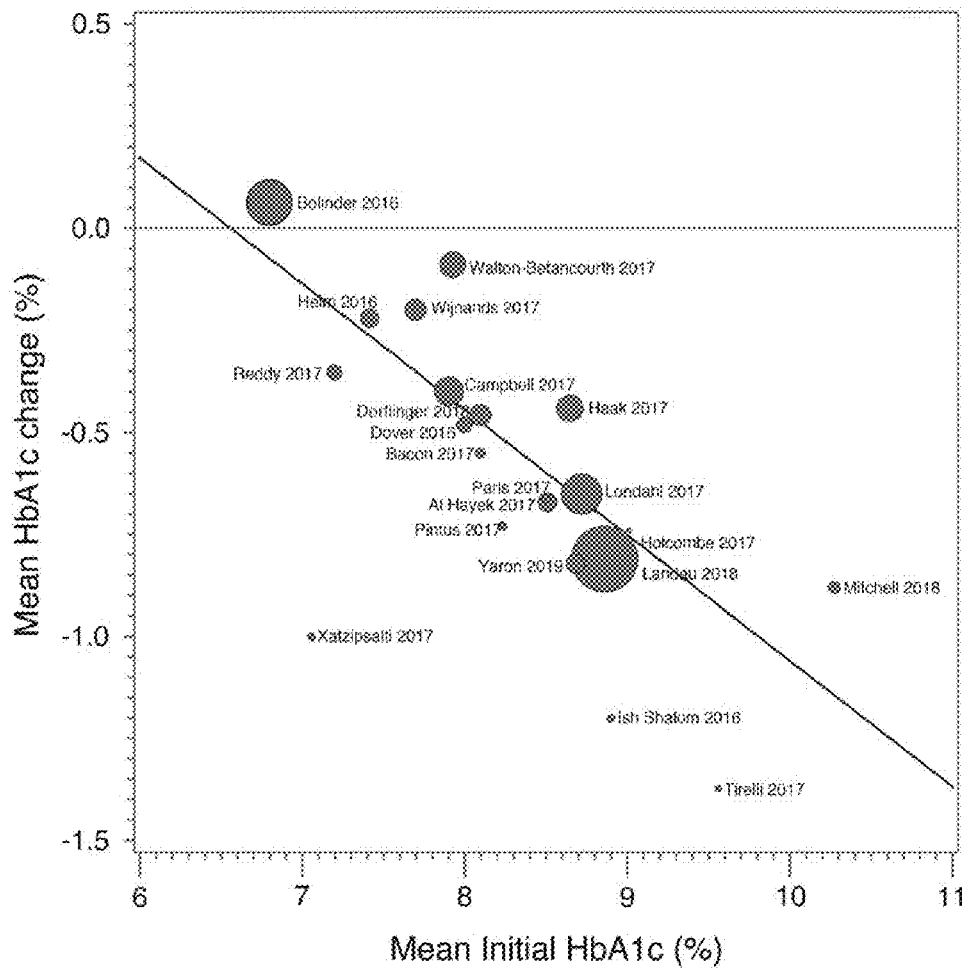

As illustrated in FIG. 13E, Evans et al.'s meta-regression analysis demonstrated that the higher the baseline HbA1c, the greater the reduction in HbA1c after treatment using flash glucose monitoring. A longitudinal analysis in 1,276 adults showed that HbA1c fell markedly within 2 months of starting flash glucose monitor use and the changes were sustained up to 12 months. Although mostly studied in type 1 diabetes patients, flash glucose monitoring is shown to improve and maintain HbA1c in many studies.

In the SHIFT study conducted in Japanese patients, a significant improvement was observed in eA1c at the end of the study (11 weeks) when compared with baseline (−0.39±0.81%, p<0.0001). According to Ida et al.'s report, no significant changes in HbA1c were observed at the end of the study (12 weeks) when compared with baseline in patients with type 1 diabetes (7.7±1.2 vs. 7.7±1.3, p=0.921), but a significant improvement was observed in patients with type 2 diabetes (7.4±0.8 vs. 7.7±1.2, p=0.025). 20). Wada et al. reported that HbA1c was significantly improved compared with baseline in both the flash glucose monitoring group (−0.43%, p<0.001) and the SMBG group (−0.30%, p=0.001).

Beyond a change a HbA1c, certain studies analyzed according to this embodiment also indicate time in hypoglycemia for the subjects studied. Hypoglycemia is an emergency that occurs during diabetes treatment, and it has been suggested that severe hypoglycemia or hypoglycemia unawareness may become risk factors for macroangiopathy and dementia. Flash glucose monitoring incorporates an ambulatory glucose profile (AGP), and patients can graphically see the trends in their glucose level over a day. In addition, sensor glucose levels <70 mg/dL persisting for >15 minutes are recorded as hypoglycemic events.

Figure 13F:
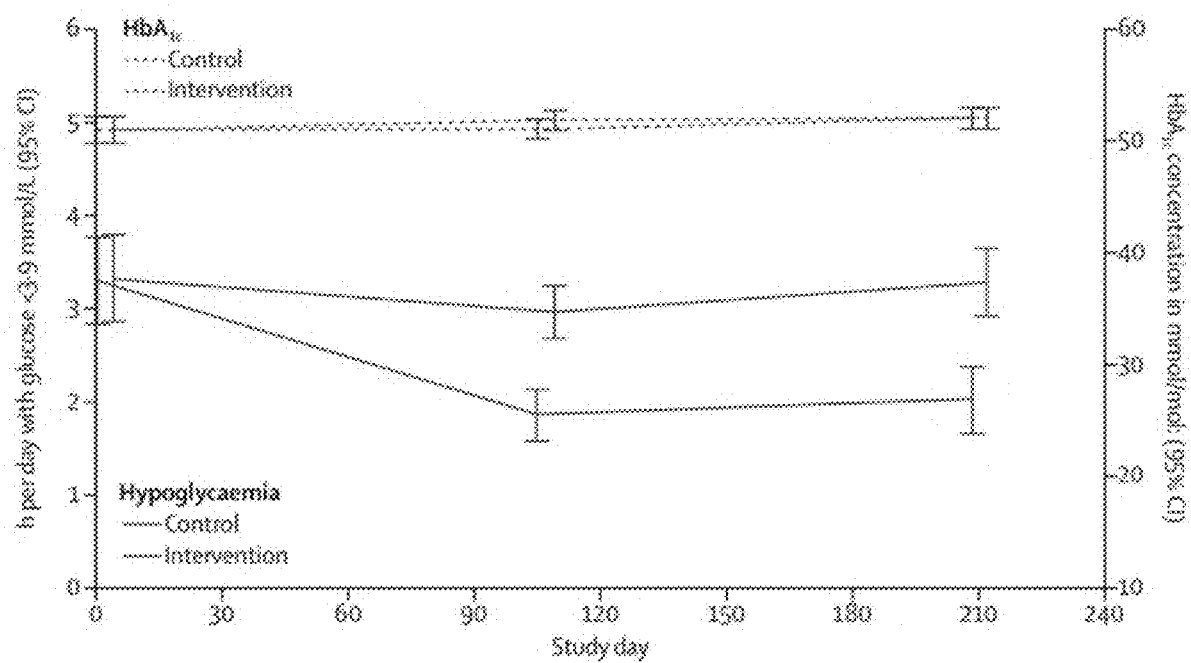

As illustrated in FIG. 13F, in the IMPACT study, conducted in patients with type 1 diabetes, one outcome of mean time in hypoglycemia (<70 mg/dL) at 6 months was 2.03 h/day (−1.39 h/day from baseline) in the flash glucose monitoring group, which was 38% lower than 3.27 h/day (−0.14 h/day from baseline) in the SMBG group (p<0.0001).

In the REPLACE study conducted in patients with type 2 diabetes, although there was no difference in the outcome of change in HbA1c from baseline at 6 months between the flash glucose monitoring group and the SMBG group, mean time in hypoglycemia (<70 mg/dL) at 6 months was reduced by 43% in the flash glucose monitoring group compared with the SMBG group (p=0.0006). During the open-access extension phase of REPLACE, mean time in hypoglycemia at 12 months was reduced by 50% compared with baseline for the flash glucose monitoring group (p=0.0002).

In SHIFT, time in hypoglycemia at the end of the study (11 weeks) was not significantly different compared with baseline (p=0.6354), but eA1c was significantly decreased (p<0.0001). Overall, it was suggested that the use of flash glucose monitoring may improve eA1c without increasing time in hypoglycemia and may improve time in range (TIR) and reduce time above range (TAR).

In IMPACT and REPLACE, with target sensor glucose levels of 70-180 mg/dL, TIR at 6 months was compared between the flash glucose monitoring group and the SMBG group. As a result, the IMPACT study in patients with type 1 diabetes showed a significant increase in TIR compared with the SMBG group, but the REPLACE study in patients with type 2 diabetes did not show a difference in TIR between the groups (p=0.7925). 21), 22) In the SHIFT study, with a treatment target range of 70-180 mg/dL, TIR at 11 weeks was 16.7±3.7 h/day (mean±SD), showing a significant improvement from baseline (15.0±4.0 h/day) (p<0.0001).

Analyzes according to the above outlined studies show certain benefits of flash glucose monitoring within a clinical setting, specifically, results from certain RCTs such as IMPACT and REPLACE support the clinical benefits of flash glucose monitoring in glycemic control. Here, further studies are reviewed that used real-world data from Europe, Spain, and Brazil.

Figure 13G:
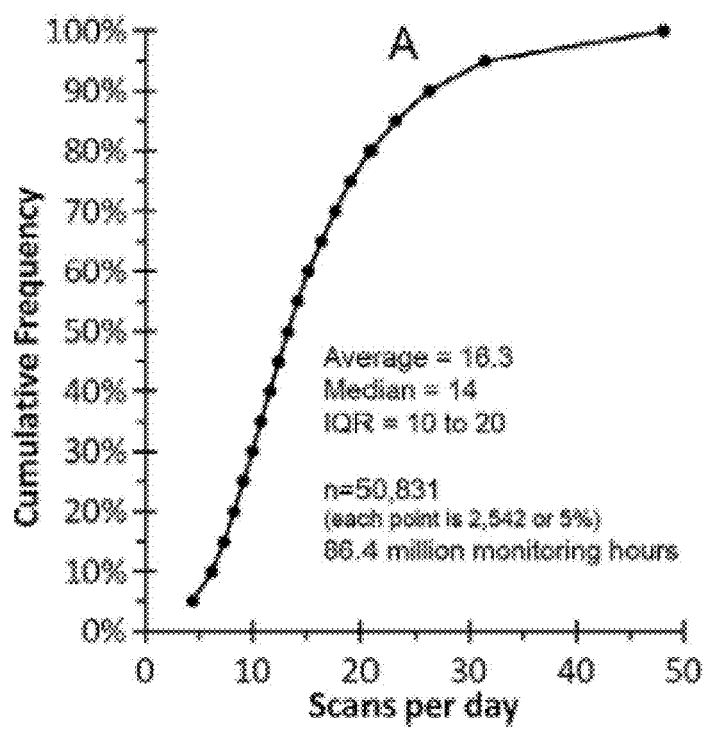

As illustrated in FIG. 13G, the use and clinical benefits of flash glucose monitoring from the real-world data of 50,831 readers in Europe, users performed a total of 86.4 million hours of readings, 345.6 million automatically stored readings, and 63.8 million scans, with a median of 14 scans (interquartile range: 10-20 scans).

Figure 13H:
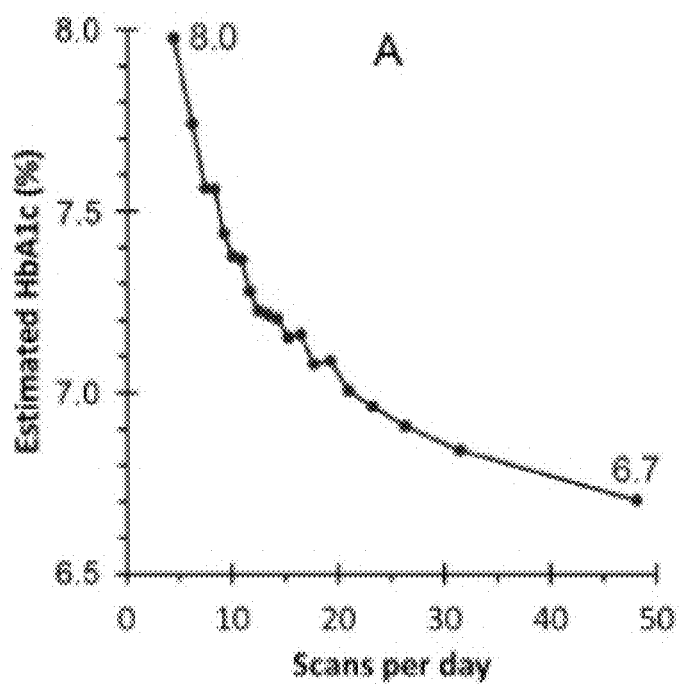

FIG. 13H illustrates an analysis wherein the readers were allocated to 20 equally sized groups by scan frequency, the lowest scan rate group (mean, 4.4 times/day) had an eA1c of 8.0%, while the highest scan rate group (mean, 48.1 times/day) had an eA1c of 6.7%, showing a reduction in eA1c with increasing number of scans. TIR (sensor glucose levels 70-180 mg/dL) significantly increased from 12.0 h/day to 16.8 h/day when comparing the lowest with the highest scan rate groups (p<0.001). Both TAR and TBR significantly decreased in the highest scan rate group compared with the lowest scan rate group (p<0.001 each). These patterns can be consistent across different countries.

Similar results were obtained from the real-world data of 22,949 readers in Spain: eA1c was significantly lower at 6.9% (95% CI: 6.9-7.0%) in the highest scan rate group (mean, 39.6 scans/day) compared with 8.0% (95% CI: 8.0-8.1%) in the lowest scan rate group (3.9 scans/day; p<0.001); and TIR (sensor glucose levels 70-180 mg/dL) significantly increased from 11.5 h/day in the lowest scan rate group to 15.6 h/day in the highest scan rate group (p<0.001). 29) A real-world data study in Brazil also showed that eA1c was significantly lower at 6.71% (95% CI: 6.63-6.80%) in the highest scan rate group (mean, 43.1 times/day) compared with 7.56% (95% CI: 7.44-7.68%) in the lowest scan rate group (mean, 3.56 times/day; p<0.01), and TIR (sensor glucose levels 70-180 mg/dL) increased in the highest rate group compared with the lowest rate group (p<0.01).

These results suggest that increased scan frequency with flash glucose monitoring may improve glycemic control conditions including HbA1c and CGM metrics.

Figure 13I:
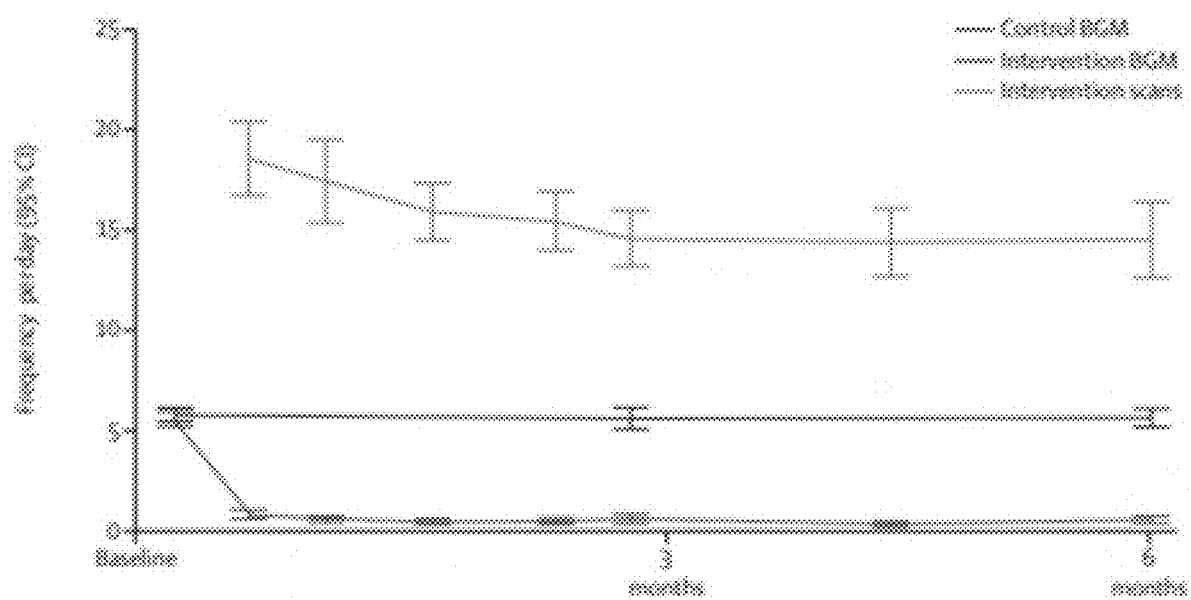
Figure 13J:
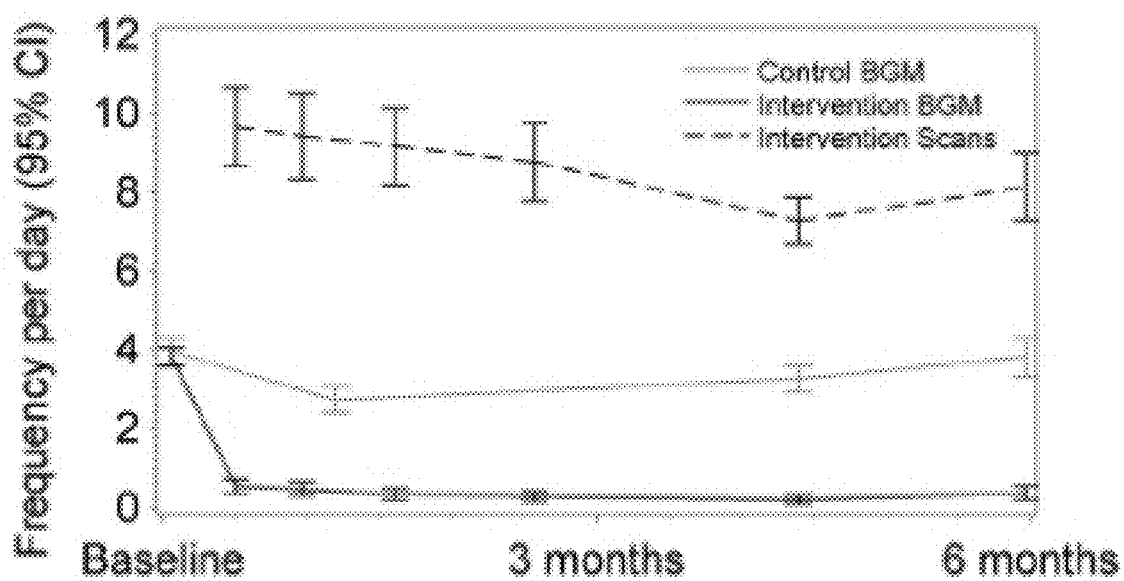
Figure 13K:
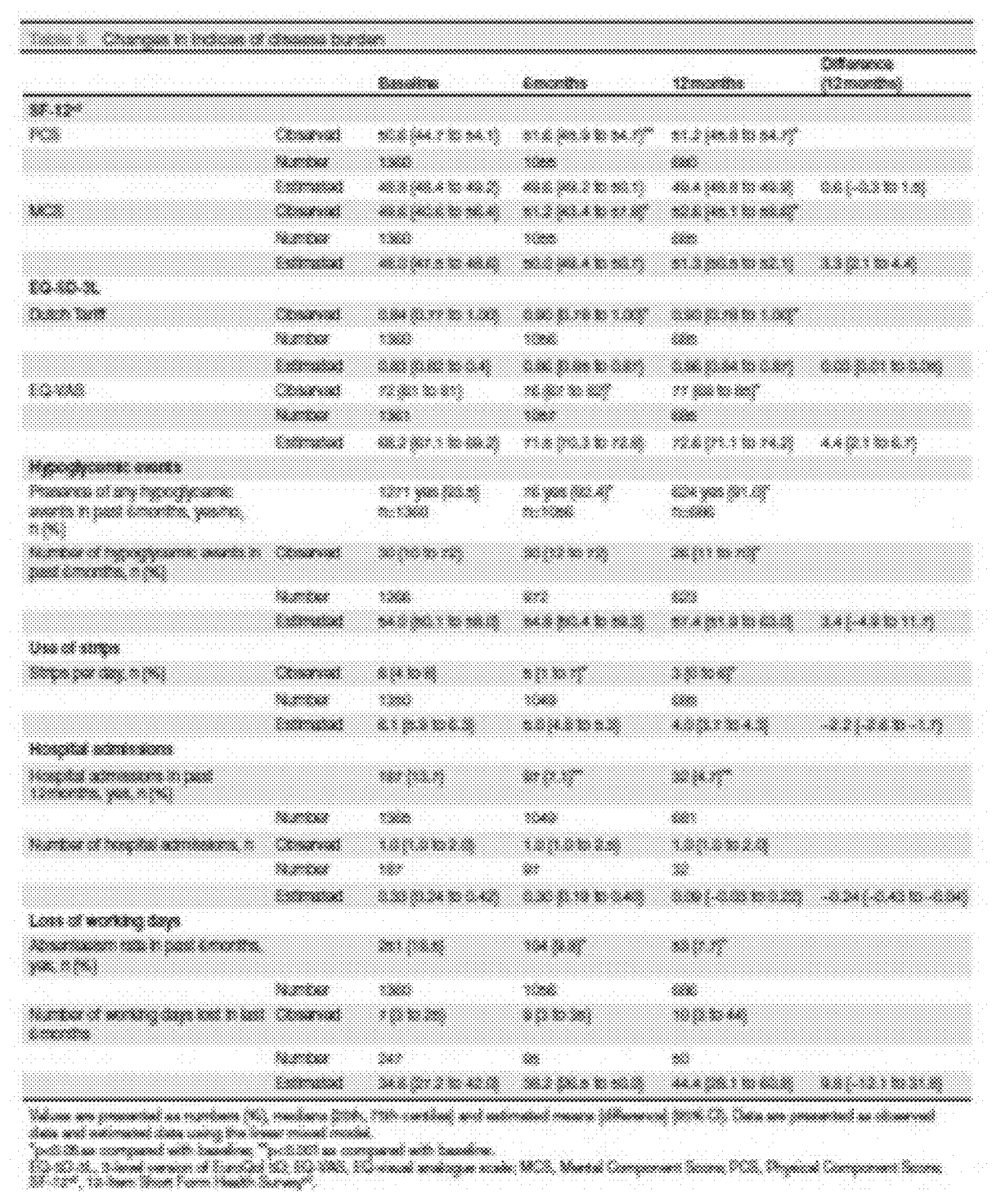

Glycemic control using flash glucose monitoring can reduce the daily burden for patients with diabetes by reducing the frequency of SMBG with finger-stick measurement. As illustrated in FIG. 13I, according to the IMPACT study, the mean (SD) number of SMBG tests performed in the flash glucose monitoring group decreased from 5.5 (2.0) tests/day at baseline to 0.5 (0.7) tests/day at 6 months. No change was seen in the SMBG group, with 5.8 (1.7) tests/day at baseline and 5.6 (2.2) tests/day at 6 months. Further, as illustrated in FIG. 13J, during the 6-month study period of REPLACE, the mean (SD) SMBG frequency for the flash glucose monitoring group also fell from 3.8 (1.4) tests/day to 0.3 (0.7) tests/day, whereas no change was seen for the SMBG group (3.9 [1.5] tests/day to 3.8 [1.9] tests/day). The average scan frequency (SD) for the flash glucose monitoring group was 15.1 (6.9) times/day in IMPACT and 8.3 (4.4) times/day in REPLACE, and the flash glucose monitoring group tended to perform more frequent monitoring than the SMBG group. REPLACE showed no significant difference in the number of scans performed by those <65 years and ≥65 years of age.

Patient reported outcome measures (PROMs), which contain both QOL and treatment satisfaction, are also a metric and the goals of diabetes treatment include maintaining the same everyday QOL as healthy people and improvements of treatment satisfaction. One of the typical measures used to assess QOL in the treatment of diabetes is the Diabetes Quality of Life (DQoL) Questionnaire, which was developed by the Diabetes Control and Complications Trial (DCCT) Research Group, can assess the impact of disease on the lifestyle and daily lives of patients with insulin-dependent diabetes mellitus.

Diabetes Treatment Satisfaction Questionnaire (DTSQ) was developed in the UK and can be used globally as a tool to quantify treatment satisfaction. It can be applied to all patients with diabetes and is useful for comparison between treatments. The DTSQ change version (DTSQc), which can be used to assess changes in satisfaction pre- and post-intervention, has also been developed.

In IMPACT and REPLACE, the DTSQ score was improved significantly in the flash glucose monitoring group compared with the SMBG group (both p<0.0001); however, there was no difference in the DQoL score between the groups in IMPACT. Yaron et al.'s RCT showed significant differences between the SMBG and flash glucose monitoring groups in the DTSQc score items flexibility of treatment and willingness to recommend treatment to someone else (p=0.019, 0.023). A 1-year registry study, FLARE-NL4, used non-diabetes-specific QOL measures; the 12-Item Short Form Health Surveyv2 (SF-12v2) mental component summary score of QOL and the 3-level version of EuroQol (EQ-5D-3L) showed significant improvement from baseline to the end of the study (95% CIs for each difference: 2.1-4.4, 0.01-0.05), whereas the SF-12v2 physical component summary score of QOL showed no significant change. The percentage of patients with diabetes-related hospital admissions in the past 12 months decreased significantly from 13.7% at baseline to 4.7% (p<0.01), and the work absenteeism rate in the past 6 months also decreased significantly from 18.5% to 7.7% (p<0.05) (Table 3). 27)

In SHIFT, scores for the DTSQ, including treatment satisfaction, significantly improved from baseline to the end of the study (p<0.0001), and participants' perception of episodes of hypoglycemia and hyperglycemia also significantly improved (p=0.0062 and p=0.0310, respectively).

Overall, although different PROMs were used, flash glucose monitoring use was shown to have favorable effects on patient QOL and treatment satisfaction.

Beyond the different objective analysis outline above, safety related to actual device use is also a factor in technique uptake and effectiveness of treatment. The most common device-related adverse events on flash glucose monitoring include sensor insertion site reactions (e.g., pain, hemorrhage, swelling, induration, bruise) and sensor-wear reactions (e.g., erythema, itching, rash). In IMPACT, 13 device-related adverse events were reported by 10 participants in the flash glucose monitoring group, including 4 events each of allergic reaction and insertion site reaction, 2 events of erythema, and 1 event each of itching, rash, and edema. In addition, 248 sensor insertion/wear-related findings or symptoms were observed in 65 participants in both groups. Seven participants discontinued the study due to device-related adverse events or repetitive occurrences of sensor insertion-related symptoms. During the 6-month treatment phase of REPLACE, 6 participants in the flash glucose monitoring group reported 9 sensor-wear reactions as device-related adverse events, all of which were resolved at the end of the study. In addition, 50 participants from both groups reported 158 symptoms associated with sensor insertion/wear or finger-stick measurement, and 63% of these symptoms were due to the sensor adhesive. These symptoms resolved without medical intervention. In SHIFT, a total of 273 adverse events were experienced by 60 of 94 participants (63.8%), including serious adverse events reported for 5 participants. Of these, 257 adverse events were related to symptomatic hypoglycemia. No episodes of diabetic ketoacidosis (DKA) or hyperosmolar hyperglycemic state (HHS) were reported.

Serious acute complications of diabetes can also occur, including DKA and HHS, but there were no reported events of DKA or HHS in IMPACT, REPLACE, or SHIFT. As discussed above, information displayed on the flash glucose monitoring reader includes the glucose level trend arrow, which indicates the direction and velocity of changing glucose levels over the previous 15 minutes; it is expected that determination of the timing and the dose of insulin based on this information will lead to prevention of acute complications.

At the American Diabetes Association's 80th Scientific Sessions held in June 2020 (ADA 2020), results were reported from a large clinical trial in patients with type 1 and type 2 diabetes on intensive insulin therapy in countries including the US, Sweden, and France, showing in particular an improvement in rates of acute diabetes events and hospitalizations.

Clinical studies of flash glucose monitoring reviewed in this embodiment investigated the efficacy of flash glucose monitoring in glycemic control of insulin-treated diabetic patients using various outcome measures including change in HbA1c, time in hypoglycemia, and PROMs. IMPACT and REPLACE showed a significant decrease in time in hypoglycemia, but did not show any significant changes in HbA1c. On the other hand, Yaron et al.'s RCT and Kröger et al.'s chart review demonstrated a significant reduction in HbA1c; the SHIFT study, which was conducted in Japanese patients, demonstrated a significant reduction in eA1c, although no significant change was observed in time in hypoglycemia.

A report from the Committee on a Survey of Severe Hypoglycemia in the Japan Diabetes Society indicates that as long as HbA1c is not extremely low, hypoglycemia is inversely correlated with HbA1c; therefore, the fact that either the decrease in time in hypoglycemia or the reduction in HbA1c was significant suggests that flash glucose monitoring has generally contributed to the stabilization of glucose control. Baseline characteristics and number of scans may affect the efficacy of flash glucose monitoring. Discussions are needed in the future on creating standard protocols in order to increase the clinical efficacy of flash glucose monitoring.

With regard to the assessment of QOL, in Yaron et al.'s RCT with an outcome measure of DTSQ, although there was no significant improvement in the overall DTSQc score, significant improvement was seen in scores for the items flexibility of treatment and willingness to recommend treatment to someone else for the flash glucose monitoring group compared with the SMBG group. Although the DTSQ score was not the primary outcome measure for IMPACT and REPLACE, it improved significantly in the flash glucose monitoring group compared with the SMBG group. These results suggest that the use of flash glucose monitoring may contribute more to the improvement of QOL in diabetes treatment than SMBG.

The presently disclosed subject matter will be better understood by reference to the following Examples. These Examples are merely illustrative of the presently disclosed subject matter and should not be considered as limiting the scope of the subject matter in any way.

According to embodiments of the disclosed subject matter, the analyte monitoring systems described herein can sense analyte levels at a predetermined frequency (e.g., every minute, every five minutes, every ten minutes, etc.). Thereafter, by "scanning" the sensor with a reader device, the user can view the analyte concentration and/or its trend over the last several minutes (e.g., without limitation, 5 minutes, 10 minutes, 15 minutes, etc.) in the form of a trend arrow and the glucose profile curve for the last 8 hours. In some embodiments, users may download, access, or view the entire memory of sensor (e.g., all 14 days if a sensor lifespan is 14 days, 15 days, etc.) by scanning. As discussed above, FIG. 2D is an example embodiment of a GUI comprising sensor results interface showing a trend arrow. As embodied herein, the total sum of a number of scans and a number of views for each day is associated with metabolic benefits and therefore confirms the importance of visualization of glucose data by the patient. In particular, number of scans performed by the patient each day is linked to improvement of three metabolic parameters: hyperglycemia, hypoglycemia and glycemic variability.

According to embodiments, a continuous glucose monitor regimen as described herein may be used to improve metabolic parameters in users. The benefits of CGM use can be better understood and further demonstrated by the examples provided below.

EXAMPLE 1

In an embodiment, sensed glucose data from 20,960 and 97,788 French patients from September 2014 to June 2017 and from September 2014 to September 2018, respectively, was analyzed from a database. In particular, 1,068,269 sensors provided 141 million scanned glucose values and 1.25 billion automatically recorded glucose values corresponding to the average interstitial glucose measurement every 15 minutes. This data corresponds to 312 million hours of follow-up, and included patients with type 1 diabetes and type 2 diabetes. Additional details of this embodiment are disclosed in *The frequency of FreeStyle Libre glucose sensor scans performed by the diabetic patient on a daily basis is associated with better parameters for monitoring his glucose profile: Analysis of 312 million hours of monitoring in real life in France*, which was originally published in Médecine des Maladies Métaboliques, Volume 14, Issue 7 in November 2020 and can be accessed at the website https://www.sciencedirect.com/science/article/pii/ S1957255720002163, and is incorporated by reference herein in its entirety.

The data from a sensor was included in the analysis only if the sensor measured and recorded the interstitial glucose for at least 120 hours, i.e. at least 480 interstitial glucose values, which corresponds to 40% of the maximum operating time (14 days) of a sensor. Further, sensor data from the same reader were combined and correspond to a reader device (or "patient").

Figure 14A:
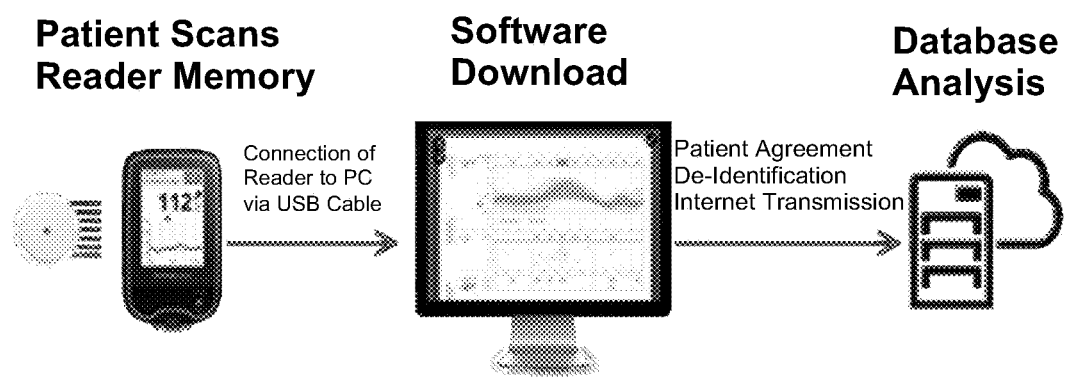
Figure 14B:
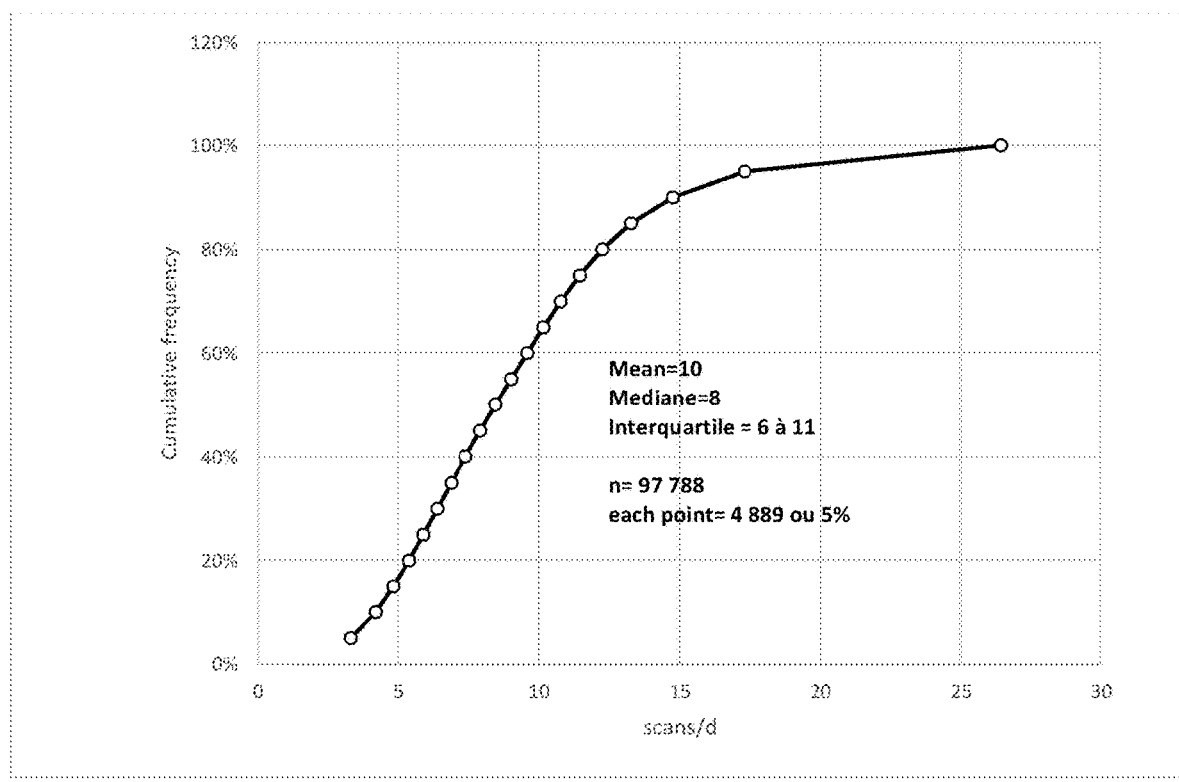

Thereafter, frequency of scans was calculated for each sensor by dividing the number of scans by the sensor's operating time evaluated from the start and expiry date of the sensor. The scan frequency per reader was calculated by averaging the scan frequency per sensor for the sensors linked to the same reader. As can be seen in FIG. 14B, the mean frequency of scans per day was 10 with a median of 8, and an interquartile range of 6 to 11.

Further, cumulative scanning frequency was calculated for every 5% of the available readers, generating 20 groups of 4,889 readers ranked in ascending order of scanning frequency. The glucose profile settings for each such class can be seen in FIG. 14I. As such, a cumulative distribution curve of scan frequency per reader (or "patient"), mean, median and interquartile range to be determined. For each group corresponding to a scan frequency class, the mean±AND of the interstitial glucose profile parameters defined above was calculated. For the analysis on the variations of the interstitial glucose profile parameters per additional scan, 10 cumulative scan frequency classes were performed by classifying each 10% of the available readers (i.e. 10 classes of 9,779 readers) according to the number of scans performed.

The different groups defined by the frequency of scans were compared by a univariate analysis of variance (ANOVA) test. The range of glucose parameters and relative variations were established for the patient groups from those scanning least to those scanning most frequently. The database was analyzed in a structured query language (SQL), described in more detail at www.knime.org and by the statistical software package R (www.r-project.org). The large sample size and multiple comparisons resulted in a $P<0.01$ as statistically significant. Confidence intervals were calculated for each scan frequency group by least-squares mean and comparisons were made between these different groups.

For each sensor user, the following interstitial glucose profile parameters were calculated: time spent in the target range of 70 to 180 mg/dl (TIR 70-180); time spent above 180 mg/dl (T>180), or above 240 mg/dl (T>240); and, time spent below 70 mg/dl (T<70), 55 mg/dl (T<55) or 45 (T<45).

Figure 14C:
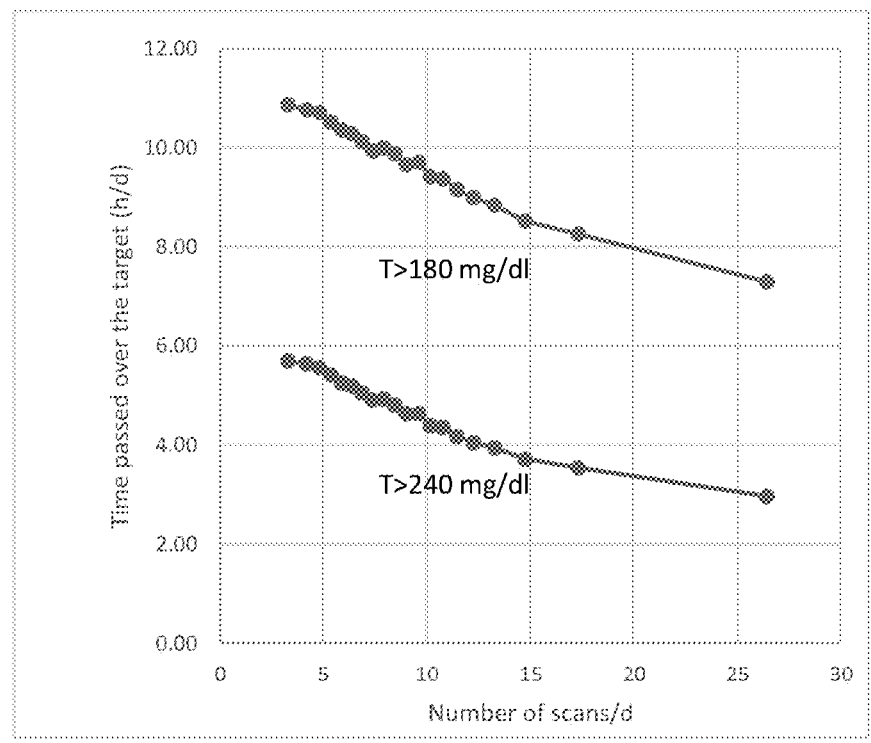
Figure 14D:
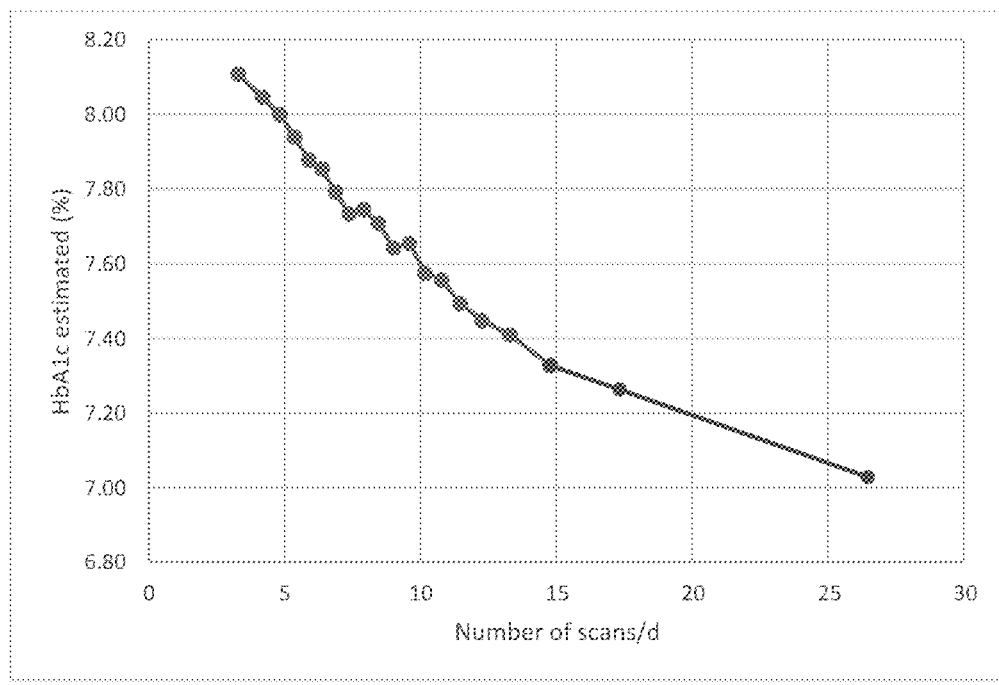
Figure 14E:
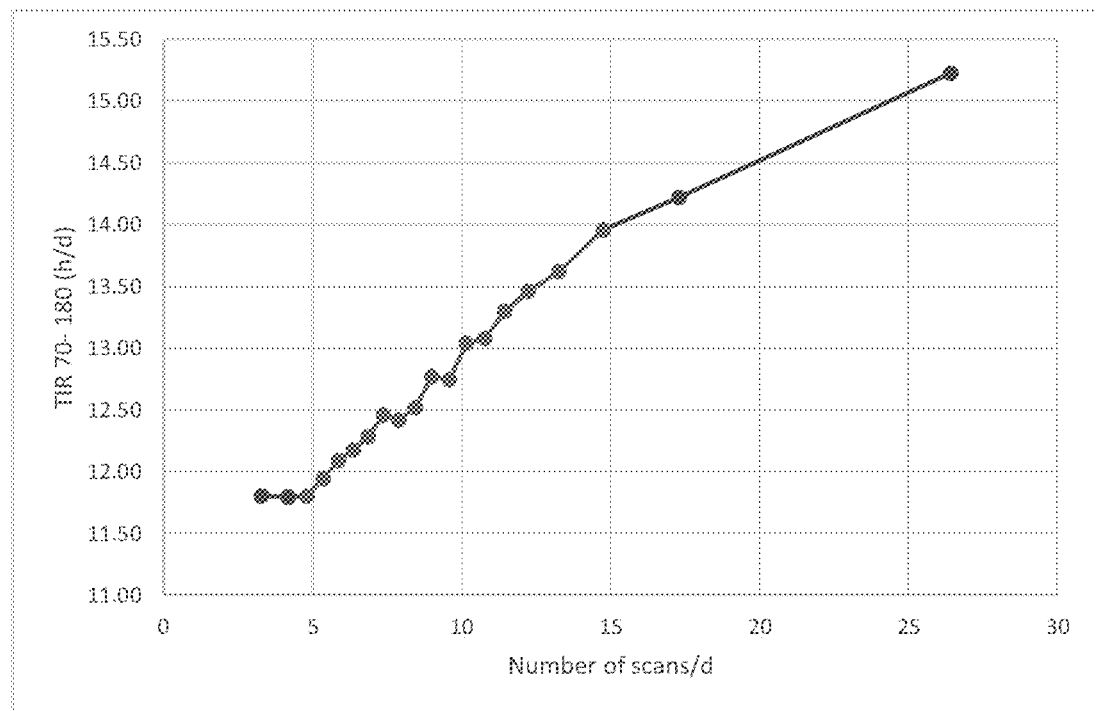

As can be seen in FIG. 14C, hyperglycemia indicators improve as the daily frequency of scans increases. Indeed, each additional "scan" can therefore provide a benefit to the metabolic balance, particularly between 8 and 15 scans per day. For example, T>180 and T>240 decreases with the frequency of scans. The group that scans the most reduced the T>180 by 33% compared to the group who scans the least (7.3 vs. 10.9 hours, p<0.001). Similarly, as can be seen in FIG. 14E, each additional scan results in an increase of the TIR 70-180 by 11±8 min/d (i.e., a range of 3-19 min/d). As can be seen in FIG. 14E, TIR 70-180 is increased by 2.2 h per day (i.e. a gain of 9% of the time in the target) for a scan frequency increasing from 3 to 14 scans while the gain is only 1.3 h (i.e. +5%) for a scan frequency above 14 scans per day. Accordingly, the slope (i.e., 1.3 hours divided by total scans per day) shown in FIG. 14E, is approximately 7 minutes per day per user scan. Therefore, each additional scan results in an increase of in time in range of 7 minutes per day per scan. As such, the improvement in time in range below the inflection point of 14 scans per day (i.e., 11 minutes per day per user scan) is unexpectedly greater than the improvement above the inflection point of 14 scans per day (i.e., 7 minutes per day per scan).

Having more access to glucose concentrations during the day, which is easier with a CGM system (e.g., in certain embodiments, the FreeStyle Libre system), enables the patient to reduce the time spent in hyperglycemia thanks, among other things, to prandial bolus or more regular and adapted corrections.

Additionally, the impact on hypoglycemia indicators, especially T<70, of the increase in frequency as well as the coefficient of variability is "biphasic". Specifically, scanning 3 to 8 times a day increases T<70 and coefficient of variation (CV); scanning more than 8 times a day, with a benefit observed for each additional scan, the time spent in the values below the target and the CV decrease. Intensification of insulin treatment leading to an improvement in HbA1c is known as being accompanied by a greater frequency of hypoglycemia. However, as shown by this analysis, multiplication of controls facilitated by use of a flash continuous glucose monitor can makes it possible to anticipate hypoglycemic episodes and accelerate their resolution, thereby reducing the time spent in hypoglycemia. Accordingly, only with a sufficient number of scans each day could the time spent in hypoglycemia be reduced.

Figure 14F:
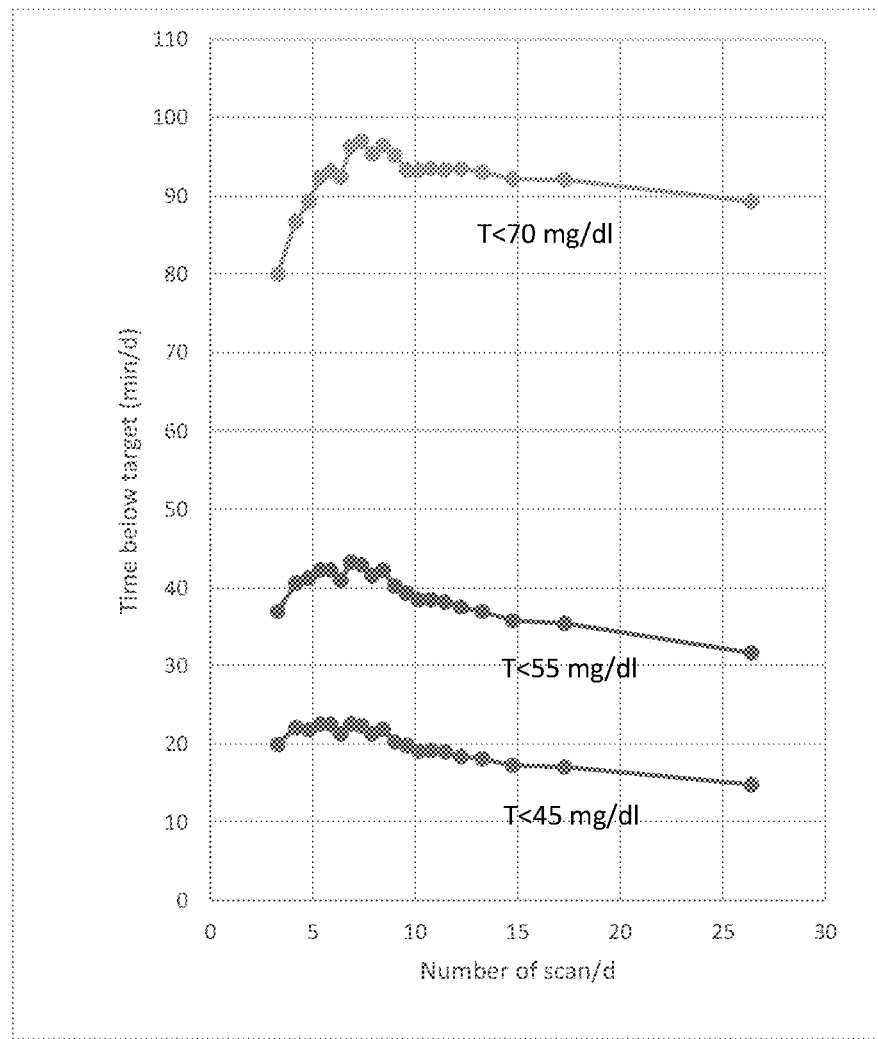

On average, T<70 increases in patients who scan 8/day compared to those who scan only 4/day (+16 min/d or +1.1%). As can be seen in FIG. 14F, this evolution profile is less marked for T<55 (+5 min/d) and for T<45 (+2 min/d). As can be seen in FIG. 14F, above 8 scans per day, T<70, T<55, T<45 decrease.

Additionally, mean glucose was converted to an estimate of Hba1c (estimated HbA1c) using techniques known to a person of skill in the art. One such technique is disclosed in Nathan et al., *Translating the A1C Assay into Estimated Average Glucose Values*, Diabetes Care 2008; 31(8):1473 8, which is incorporated herein by reference in its entirety. As can be seen in FIG. 14I, estimated HbA1c decreases with the daily scan frequency increasing. In particular, estimated HbA1c for the lowest scanning group (mean 3.3 scans/day) is 8.11% (95% CI: 8.06-8.15%) and for the highest scanning group (mean 26.4 scans/day) is 7.03% (95% CI: 7.00-7.06%, p<0.001). Each additional scan results in a reduction of the estimated HbA1c by an average of 0.07±0.05% (i.e., a range of 0.02-0.12%). As can be seen in FIG. 14D, when the scanning frequency is increased from 3 to 14 scans per day, the estimated reduction in HbA1c is 0.8%. When this frequency is increased from 15 to 26 scans per day, the estimated reduction in HbA1c is only 0.3%. Accordingly, the slope (i.e., 0.03% overall reduction in estimated HbA1c divided by total scans per day) shown in FIG. 14D, is 0.03%. Therefore, each additional scan results in a reduction of the estimated HbA1c by an average of 0.03%. As such, the improvement in estimated HbA1c below the inflection point of 14 scans per day (i.e., 0.07% per user scan) is unexpectedly greater than the improvement above the inflection point of 14 scans per day (i.e., 0.03% per user scan).

Figure 14G:
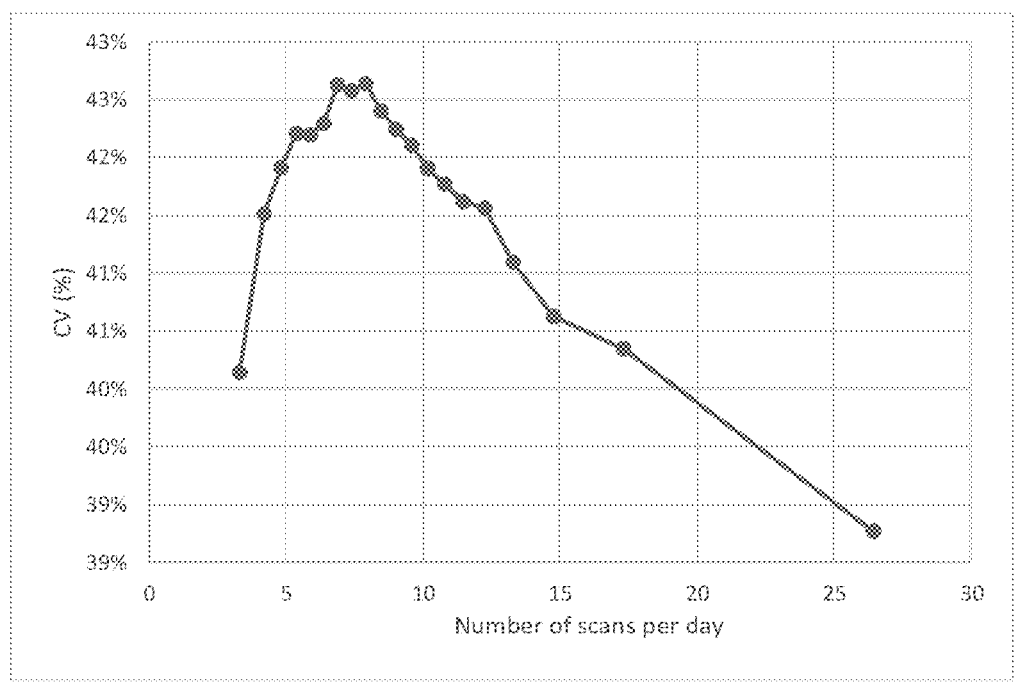

The coefficient of variation (CV) was evaluated from the mean blood glucose level over the full data set. As can be seen in FIG. 14G, CV also follows a bi-phasic evolution with an increase in patients who on average scan 8/day compared to those who scan only 4/day (+3%) and then a reduction in those who scan more.

According to embodiments, the metabolic parameter is HbA1c. In some embodiments, the instructions, when executed by the one or more processors, can cause the one or more processors to output the first notification and second notification if HbA1c is at or above a predetermined level. According to embodiments, ss can be seen in FIG. 14D, the first improvement can be a reduction in HbA1c of 0.02-0.12% per user operation of the reader device. According to embodiments, as can be seen in FIG. 14D, the first improvement can be a reduction in HbA1c of at least 0.07% per user operation of the reader device. According to embodiments, as can be seen in FIG. 14D, the second improvement can be a reduction in HbA1c of at least 0.03% per user operation of the reader device. According to embodiments, the user operation of the reader device can include a user scan of the data processing unit with the reader device.

According to embodiments, the metabolic parameter is time spent in hypoglycemia. In some embodiments, as can be seen in FIG. 14F, the predetermined target level of interaction is 8 scans per day.

According to embodiments, the metabolic parameter is time in target range. In some embodiments, the instructions, when executed by the one or more processors, can cause the one or more processors to output the first notification and second notification if the time in target range is at or below a predetermined level. According to embodiments, as can be seen in FIG. 14E, the first improvement can be an increase in time in target range of 3-19 minutes per day per user operation of the reader device. According to embodiments, as can be seen in FIG. 14E, the first improvement can be an increase in time in target range of 11 minutes per day per user operation of the reader device. According to embodiments, as can be seen in FIG. 14E, the second improvement can be an increase in time in target range of approximately at least 7 minutes per user operation of the reader device. According to embodiments, the user operation of the reader device can include a user scan of the data processing unit with the reader device.

According to embodiments disclosed herein and discussed below, the predetermined target level of interaction may vary, for example, not limitation, based on country, population characteristics, insurance coverage, etc.

EXAMPLE 2

In accordance with an embodiment as described here, independent investigations of smaller scale reinforced similar reductions in user's metabolic parameters corresponds to frequency of user interaction. For example, flash glucose monitoring was introduced in a cohort of patients with type 2 diabetes mellitus treated with multiple daily injection therapy who had previously only used a traditional finger prick method (i.e., self-monitoring blood glucose test) of blood glucose monitoring. Introduction of flash glucose monitoring was shown to be associated with improvements in markers of glycemic control and self-reported patient satisfaction, as well as decreases in perceived and actual episodes of hypoglycemia, total daily dose of insulin, body mass index and waist-to-height ratio, despite a relatively short study duration.

Patients were invited to participate if they were aged 20-75 years, had a diagnosis of type 2 diabetes mellitus, an HbA1c ≥7% (or fasting blood glucose ≥110 mg/dL, <250 mg/dL), prescribed a multiple daily injection insulin regimen for at least one year, used conventional self-monitoring blood glucose test to test their glucose levels at least two times per day, had no prior experience of flash glucose monitoring or any other continuous glucose monitoring system, and attended regular follow-up appointments. Individuals were not included if they had a history of pancreatitis, severe infections, severe mental illnesses or malignant disease; history of serious vascular diseases (such as stroke or myocardial infarction) within six months prior to the initiation of the study, pregnancy or planned future pregnancy or were deemed as unfit to participate by the primary physician.

At the baseline visit, a flash glucose monitor sensor was attached to the back of the patient's upper arm by a trained diabetes educator. Patients were educated and trained on the proper application of the sensor and followed instructions as per label. Patients were advised that, as far as possible, current glucose levels should be checked by scanning the sensor at least every eight hours. In addition, participants were advised to confirm sensor glucose levels with a self-monitored blood glucose test during unsteady glucose states, during impending or suspected hypoglycemia, and if their sensor readings did not match their symptoms. Demonstrations were given on how sensor glucose levels could be confirmed with a capillary measurement using the blood glucose meter in-built in the reader of the flash glucose monitoring system. At the end of study, sensor data were downloaded to a computer to produce the reports, including the ambulatory glucose profile, in order to identify the number of scans performed during the study period.

Additionally, at the baseline visit, demographic characteristics including age, sex, height and weight and duration of diabetes were recorded. At baseline and the 12-week visits, clinical characteristics including frequency of SMBG or flash glucose monitoring scans per day, number of SMBG confirmed hypoglycemic episodes per month, total daily dose of insulin and HbA1c were recorded.

Further, at baseline and at 12 weeks, participants completed the Arabic versions of the Diabetes Treatment Satisfaction Questionnaire—Status Version (DTSQs) and, at 12 weeks, the Diabetes Treatment Satisfaction Questionnaire—Change Version (DTSQc). Additionally, at baseline and at the 12-week visits, participants completed the Glucose Monitoring Satisfaction Survey (GMSS) version type 2 diabetes mellitus. The GMSS questionnaire is focused particularly on satisfaction with the mode of glucose monitoring, and responses give rise to four summary scores: emotional burden, behavioral burden, openness and worthwhileness, where higher scores indicated greater perceived levels of these parameters.

Summarized parameters were expressed as mean±standard deviation (SD) and range. The statistical significance of changes between patients' paired baseline and 12-week data was determined by way of the two-tailed Student's t-test or the Wilcoxon-Mann-Whitney U test, depending on outcomes of normality testing of timepoint differences ($\alpha=0.05$), and were expressed as mean±standard deviation and 95% confidence interval (CI). The associations between clinical parameters such as HbA1c, frequency of daily monitoring and rate of hypoglycaemic episodes were assessed by visual inspection of scatter plots and calculation of Pearson's product-moment correlation coefficient. The association between changes in clinical parameters and treatment satisfaction were calculated in a similar fashion. Additional exploratory analysis was conducted, particularly on the association of age and scan frequency. All statistical analysis was conducted in R version 4.0.1.

Reductions in HbA1c were experienced fairly systematically by all subjects. A statistically significant improvement was observed in HbA1c at 12 weeks, which fell by 0.44% ($p<0.001$) from 8.22%±0.69 (mean±SD) at baseline to 7.78±0.71 at 12 weeks. There was a greater absolute drop in HbA1c in participants with a higher HbA1c at baseline. Moreover, those with higher baseline BMI (>30) experienced a greater absolute drop in HbA1c as well as a greater drop relative to baseline HbA1c measures (BMI>30, absolute $\Delta$HbA1c=−0.47%, relative $\Delta$HbA1c=−5.54%; BMI<30, absolute $\Delta$HbA1c=−0.39%, relative $\Delta$HbA1c=−4.45).

As seen in FIG. 15B, at baseline, the number of confirmed hypoglycemic episodes experienced varied from two to eight per month) which fell by a mean of 3.19 episodes per month ($p<0.001$), from 4.43±1.51 episodes/month to 1.24±1.15. Total daily dose on insulin fell by 0.43 units/kg/day ($p<0.001$, table 2).

Monitoring frequency, indicated by the number of scans per day, increased with the use of flash glucose monitoring. In particular, participants performed significantly more sensor scans per day, compared to self-monitored blood glucose frequency at baseline, with a mean increase of 5.13 monitoring episodes per day ($p<0.001$, table 2). Notably, scanning rate three times that of self-monitored blood glucose frequency at baseline was observed, which supports the rationale that convenient access to interstitial glucose measures is empowering for patients.

The majority of participants experienced weight loss. Overall change in mean body mass index was modest ($p<0.001$).

Figure 15C:
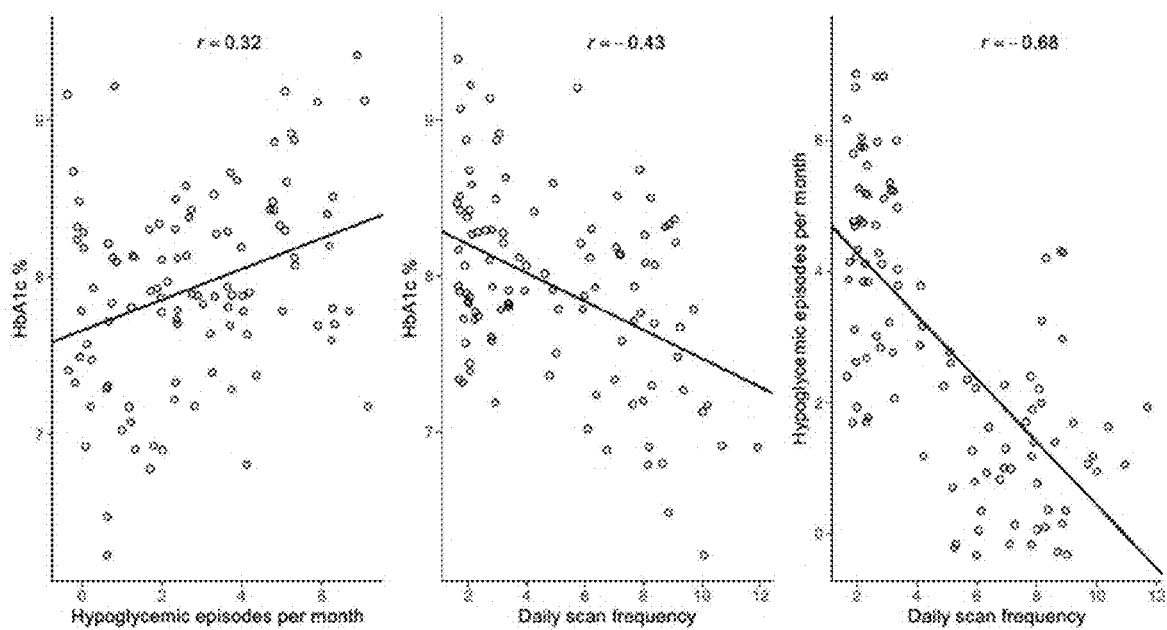
Figure 15D:
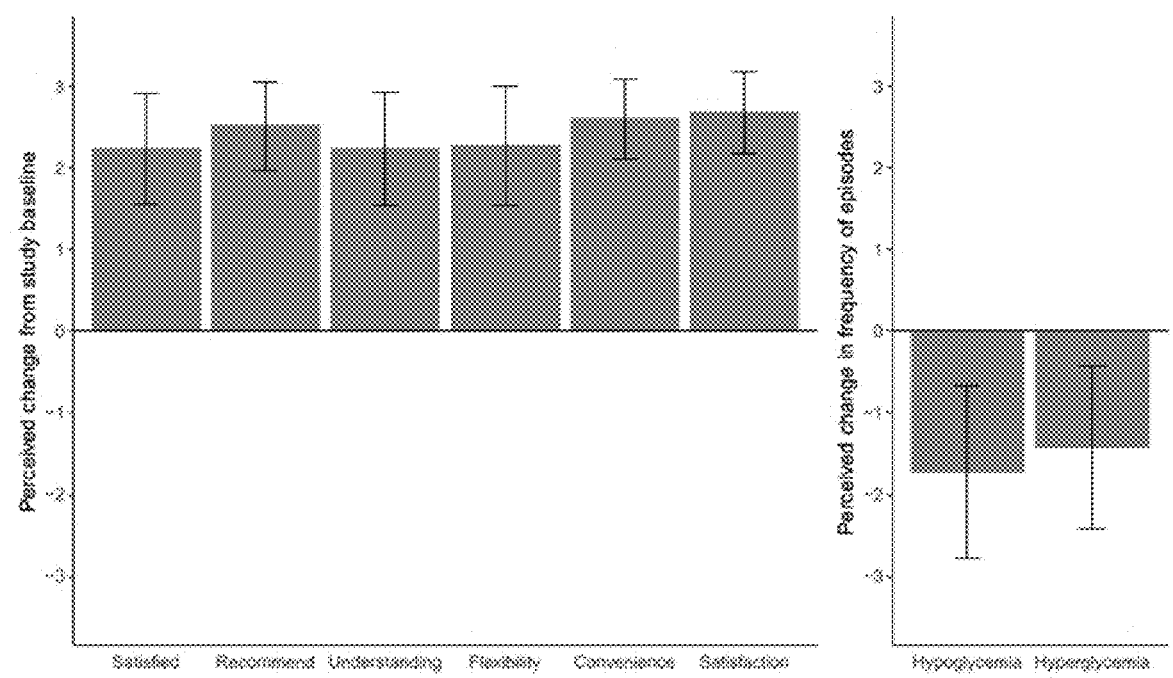

FIG. 15C illustrates a correlation analysis, wherein linear relationships were found between HbA1c level and daily scan frequency ($r=-0.43$, $p<0.001$), between the frequency of hypoglycemic episodes per month and daily scan frequency ($r=-0.68$, $p<0.001$), and between HbA1c level and the frequency of hypoglycaemic episodes per month ($r=0.32$, $p<0.001$).

Exploratory analysis revealed that mean scan frequency did not significantly differ when the cohort was split into three age bands (25-34, 35-44 and >45 years), either at baseline or at 12 weeks, which supports the notion that this technology device is easy to use.

In this embodiment, correlations between measures of patient satisfaction and clinical measures, which serve as cross-validity as well as underscoring the central importance of patients' wellbeing with regard to adherence to treatment regimens, were identified. This is particularly pertinent in diabetes, where issues of societal stigma are still prevalent and pervasive, accentuated by the fact that the burden of management rests upon the patients themselves.

Figure 15E:
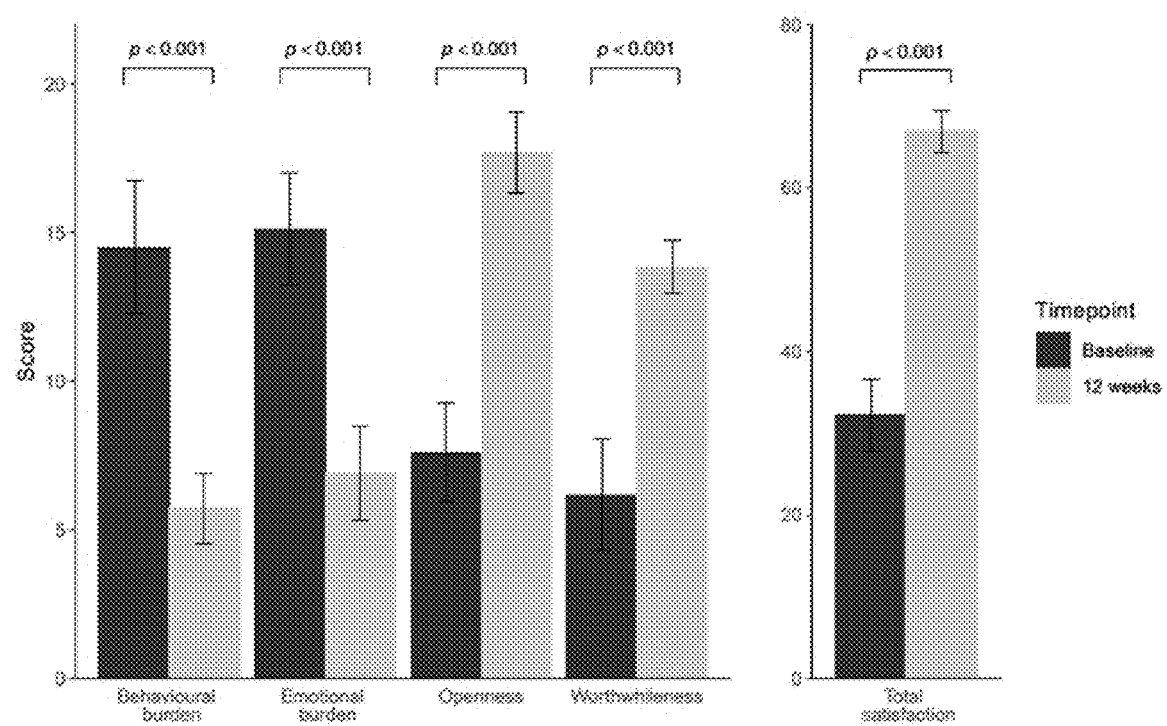

Outcomes of DTSQs completed by all subjects at baseline, expressed as mean±standard deviation, are as follows: the combined total treatment satisfaction score was 14.1±2.56 (range, 9-20; range of possible scores, 0-36); the combined score of perceived episodes of hypo- or hyperglycemia was 7.33±1.52 (range, 4-10; range of possible scores, 0-12). As can be seen in FIG. 15E, there is clear perceived improvements across all questions relating to satisfaction relative to baseline. Outcomes of DTSQc also clearly evidence a reduction in the perceived rates of hypo- or hyperglycemic episodes.

As can be seen in FIG. 15E, GMSS scores improved across all four categories as did overall treatment satisfaction ($p<0.001$ for all categories. Two-fold, statistically significant improvements were experienced from baseline to 12 weeks across all four categories of behavioral burden (14.5±2.23 vs. 5.72±1.19, $p<0.001$, CI: 8.00, 9.50), emotional burden (15.1±1.88 vs. 6.87±1.58, $p<0.001$, CI: 7.50, 9.00), openness (7.59±1.65 vs. 17.7±1.37, $p<0.001$, CI: 9.50, 11.0) and worthwhileness (6.17±1.87 vs. 13.8±0.91, $p<0.001$, CI: 7.50, 8.00). Similarly, the total treatment satisfaction score doubled over the course of the study (32.2±4.39 vs. 66.9±2.63, $p<0.001$, CI: 33.5, 36.0).

A negative linear correlation was identified between HbA1c levels and GMSS total treatment satisfaction ($r=-0.32$, $p<0.001$), and similar correlation trends were found between HbA1c levels and the four summary categories of the GMSS.

EXAMPLE 3

Adequate and timely glucose level assessment is indispensable for patients with diabetes mellitus (DM) treated with multiple daily injections (MDI) or continuous subcutaneous insulin infusion (CSII) when aiming for adequate glycemic control. Glucose measurements enable patients and caregivers to make insulin dose adjustments and to aim for changes in lifestyle and dietary habits, which will help to improve metabolic control. Ultimately, with optimized glycemic control micro- and macrovascular complications can be delayed or prevented.

Finger prick testing according to present techniques in the art can suffer from several drawbacks. Since they are point measurements, information on glucose trends is limited. Many patients feel reluctant to perform finger pricks many times daily, since it can be disruptive to daily activities and painful. Continuous glucose monitoring (CGM), either by real time Continuous Glucose Monitoring (rt-CGM) or by Flash Glucose Monitoring (FLASH), can allow a more frequent assessment of glucose concentrations in the interstitial fluid and can also provide information on glucose trends. CGM is changing diabetes management and often contributes to increased quality of life, treatment satisfaction, better and more stable glycemic control and improved short-term outcomes.

FLASH is becoming increasingly available and increasingly used by patients. In an embodiment, magnitude of FLASH reader use in the Netherlands during the period September 2014 to March 2020 was measured and examined the associations between FLASH scan frequency and glycemic parameters under real life circumstances.

Completely anonymized information on the use of scanning devices and connected sensors was accumulated from a database. The available data can contain various information, including, information on which country the data was collected from. In addition to data from Dutch users, data from users from other countries can be retrieved from the database for comparisons. The duration of FLASH monitoring, the number of readers and sensors and the scanning frequency per sensor and individual scanning device could be determined. The scanning frequency for each sensor was calculated by the number of scans divided by the duration of sensor use according to recorded start and end times. Scanning frequency per reader was assessed by calculating the mean scan rate of all its sensors, followed by determining the cumulative frequency distribution and summary metrics (mean, median and interquartile range (IQR)). To investigate patterns of scanning, frequency of scanning per day and per hour was collected.

In an embodiment, the FLASH monitors glucose levels in interstitial fluid for up to 14 days. A dedicated reader (e.g., a smartphone application, software, reader device, etc.) is used to scan the FLASH sensor to collect the current glucose, such as, for example, the last 8 h history and glucose trend. In an embodiment, up to 8 hours of glucose readings are automatically stored every 15 min on the sensor. In an embodiment, other time ranges are also contemplated. When a reader was connected to personal computer-based software with an internet connection, the reader's 90-day memory was de-identified and uploaded to a database.

Once data was collected, various analyses could be performed. To be included in these analyses each sensor had at least 120 operational hours, at least in part to ensure reliable glucose control measures. Data from all sensors belonging to the same reader were combined and calculated as the mean of all sensor measures. The cumulative frequency of scan rates was calculated for each five percent of available readers to stratify the readers into 20 equally sized groups (bins), and descriptive statistics were calculated. The frequency distribution of scans by hour of the day was assessed for scanning patterns across the day. Several measures of glycemia were used including mean glucose, time in euglycemic range (defined as glucose between 3.9 and 10 mmol/L), time in hyperglycemia (>10 mmol/L and >13.9 mmol/L) and time in hypoglycemia (<3.9 mmol/L and <3.0 mmol/L) (17). The available information on glucose per scanner was converted into eHbA1c using an algorithm (eHbA1c (%)= (mean glucose in mmol/L+2.59)/1.59) (18). eHbA1c is presented in IFCC (mmol/mol) and DCCT/NGSP units (%).

Statistical comparisons across the groups were performed by one-way analysis of variance (ANOVA), and the span of glycemic measures and relative changes were reported from the lowest to highest scan rate groups. The database was analyzed by structured query language routines, and further summarized by KNIME (www.knime.org), the Python programming language (www.python.org), and the R statistical package (www.r-project.org). In view of the large sample size and multiple comparisons, only p values <0.01 were considered statistically significant. Confidence intervals were calculated for each group, mean of each measure for each scan rate group, and comparisons were made across the bins.

One outcome of the analyzes was the association between FLASH (scan) frequency and glycemic parameters (estimated HbA1c (eHbA1c), time in eu-, hyper-, and hypoglycemia, and standard deviation of glucose). As secondary outcome, scan frequency during eu-, hypo- and hyperglycemia was assessed for persons with lower and higher eHbA1c values. In addition, the number of obtained glucose readings in the Netherlands, their pattern across the day and comparisons with worldwide data were assessed.

Figure 16C:
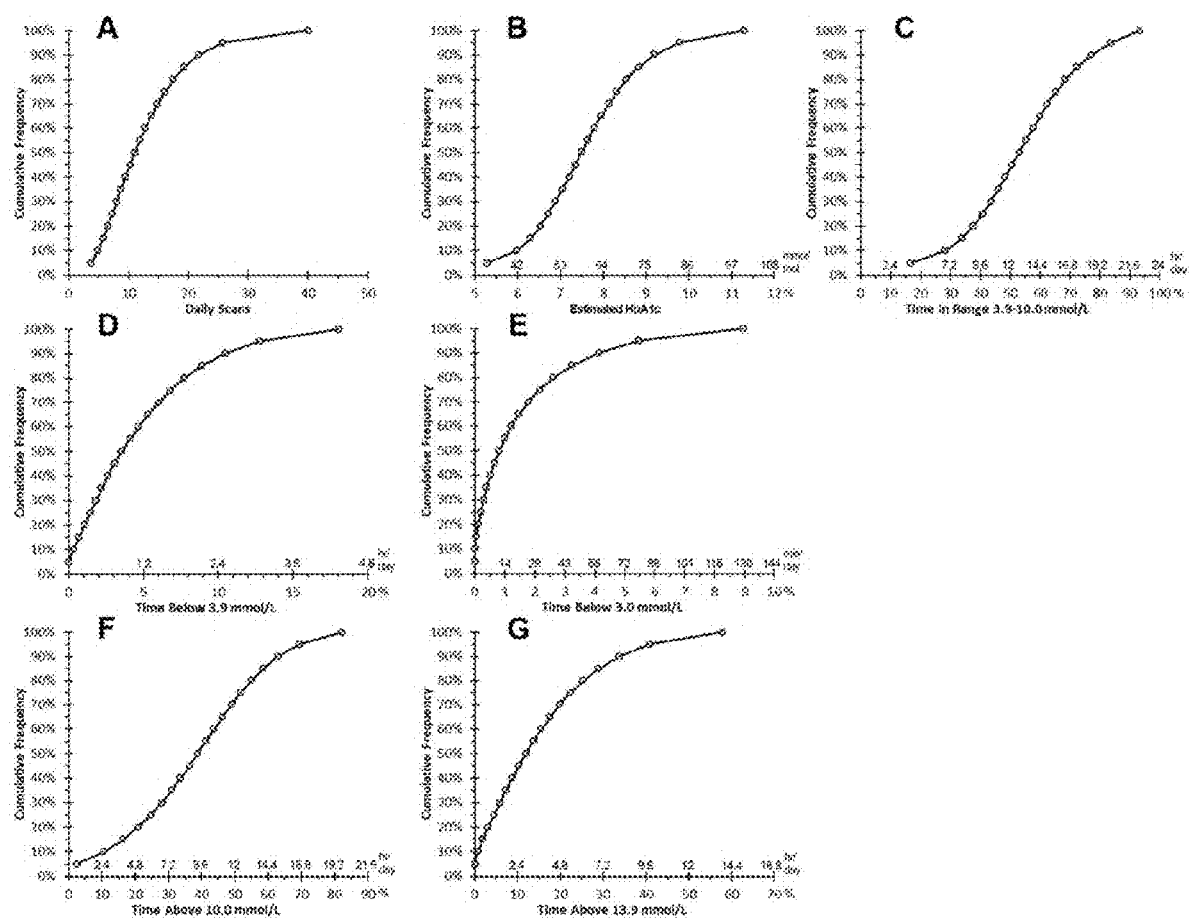

As shown in FIG. 16A, in this exemplary embodiment, there were 16,331 analyzable readers (163,762 sensors) from the Netherlands, out of a total of 932,793 (10,348,827 sensors) across all countries. There were 27.9 million glucose scans performed by the users in the Netherlands, and the sensors provided 48.7 million hours of glucose monitoring data. The median [IQR] number of daily scans in the Netherlands was 11.5 [7.7, 16.7] as illustrated in FIG. 16C). During day hours (6 AM to 10 PM) this number was 8.9 [5.9, 13.2] and during night hours (10 PM to 6 AM) 2.4 [1.6, 3.6]. There were no significant differences in scan frequency between the different days of the week.

As illustrated in FIG. 16B, the 20 bins stratified by mean daily scan rate can be analyzed for the associated glycemic metrics. The lowest 5% of readers (n=817) had a mean scan rate of 3.7 scans per day, with a mean eHbA1c of 71 mmol/mol (8.6%), while the 5% of readers with the highest scan frequency had a mean scan rate of 40.0 scans per day and a mean eHbA1c of 52 mmol/mol (6.9%). Indices of glycemia are also presented in FIG. 16C.

Figure 16D:
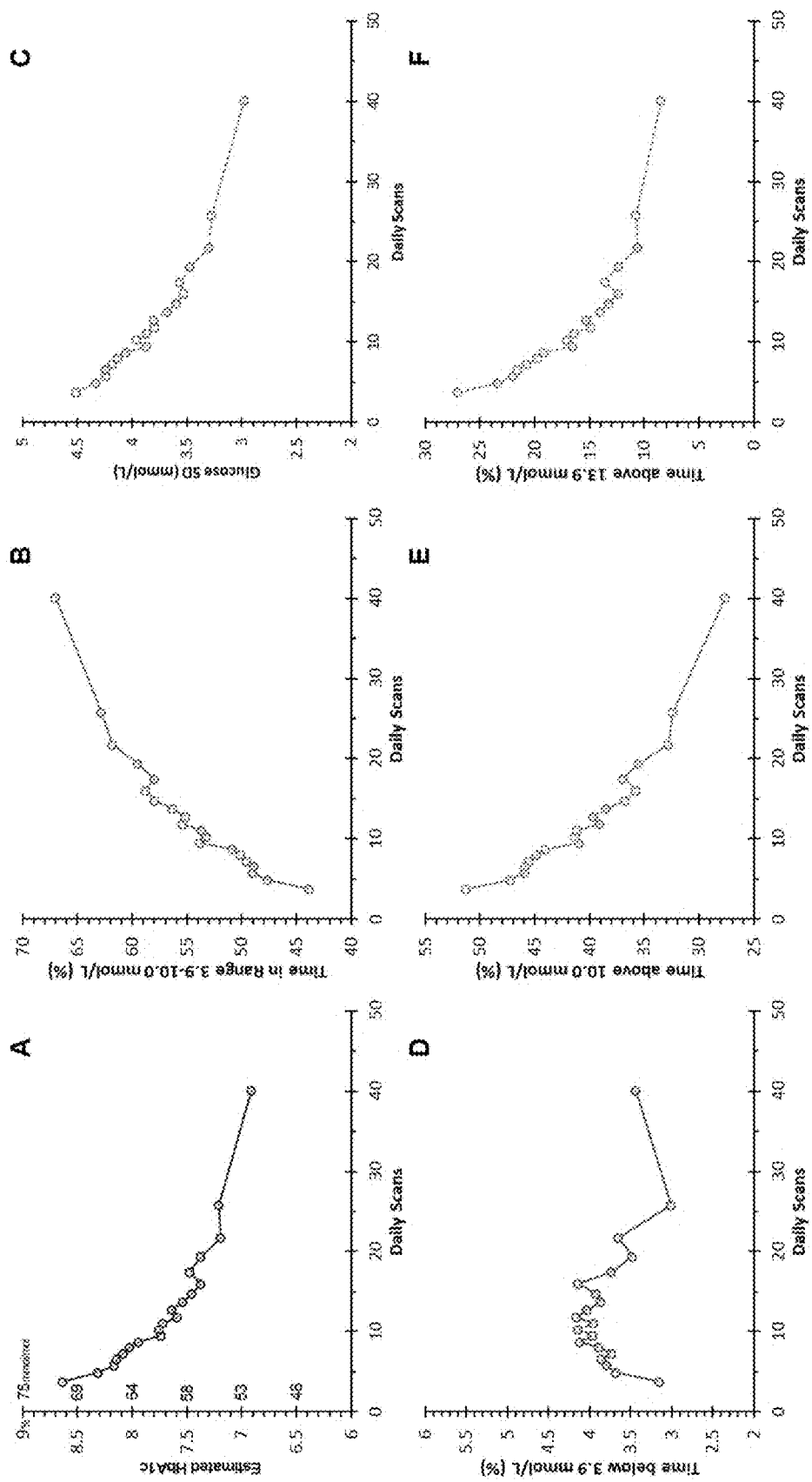

Associations of scan rate with eHbA1c, time in eu-, hyper-, and hypoglycemia, and standard deviation of glucose are presented in FIG. 16D. Overall, per bin with increasing scan frequency an association with lower eHbA1c levels, less time in hyperglycemia and improved glucose variability (expressed as a lower standard deviation) can be observed. Within the bin that represents persons who scanned more than 40 times per day an eHbA1c below 53 mmol/mol (7.0%) has been achieved. The association of scanning frequency with time in hypoglycemia was less pronounced, as shown in FIG. 16D.

Figure 16E:
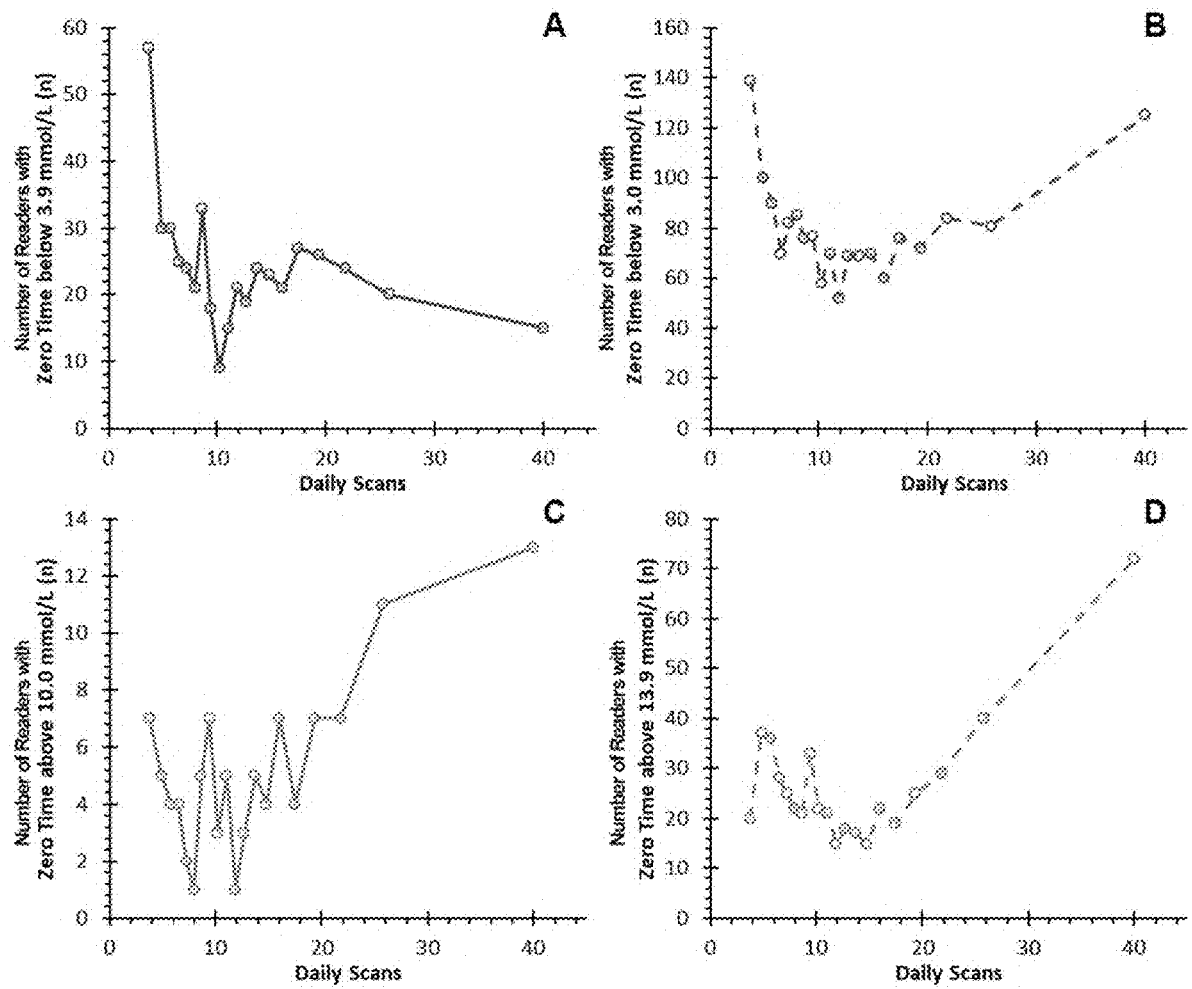

FIG. 16E illustrates an evaluation of the number of readers in each bin with zero time in hypo- and hyperglycemia. At hypoglycemia with a glucose level <3.0 mmol/L (54 mg/dl), there was a decrease followed by an increase in the number of readers with zero exposure to this level of hypoglycemia across the scan groups. For zero exposure to hyperglycemia, the association was clearer; persons with higher scan rates were more likely to have zero time in hyperglycemia. Concerning hyperglycemia above 13.9 mmol/L (250 mg/dl), at the highest scan group of 40 scans per day, 72 of 817 (8.8%) readers had no exposure to this level of hyperglycemia.

Figure 16F:
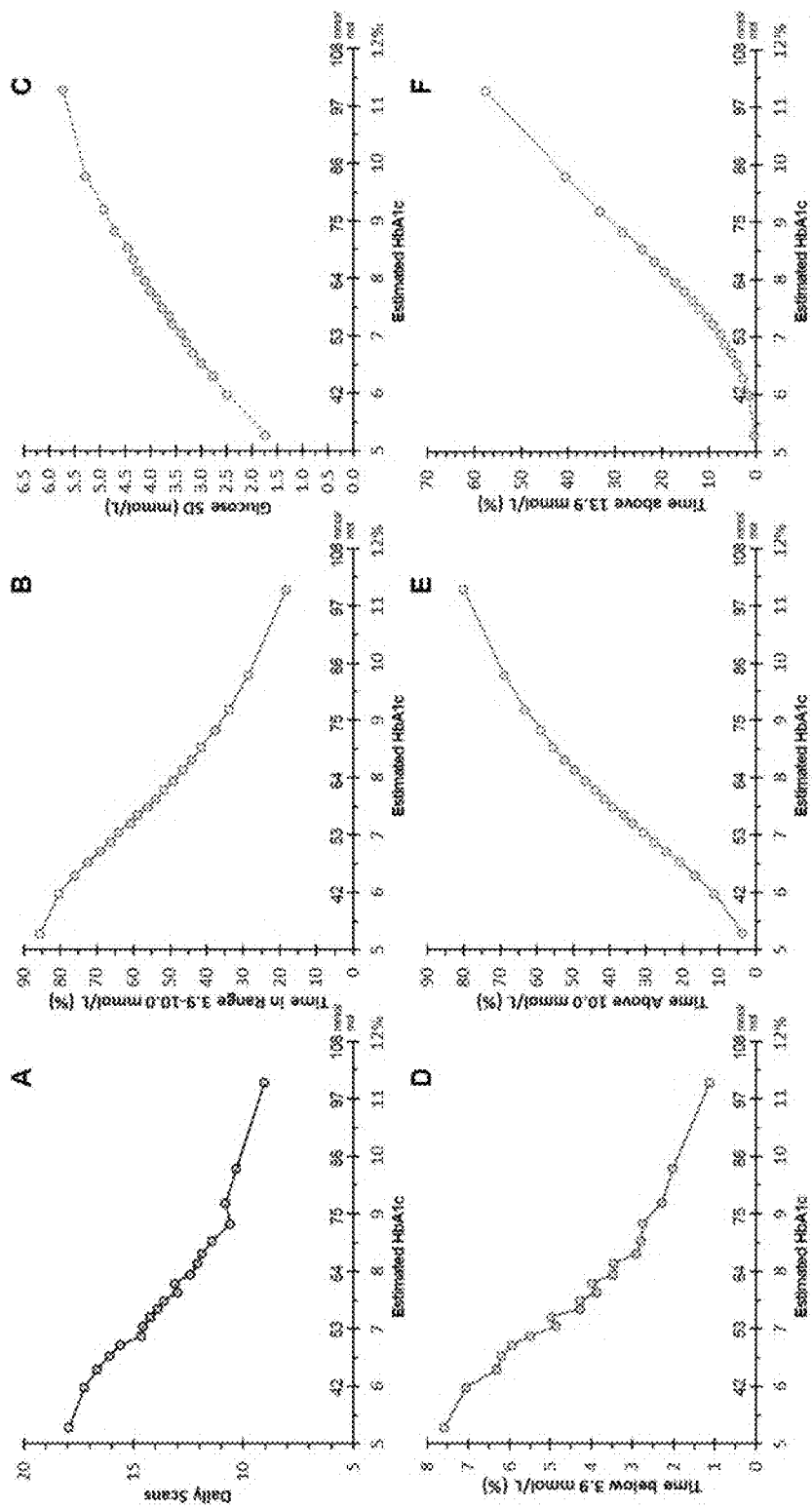

FIG. 16F illustrates grouping the readers into 20 equal bins defined by eHbA1c. This figure further illustrates that the highest eHbA1c bin performed just under 10 scans per day, while the lowest bin had a daily scan rate of 18 per day. An association with other glucose metrics can also be observed; those with the lowest eHbA1c had the highest time in eu- and hypoglycemia, and lowest time in hyperglycemia. For glucose variability, there is an increasing relationship between eHbA1C and standard deviation of glucose levels. Of notice, an eHbA1c of 53 mmol/mol (7.0%) corresponded with a scan frequency of 15 scans per day and translated in approximately 65% time in euglycemia, 30% time in hyperglycemia (>10 mmol/L) and 5% time in hypoglycemia (below 3.9 mmol/L)

Figure 16G:
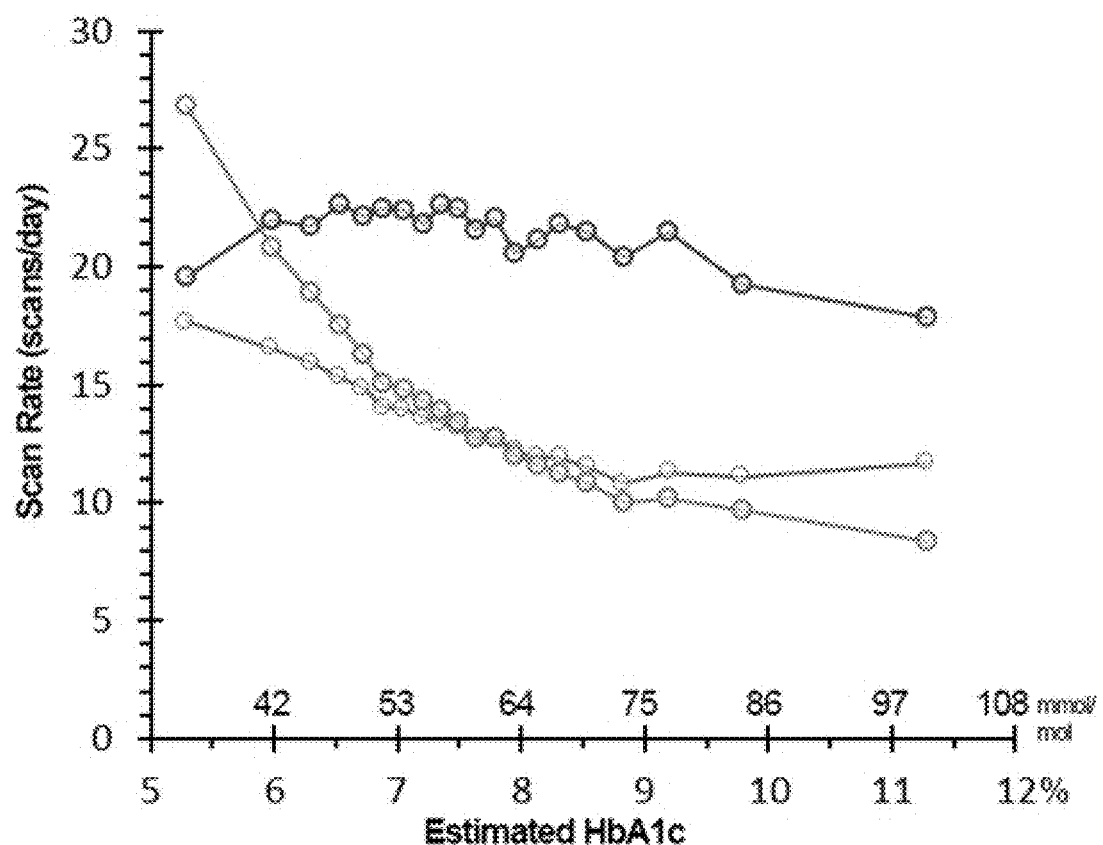

FIG. 16G illustrates the scan behavior between eHbA1c groups in more detail with scan rates (scaled to units of scans per day) during each glucose range determined for each bin. During eu- or hyperglycemia persons with lower average estimated HbA1c values tend to scan more frequently as compared to those with higher estimated HbA1c values, whereas the scan frequency in hypoglycemia tends to stay relative stable over the different average eHbA1c levels.

Figure 16H:
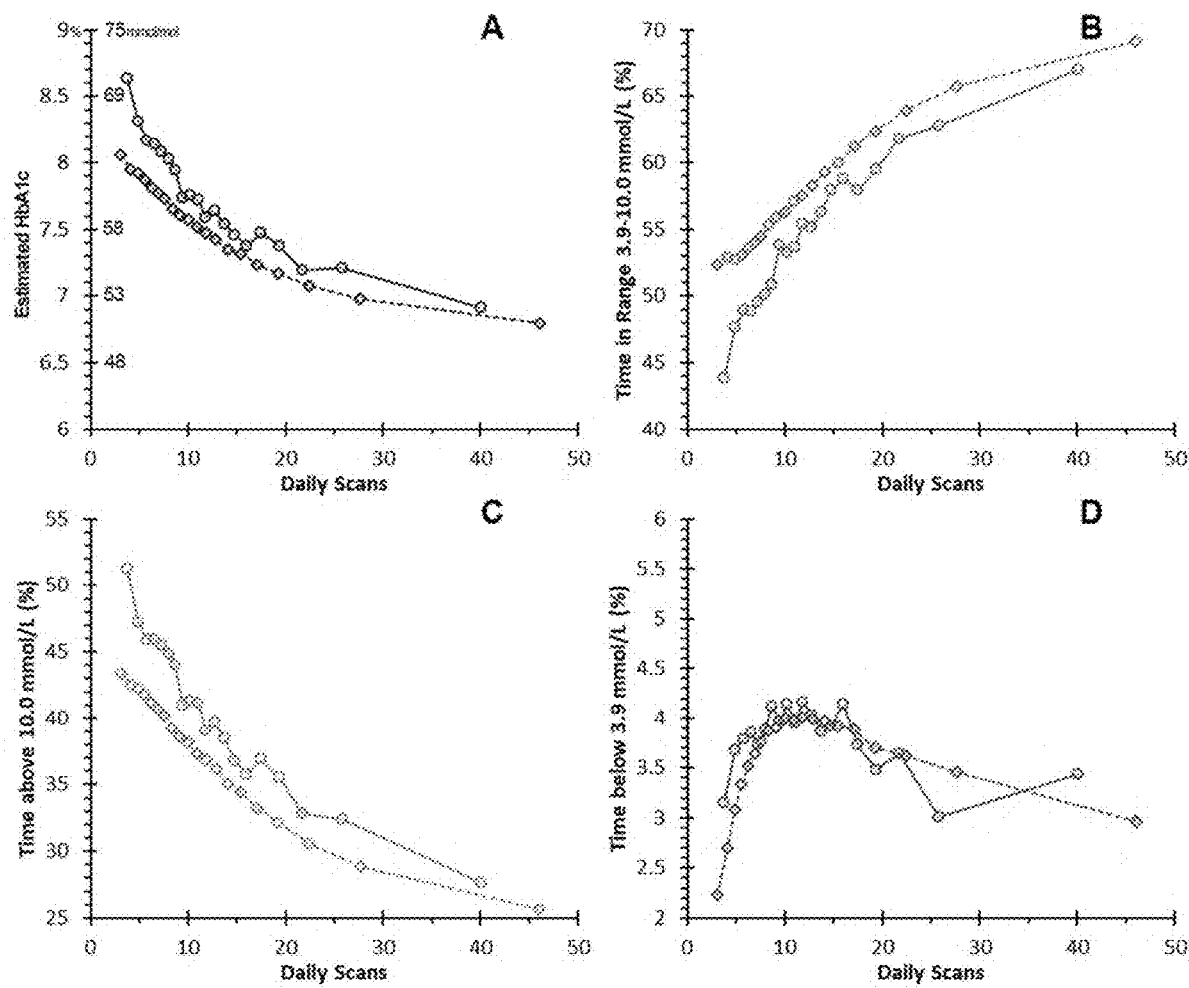
Figure 16I:
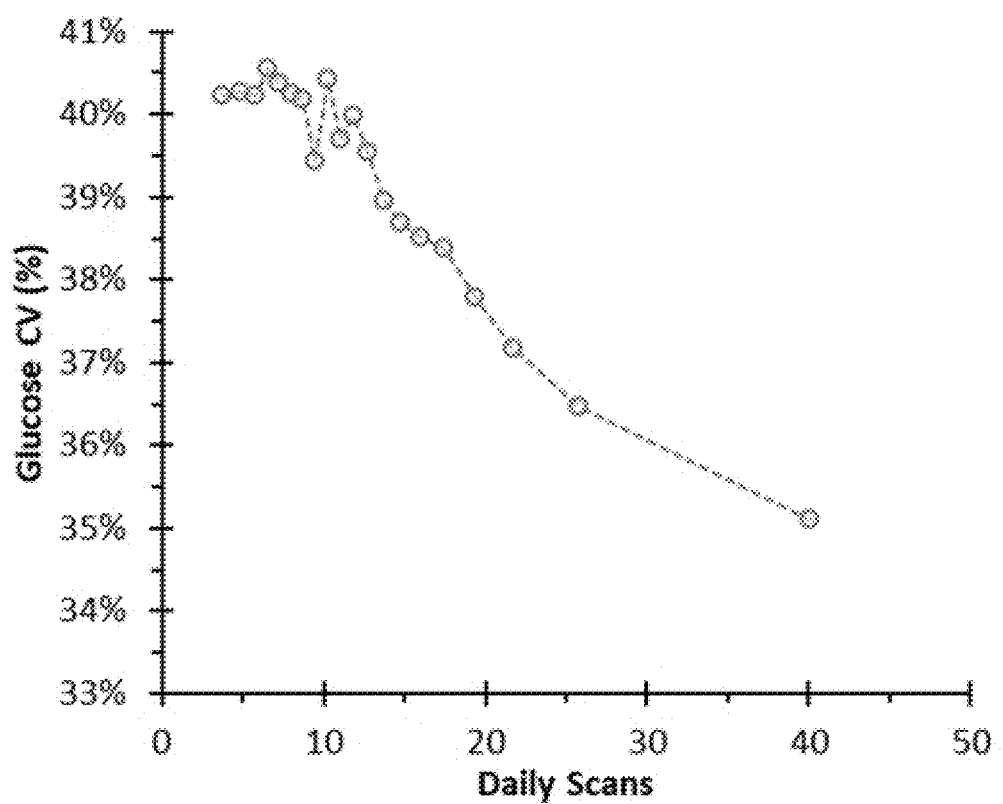

FIGS. 16A and 16H illustrate a comparison of data from the Netherlands with certain worldwide data is presented. Overall, there was a similar daily scan rate (mean 13.4 vs. 13.2) and parameters of glycemia demonstrate a slightly higher HbA1c (61 (15.3) vs. 58 (16.4) mmol/mol) and less time in euglycemia (13.1 (4.5) vs. 13.9 (4.9) hours per day) in the Dutch population.

As outline in the results above, in this embodiment, there can an association between increasing scan frequency with better glycemic control. In general, a scanning frequency of >20 times per day is associated with an eHbA1c level close to 53 mmol/mol (7.0%). The other way around: the lower the daily scan frequency, the higher the associated eHbA1c. Furthermore, persons who scan with low frequency tend to concentrate scanning in the hypoglycemic range and tend to disregard scanning in the hyperglycemic range. This suggests that users with a low scan rate potentially do not reap the benefits of FLASH compared to users who scan more frequently.

A scanning frequency to reach an eHbA1c level of <53 mmol/mol—currently the most often used target for HbA1c levels—corresponds with a time in euglycemia (glucose 3.9-10.0 mmol/L) of 65% in our analysis. This finding emphasizes the difference between eHbA1c (more stable) and time in range as (more dynamic) outcome parameter. When educating healthcare professionals and FLASH users, these findings can be incorporated, aiming for a more satisfactory use of FLASH. In contrast to more recent CGM devices, the FLASH analyzed according to this embodiment has no alarm function for (predicted) hypo- or hyperglycemia.

EXAMPLE 4

In this exemplary review, several studies were examined for evidence related to the flash glucose monitoring system in patients with T2D, although several real-world studies had mixed type 1 diabetes (T1D) and T2D populations. These studies are tabulated in FIGS. 17B-D. Additional details of this embodiment are disclosed in *A review of flash glucose monitoring in type 2 diabetes*, which was originally published in Diabetology & Metabolic Syndrome, Volume 13, Article Number 42, 2021, BMC and can be accessed at the website https://dmsjournal.biomedcentral.com/articles/10.1186/s13098-021-00654-3, and is incorporated by reference herein in its entirety.

To identify clinical trials of the flash glucose monitoring system, searches were conducted of PubMed and Google Scholar from inception to 30 Jun. 2020 using the search terms flash glucose monitoring; continuous and/or intermittent glucose monitoring; and FreeStyle Libre system. No language restrictions were applied. Reference lists of retrieved papers were hand-searched for additional clinical studies and other articles of interest. Relevant abstracts presented at the American Diabetes Association Congress in June 2020 were also considered for inclusion.

The benefits of the flash glucose monitoring system in improving glycemia in T1D were shown in the IMPACT randomized controlled trial (RCT) of 239 randomized patients, and subsequently in a large real-world study (n=1913).

In the IMPACT study, which is incorporated by reference in its entirety herein, of adult patients with well-controlled T1D (glycosylated hemoglobin [HbA1c]≤7.5%), flash glucose monitoring for 6 months significantly reduced the time spent in hypoglycemia compared with SMBG (P<0.0001). The mean change from baseline of −1.39 vs. −0.14 hours/day equated to a 38% reduction. In this 6-month study, the mean±SD number of scans/day recorded by the flash glucose monitoring device was 15.1±6.9, which was almost triple the frequency of blood glucose testing (5.5±2.0 tests/day). A prespecified subgroup analysis of the IMPACT trial showed the benefit of flash glucose monitoring in patients receiving multiple daily insulin injection therapy, as evidenced by a 46% reduction in time spent in hypoglycemia compared with SMBG (mean change from baseline −1.65 vs. 0.00 hours/day; P<0.0001).

A 1-year observational real-world cohort study of adults with T1D treated in specialist Belgian diabetes centers found that flash glucose monitoring improved treatment satisfaction and reduced severe hypoglycemia whilst maintaining HbA1c levels. Compared with the year before the study, flash glucose monitoring reduced admissions for severe hypoglycemia and/or ketoacidosis (3.3 vs. 2.2%; P=0.031), and reduced the incidence of reported severe hypoglycemic events (14.6 vs. 7.8%, P>0.0001) and hypoglycemic coma (2.7 vs. 1.2% P=0.001).

The REPLACE open-label randomized controlled trial (RCT) of adults with T2D, which is incorporated by reference in its entirety herein, compared the efficacy and safety of flash glucose monitoring (n=149) with SMBG (n=75). The study assessed the effect of flash glucose monitoring on glycemic control in patients receiving intensive insulin therapy or continuous subcutaneous insulin infusion. Although no significant difference was observed between flash technology and SMBG in the primary outcome measure of change in HbA1c at 6 months (mean −0.29 vs. −0.31%, respectively), prespecified subgroup analyses demonstrated several benefits, as shown in FIG. 17A. The 6-month HbA1c level was significantly reduced in patients aged <65 years using the flash system compared with SMBG (mean −0.53 vs. −0.20%; P=0.030) although the trend was reversed in patients aged >65 years (mean −0.05 vs. −0.49%; P=0.008). As further demonstrated in FIG. 17A, other glycemic measures significantly reduced with flash glucose monitoring compared with SMBG include time spent in hypoglycemia, frequency of hypoglycemic events and area under the concentration-time curve (AUC) for glucose, with a reduction in each of these measures in inverse proportion to the glucose level. SMBG frequency from baseline to study end was decreased in flash glucose monitoring participants from a mean±standard deviation (SD) of 3.8±1.4 to 0.3±0.7 tests/day. Treatment satisfaction, as assessed by the Diabetes Treatment Satisfaction Questionnaire, was higher in the flash glucose monitoring group compared with the SMBG group (mean±SE 13.1±0.50 vs. 9.0±0.72; P<0.0001). No serious adverse events (SAEs) or severe hypoglycemic events were reported in association with the device.

A total of 139 participants in the flash glucose monitoring group of the REPLACE RCT completed the 6-month treatment phase and continued into a 6-month open-access phase. The mean changes from baseline (start of treatment period) in glycemic parameters measured at 12 months paralleled those measured at 6 months. In FIG. 17A, reductions in sensor measures of time spent in hypoglycemia, number of hypoglycemic events, and glucose AUC were observed for open-access participants at 12 months post-baseline compared with baseline, and the magnitude of change increased as glucose cut-off points decreased.

Time in range (sensor glucose 70-180 mg/dL) remained unchanged between baseline and 12 months post-baseline (14.0±4.4 vs. 14.1±4.0 hours). Mean±SD frequency of SMBG decreased from 3.9±1.2 tests/day at baseline to 0.2±0.6 tests/day at 12 months post-baseline. During 12 months' use of the flash glucose monitoring device there were no reports of diabetic ketoacidosis or a state of hyperosmolar hyperglycemia. No SAEs were attributable to the device. Sixteen device-related adverse events (sensor adhesive or site reactions) were reported in nine participants, which were classified as severe (n=4), moderate (n=9) or mild (n=3). All events resolved after treatment with mainly topical preparations.

Collectively, the 6-month REPLACE RCT and follow-on 6-month open-access study showed that, in individuals with T2D managed by intensive insulin therapy, the flash glucose monitoring system reduces hypoglycemia and is a safe alternative to SMBG. In the initial 6-month phase, the mean±SD number of scans/day recorded by the flash glucose monitoring device was 8.3±4.4 (median 6.8), which was double the frequency of blood glucose testing (median 3.8±1.9 tests/day). Average sensor-scanning frequency during the extension phase was 7.1±3.5 times/day (median 5.7).

A further RCT compared the effect on glycemia of intermittent wearing of the professional flash glucose monitoring sensor with SMBG in insulin-treated T2D patients with a HbA1c level between 7.5 and 12.0%. Patients performed SMBG (n=52, control group A), or SMBG plus flash sensor worn for two 14-day periods during 4.5 months (n=46, intervention group B), or SMBG plus flash sensor worn for four 14-day periods during 7 months (n=50, intervention group C). No significant changes were observed within group C for sensor-derived time in range (70-180 mg/dL) from baseline to penultimate sensor wear (days 172-187; endpoint), with mean±SD values of 15.0±5.0 and 14.1±4.7 hours/day, respectively, or for the difference versus the control group at study end (days 215-230). In group C, HbA1c was reduced significantly during the study period by a mean±SD of 0.44%±0.81% (P=0.0003). At study end, HbA1c was significantly reduced in group C compared with the control group by an adjusted mean±SE of 0.48%±0.16% (P=0.004). In contrast, there was no significant difference in HbA1c between group B and control group at day 144 (P=0.133).

A further open-label RCT compared the effect of 10-week flash glucose monitoring (n=53) or SMBG (n=48) on glycemic control in patients with T2D receiving multiple daily insulin injections. HbA1c was significantly reduced in the flash device group compared with SMBG, with mean changes from baseline of −0.82% and −0.33%, respectively (P=0.005). Non-prespecified post hoc analyses showed that higher proportions of patients in the flash device group, compared with the SMBG group, had HbA1c reductions of ≥0.5% (68.6 vs. 30.2%; P<0.001), or of >1.0% (39.2 vs. 18.6%; P=0.0023). No significant differences were found in the mean±SD perceived frequency of hypoglycemic episodes: 1.41±1.29 vs. 0.75±1.57, respectively (P=0.066). There was a trend towards higher treatment satisfaction in the flash device group, with a mean Diabetes Treatment Satisfaction Questionnaire change version score of 2.47±0.77 compared with 2.18±0.83 in the standard care group (P=0.053). Patients found flash glucose monitoring to be significantly more flexible than SMBG (2.28±1.28 vs. 1.61±1.59, P=0.019), and more would recommend it to their counterparts (2.61±0.86 vs. 2.19±1.04, P=0.023).

Further retrospective real-world chart review studies from three European countries examined the effectiveness of flash glucose monitoring on HbA1c in adults with T2D managed by basal bolus insulin therapy. Medical records from centers in Austria (n=92), France (n=88) and Germany (n=183) were evaluated prior to, and following, use of the device for 90 days. Mean±SD changes in HbA1c were −0.9%±0.8% (P<0.0001), −0.8%±1.1% (P<0.0001) and −0.9%±1.1% (P<0.0001), respectively. In a combined analysis of the three studies, the overall effect size was −0.9% (P<0.0001 vs. baseline). There was no significant heterogeneity between studies performed in each country (P=0.711). No significant differences were recorded for changes in HbA1c according to age group, gender, body mass index, or duration of insulin use.

A real-world retrospective, observational study, which analyzed data from the US electronic health record database IBM Explorys, showed that de novo prescription of flash glucose monitoring significantly reduced HbA1c in T2D patients (n=1034) not using bolus insulin. Mean HbA1c levels decreased from 10.1% at baseline to 8.6% within 60-300 days of the flash glucose monitoring prescription (P<0.001). Similarly, another real-world retrospective study which analyzed claims data by the Decision Resources Group, a commercial medical and pharmacy claims database, showed a significant reduction in HbA1c levels in T2D patients on long-acting insulin or non-insulin therapy after 6-month and 12-month use of flash glucose monitoring. Mean HbA1c was reduced by 0.8% (from 8.5% to 7.7%) in the 6-month T2D cohort (n=774), and by 0.6% (from 8.5% to 7.9%) in the 12-month T2D cohort (n=207) (both P<0.0001).

Patient inclusion criteria differed among studies with some patient populations using intensive insulin therapy and others not. The 12-month General Practice Optimising Structured Monitoring To achieve Improved Clinical Outcomes (GP-OSMOTIC) trial, which compared professional-mode (masked) flash glucose monitoring with usual care (non-insulin glucose-lowering drugs, insulin, or both) in 299 adults with T2D in primary care, reported a significant reduction in mean HbA1c with flash monitoring at 6 months (−0.5%; P=0.0001) but not at 12 months (−0.3%; P=0.059), although the mean percentage of time spent in target glucose range at 12 months was 7.9% higher with flash monitoring than usual care (P=0.0060).

Two recent real-world retrospective, observational analyses of the MarketScan database, which contains insurance billing claims for inpatient, outpatient, and pharmacy expenses, have shown benefits for flash glucose monitoring beyond glycemic control. In T2D patients not using bolus insulin (n=7167), de novo flash glucose monitoring use (purchased between Q4 of 2017 and Q4 of 2018) significantly reduced inpatient and outpatient emergency acute diabetes events from 0.071 to 0.052 events/patient-year (hazard ratio [HR]: 0.70; 95% CI: 0.57-0.85; P<0.001), and all-cause hospitalization from 0.180 to 0.161 events/patient-year (HR: 0.87; 95% CI: 0.78-0.98; P=0.025). In T2D patients receiving fast- or short-acting insulin, flash glucose monitoring use (purchased between Q4 of 2017 and Q2 of 2018) significantly reduced acute diabetes events from 0.158 to 0.077 events/patient-year (HR: 0.49; 95% CI: 0.34-0.69; P<0.001) and all-cause hospitalization from 0.345 to 0.247 events/patient-year (HR: 0.72; 95% CI: 0.58-0.88; P=0.002).

Further real-world observational studies from several world regions have assessed the impact of flash glucose monitoring in often large groups of patients with T1D or T2D.

A retrospective nationwide study of reimbursement claims from a French database assessed ketoacidosis rates in T1D (n=33,203) and T2D (n=40,955) patients who initiated flash glucose monitoring use during a 5-month study period in 2017.

Four studies assessed the benefits of flash glucose monitoring mainly on HbA1c. A Dutch prospective nationwide registry study which analyzed data from 1365 participants with T1D (77.2%), T2D (16.4%), Latent Autoimmune Diabetes in Adults (4.6%) or maturity-onset diabetes of the young (0.5%) examined the effect of flash glucose monitoring on HbA1c, disease burden and well-being. A cohort study using data from the Swedish National Diabetes Register (January 2014-June 2019) assessed the effectiveness of a continuous glucose monitoring system (e.g., without limitation, FreeStyle Libre system) on HbA1c reduction. A meta-analysis of 29 clinical trials and real-world studies, of which 25 reported longitudinal HbA1c data in 1723 participants with T1D or T2D using the FreeStyle Libre system, examined the impact of flash glucose monitoring on HbA1c. A study from Israel assessed the impact of flash glucose monitoring on HbA1c in T2D (n=25) and T1D (n=6) patients.

Other studies assessed the impact of increased scanning frequency on glycemic measures. A real-world European analysis examined deidentified data from more than 50,000 users worldwide of the FreeStyle Libre system who had performed more than 60 million scans over a 20-month period. To assess the role of flash glucose monitoring in early and late changes of glycemic markers under real-life conditions, a longitudinal study analyzed deidentified glucose results from 6802 flash monitors after stratification into high, medium and low-risk groups based on tertiles of time spent in hypoglycemia (min/day <70 mg/dL) or hyperglycemia (hours/day >240 mg/dL). Another large real-world study analyzed deidentified glucose and user scanning data (250 million glucose readings, 37.1 million glucose scans) collected over a 4-year period from Spanish users (n=22, 949) to determine the relationship between testing frequency and glycemic parameters. An interesting study from Brazil analyzed glucose results captured from launch of the FreeStyle Libre flash glucose monitor in 2016 and compared them with global population data collected between September 2014 and December 2018. Data were analyzed from 688,640 readers and 7,329,052 sensors worldwide, including 17,691 readers and 147,166 sensors from Brazil.

As illustrated in FIG. 17B, four studies show that flash glucose monitoring improved glycemic control, as assessed by HbA1c, compared with prior to its use. In the Dutch prospective registry study, estimated HbA1c decreased from 8.0% before use of flash glucose monitoring to 7.6% after 6 months of use (P<0.001) and remained steady at 7.6% at 12 months (P<0.001). The 12-month difference in estimated HbA1c was more pronounced in patients with T2D (n=223) than T1D (n=1054). Swedish National Diabetes Register data also showed a significant decrease in HbA1c (method of measurement unspecified) before and after incident FreeStyle Libre use, with a mean change of −0.33% for T1D patients (n=8,316) and −0.52% for T2D patients (n=538) at 12 months (both P<0.0001). The meta-analysis of clinical trials and real-world studies of flash glucose monitoring indicated a mean change in laboratory HbA1c of −0.55% at 2-4 months, with a negligible difference (−0.56% and −0.54%, respectively) observed between adults (n=1023) and children and adolescents (n=447). Longitudinal analysis of studies involving adult subjects (n=1276) showed that laboratory HbA1c was reduced within the first 2 months of use, and that changes were sustained for up to 12 months, thus confirming a trend observed in a previous small study of flash glucose monitoring in patients with HbA1c >7.5%, in which the majority of change from baseline in mean HbA1c (method of measurement unspecified) occurred by 8 weeks (−1.33%; P<0.0001) and was maintained at 24 weeks (−1.21%; P=0.009).

Additional studies, illustrated in FIG. 17B, show that people who scan more tend to have lower HbA1c. In the European real-world analysis, greater scanning frequency from 4.4 (lowest) to 48.1 (highest) scans/day was associated with a reduction in estimated HbA1c from 8.0% to 6.7% (P<0.001). In the real-world study of Spanish users of the flash glucose monitoring device, estimated HbA1c was significantly lower in the highest (39.6 scans/day) versus lowest (3.9 scans/day) scan frequency group (6.9 vs. 8.0%; P<0.001). Similarly, the Brazilian study found that, in line with worldwide data, increased scanning frequency in Brazil was associated with better glycemic control, as evidenced by a lower estimated HbA1c in the highest (43.1 scans/day) versus lowest (3.6 scans/day) scan rate groups (6.7 vs. 7.6%; P<0.01).

FIG. 17C further illustrates results from four real-world studies showing that increased scanning frequency of the flash monitoring device was associated with benefits on glycemic measures apart from HbA1c.

In a European analysis, greater scanning frequency was inversely correlated with time spent in hypoglycemia and hyperglycemia. For blood glucose levels <70 mg/dL, <56 mg/dL and <45 mg/dL, time in hypoglycemia was lower by 15%, 40% and 49%, respectively (all P<0.001) in the highest (48.1 scans/day) compared with the lowest (4.4 scans/day) scan rate group. Highest versus lowest scanning frequency was also associated with a 44% decrease (P<0.001) in time spent in hyperglycemia and a 40% increase in time in range. Six-month data from the real-world longitudinal study showed that, in the high-risk hypoglycemia group, flash glucose monitoring significantly (P<0.0001) reduced the mean time spent in hypoglycemia (blood glucose ≤70 mg/dL) from the first to last 14-day periods of the study, irrespective of scanning frequency (high, medium, or low). In the high-risk hyperglycemia group, flash glucose monitoring reduced the time spent in hyperglycemia (blood glucose >240 mg/dL) by 0.8 hours/day in higher-frequency scanners (P<0.0001), by 0.3 hours/day in medium-frequency scanners (P=0.02), and had no effect in low-frequency scanners from the first to last 14-day periods of the study.

In a real-world study of Spanish users of the flash glucose monitoring device, glucose parameters progressively improved as average scanning frequency increased from the lowest (3.9 scans/day) to highest (39.6 scans/day) scan rate group. Time in hypoglycemia for blood glucose thresholds of <70 mg/dL and ≤54 mg/dL, respectively, was decreased by 14% and 37% in the highest versus lowest scan rate group. Respective times in hypoglycemia for the highest and lowest scan rate groups were 85.3 and 99.2 min/day (P<0.001) for blood glucose <70 mg/dL; and 29.7 min/day and 46.8 min/day for blood glucose ≤54 mg/dL. Time spent in hyperglycemia (blood glucose >180 mg/dL) was decreased by 37% (P<0.001), and time in range was increased by 36% (P<0.001) and in the highest versus lowest scan rate group. A comparison of sensor data derived from flash glucose monitoring users in Brazil and worldwide showed significant (P<0.01) improvements in time spent in hyperglycemia (blood glucose >180 mg/dL) associated with highest versus lowest scanning frequency: 43.1 and 3.6 scans/day, respectively, in Brazil; 37.8 and 3.4 scans/day, respectively, worldwide. In both populations, greater scanning frequency also increased time in range (blood glucose 70-180 mg/dL).

The retrospective study analyzing reimbursement claims from a French database showed a marked reduction in ketoacidosis rates in patients who initiated flash glucose monitoring during a 5-month study period in 2017. The hospitalization rate for ketoacidosis (excluding incidence for coma) was reduced by 52% (from 5.5 to 2.6 per 100 patient-years) and by 47% (from 1.7 to 0.9 per 100 patient-years) in T1D and T2D patients, respectively.

In a Dutch prospective registry study, 12-month use of flash glucose monitoring significantly reduced the proportion of patients experiencing any hypoglycemic event from 93.5% to 91.0%; the proportion of diabetes-related hospitalization from 13.7% to 4.7%; and work absenteeism from 18.5% to 7.7% (all comparisons P<0.05). In addition, flash glucose monitoring improved 12-month well-being scores, with changes from baseline of 0.03 (95% CI 0.01-0.05) in the EuroQol 5D tariff, 4.4 (95% CI 2.1-6.7) in the EQ-visual analogue scale, and 3.3 (95% CI 2.1-4.4) in the 12-Item Short Form Health Survey v2 mental component score.

While the disclosed subject matter is described herein in terms of certain illustrations and examples, those skilled in the art will recognize that various modifications and improvements may be made to the disclosed subject matter without departing from the scope thereof. Moreover, although individual features of one embodiment of the disclosed subject matter may be discussed herein or shown in the drawings of one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for the purposes of illustration and description. It is not intended to be exhaustive or to limit the disclosed subject matter to those embodiments disclosed.

The description herein merely illustrates the principles of the disclosed subject matter. Various modifications and alterations to the described embodiments will be apparent to those skilled in the art in view of the teachings herein. Accordingly, the disclosure herein is intended to be illustrative, but not limiting, of the scope of the disclosed subject matter.

What is claimed is:

1. A glucose monitoring system, comprising:
   a sensor control device comprising an analyte sensor coupled with sensor electronics, the sensor control device configured to transmit data indicative of an analyte level; and
   a reader device comprising a wireless communication circuitry configured to receive the data indicative of the analyte level; and
   one or more processors coupled with a memory, the memory configured to store instructions that, when executed by the one or more processors, cause the one or more processors to:
      determine a frequency of interaction over a first time period based on one or more instances of user operation of the reader device;
      output a first notification on a user interface of the reader device if the determined frequency of interaction is at or below a predetermined target level of interaction, wherein the first notification indicates the user's frequency of interaction with the reader device and provides a recommendation for user to increase interaction with the reader device to target a first improvement in a metabolic parameter of the user;
      output a second notification on the user interface of the reader device if the determined frequency of interaction is above the predetermined target level of interaction, wherein the second notification indicates the frequency of interaction with the reader device and provides a recommendation for user to maintain the frequency of interaction with the reader device to target a second improvement in the metabolic parameter of the user, wherein the first improvement is greater than the second improvement.

2. The system of claim 1, wherein the first time period is selected from a group consisting of a date range, one day, one week, two weeks, 30 days, or 90 days.

3. The system of claim 1, wherein the one or more instances of user operation of the reader device comprises a user view a current analyte level.

4. The system of claim 1, wherein the metabolic parameter is HbA1c.

5. The system of claim 4, wherein the instructions, when executed by the one or more processors, cause the one or more processors to output the second notification if HbA1c is above a predetermined level.

6. The system of claim 4, wherein the first improvement is a reduction in HbA1c of 0.02-0.12% per user operation of the reader device.

7. The system of claim 6, wherein the user operation of the reader device comprises a user scan of the reader device.

8. The system of claim 6, wherein the first improvement is a reduction in HbA1c of 0.07% per user operation of the reader device.

9. The system of claim 8, wherein the one or more instances of user operation of the reader device comprises a user scan of the reader device.

10. The system of claim 5, wherein the second improvement is a reduction in HbA1c of at least 0.03% per user operation of the reader device.

11. The system of claim 10, wherein the one or more instances of user operation of the reader device comprises a user scan of the reader device.

12. The system of claim 1, wherein the metabolic parameter is time in target range.

13. The system of claim 12, wherein the instructions, when executed by the one or more processors, cause the one or more processors to output the first notification if the time in target range is at or below a predetermined level.

14. The system of claim 13, wherein the first improvement is an increase in time in target range of 3-19 minutes per day per user operation of the reader device.

15. The system of claim 14, wherein the one or more instances of user operation of the reader device comprises a user scan of the reader device.

16. The system of claim 14, wherein the first improvement is an increase in time in target range of 11 minutes per day per additional user operation of the reader device.

17. The system of claim 16, wherein the user operation of the reader device comprises a user scan of the reader device.

18. The system of claim 13, wherein the second improvement is an increase in time in target range of approximately at least 7 minutes per user operation of the reader device.

19. The system of claim 18, wherein the user operation of the reader device comprises a user scan of the reader device.

20. The system of claim 1, wherein the metabolic parameter is time spent in hypoglycemia.

21. The system of claim 20, wherein the predetermined target level of interaction is 8 scans per day.

22. The system of claim 1, wherein the predetermined target level of interaction is 14 scans per day.

23. The system of claim 1, wherein the first time period comprises one or more second time periods, and wherein the instructions, when executed by the one or more processors, cause the one or more processors to record no more than one instance of user operation of the reader device during each second time period.

24. The system of claim 23, wherein the one or more second time periods is an increment of one hour and the first time period is one day.

25. The system of claim 1, wherein the first or second notification comprises a visual notification.

26. The system of claim 1, wherein the first or second notification comprises an audio notification.

27. The system of claim 1, wherein the first or second notification is at least one of an alert or a prompt.

28. A glucose monitoring system, comprising:
a sensor control device comprising an analyte sensor coupled with sensor electronics, the sensor control device configured to transmit data indicative of an analyte level;
a reader device comprising wireless communication circuitry configured to receive the data indicative of the analyte level; and
one or more processors coupled with a memory, the memory configured to store instructions that, when executed by the one or more processors, cause the one or more processors to:
record a time corresponding to a first user operation of the reader device;
record a time corresponding to a second user operation of the reader device, wherein the second user operation is after the first user operation;
calculate a time elapsed between the first user operation and the second user operation;
determine a frequency of interaction over a time period based on user operation of the reader device; and
output a notification and recommendation if the calculated time elapsed is equal to or greater than a predetermined time period,
wherein the notification is an alert if the determined frequency of interaction is below a predetermined target level of interaction and the notification provides a recommendation for user to increase interaction with the reader device to target a first improvement in a metabolic parameter of the user; and
output a prompt and recommendation if the determined frequency of interaction is above the predetermined target level of interaction and the prompt provides a recommendation for user to maintain the determined frequency of interaction to target a second improvement in the metabolic parameter of the user, wherein the first improvement is greater than the second improvement.

29. The glucose monitoring system of claim 28, wherein the predetermined target level of interaction is 14 scans per day.

30. The glucose monitoring system of claim 28, wherein the predetermined target level of interaction is 14 views per day.

31. The system of claim 28, wherein the notification comprises displaying a current analyte concentration value.

32. The system of claim 28, wherein the metabolic parameter is HbA1c.

33. The system of claim 32, wherein the first improvement is a reduction in HbA1c of 0.02-0.12% per user operation of the reader device.

34. The system of claim 32, wherein the first improvement is a reduction in HbA1c of 0.07% per user operation of the reader device.

35. The system of claim 32, wherein the second improvement is a reduction in HbA1c of at least 0.03% per user operation of the reader device.

36. The system of claim 28, wherein the metabolic parameter is time in target range.

37. The system of claim 36, wherein the first improvement is an increase in time in target range of 3-19 minutes per day per user operation of the reader device.

38. The system of claim 36, wherein the first improvement is an increase in time in target range of 11 minutes per day per additional user operation of the reader device.

39. The system of claim 36, wherein the second improvement is an increase in time in target range of approximately at least 7 minutes per user operation of the reader device.

40. A glucose monitoring system, comprising:
a sensor control device comprising an analyte sensor coupled with sensor electronics, the sensor control device configured to transmit data indicative of an analyte level;
a reader device comprising wireless communication circuitry configured to receive the data indicative of the analyte level; and one or more processors coupled with a memory, the memory configured to store instructions that, when executed by the one or more processors, cause the one or more processors to:

record a time corresponding to a user interaction with the reader device;

calculate a time elapsed from the user interaction to a current time; and output a notification and recommendation for a subsequent user interaction within a time period, wherein the time period is based on a predetermined target level of interaction, wherein the notification provides the recommendation for user (i) to increase interaction with the reader device when below the predetermined target level of interaction to target a first improvement in a metabolic parameter of the user or (ii) to maintain the determined frequency of interaction when the determined frequency of interaction is above the predetermined target level of interaction to target a second improvement in the metabolic parameter of the user, wherein the first improvement is greater than the second improvement.

41. The system of claim 40, wherein the notification comprises displaying a current analyte concentration value.

42. The system of claim 40, wherein a second notification is output if a second user interaction is not recorded within the time period.

43. The system of claim 40, wherein the user interaction comprises a user scan of the reader device and is 14 scans per day.

44. The system of claim 40, wherein the user interaction comprises a user view of a current analyte level.

45. The system of claim 40, wherein the metabolic parameter is HbA1c.

46. The system of claim 45, wherein the first improvement is a reduction in HbA1c of 0.02-0.12% per user operation of the reader device.

47. The system of claim 45, wherein the first improvement is a reduction in HbA1c of 0.07% per user operation of the reader device.

* * * * *